US008883752B2

(12) United States Patent
Swayze et al.

(10) Patent No.: US 8,883,752 B2
(45) Date of Patent: Nov. 11, 2014

(54) 5' AND 2' BIS-SUBSTITUTED NUCLEOSIDES AND OLIGOMERIC COMPOUNDS PREPARED THEREFROM

(75) Inventors: Eric E. Swayze, Encinitas, CA (US); Thazha P. Prakash, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 466 days.

(21) Appl. No.: 13/125,557

(22) PCT Filed: Oct. 23, 2009

(86) PCT No.: PCT/US2009/061913
§ 371 (c)(1),
(2), (4) Date: Jul. 12, 2011

(87) PCT Pub. No.: WO2010/048549
PCT Pub. Date: Apr. 29, 2010

(65) Prior Publication Data
US 2011/0269821 A1    Nov. 3, 2011

Related U.S. Application Data

(60) Provisional application No. 61/108,457, filed on Oct. 24, 2008, provisional application No. 61/149,297, filed on Feb. 2, 2009, provisional application No. 61/163,217, filed on Mar. 25, 2009, provisional application No. 61/174,137, filed on Apr. 30, 2009, provisional application No. 61/239,672, filed on Sep. 3, 2009, provisional application No. 61/150,492, filed on Feb. 6, 2009.

(51) Int. Cl.
*A01N 43/04* (2006.01)
*A61K 31/70* (2006.01)
*A61K 48/00* (2006.01)
*C07H 21/00* (2006.01)
*A61K 31/00* (2006.01)

(52) U.S. Cl.
CPC ............... *C07H 21/00* (2013.01); *A61K 31/00* (2013.01)
USPC ........................................ 514/44 R; 536/24.5

(58) Field of Classification Search
CPC .................................. C07H 21/00; A61K 31/00
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,668,777 A | 5/1987 | Caruthers et al. |
| 4,725,677 A | 2/1988 | Koster et al. |
| 4,845,205 A | 7/1989 | Huynh et al. |
| 4,973,679 A | 11/1990 | Caruthers et al. |
| 4,981,957 A | 1/1991 | Lebleu et al. |
| 5,013,830 A | 5/1991 | Ohtsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,069 E | 9/1992 | Koster et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,599 A | 3/1993 | Froehler |
| 5,214,134 A | 5/1993 | Weis et al. |
| 5,216,141 A | 6/1993 | Benner |
| 5,220,007 A | 6/1993 | Pederson et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |

(Continued)

FOREIGN PATENT DOCUMENTS

AU      A-57590/94       9/1994
AU      A-64522/94      12/1994

(Continued)

OTHER PUBLICATIONS (R) Böhringer et al., "Syntheses of 5'-deoxy-5'-methylphosphonate Linked Thymidine Oligonucleotides," Tetrahedron Letters, 34(17), 2723-2726 (Apr. 23, 1993).*
Abbas et al., "Commercially Available 5'-DMT Phosphoramidites as Reagents for the Synthesis of Vinylphosphonate-Linked Oligonucleic Acids" Organic Letters (2001) 3(21):3365-3367.
Whittaker et al., "Stereoselective synthesis of highly functionalised P-stereogenic nucleosides via palladium-catalysed P-C cross-coupling reactions" Tetrahedron Letters (2008) 49:6984-6987.
Zhao, "Synthesis and preliminary biochemical studies with 5'-deoxy-5'-methylidyne phosphonate linked thymidine oligonucleotides" Tetrahedron Letters (1996) 37(35):6239-6242.
International Search Report for application PCT/US2011/033968 dated Mar. 11, 2013.
Elbashir et al., "Functional anatomy of siRNAs for mediating efficient RNAi in Drosophila melanogaster embryo lysate" EMBO Journal (2001) 20(23):6877-6888.
Swayze et al., "The Medicinal Chemistry of Oligonucleotides" Antisense Drug Technology: Principles, Strategies, and Applications, Chapter 6, pp. 143-182, Jul. 25, 2007, CRC Press.

(Continued)

Primary Examiner — Lawrence E Crane
(74) Attorney, Agent, or Firm — Casimir Jones, S.C.

(57) ABSTRACT

The present invention provides modified nucleosides and oligomeric compounds prepared therefrom. More particularly, the present invention provides modified nucleosides having at least one 5'-substituent and a 2'-O-substituent, oligomeric compounds comprising at least one of these modified nucleosides and methods of using the oligomeric compounds. In some embodiments, the oligomeric compounds provided herein are expected to hybridize to a portion of a target RNA resulting in loss of normal function of the target RNA.

23 Claims, No Drawings

(56) References Cited

U.S. PATENT DOCUMENTS

| | | | |
|---|---|---|---|
| 5,278,302 A | 1/1994 | Caruthers et al. | |
| 5,286,717 A | 2/1994 | Cohen et al. | |
| 5,319,080 A | 6/1994 | Leumann | |
| 5,321,131 A | 6/1994 | Agrawal et al. | |
| 5,359,044 A | 10/1994 | Cook et al. | |
| 5,366,878 A | 11/1994 | Pederson et al. | |
| 5,367,066 A | 11/1994 | Urdea et al. | |
| 5,378,825 A | 1/1995 | Cook et al. | |
| 5,386,023 A | 1/1995 | Sanghvi et al. | |
| 5,393,878 A | 2/1995 | Leumann | |
| 5,399,676 A | 3/1995 | Froehler | |
| 5,403,711 A | 4/1995 | Walder et al. | |
| 5,405,938 A | 4/1995 | Summerton et al. | |
| 5,405,939 A | 4/1995 | Suhadolnik et al. | |
| 5,432,272 A | 7/1995 | Benner | |
| 5,434,257 A | 7/1995 | Matteucci | |
| 5,446,137 A | 8/1995 | Maag et al. | |
| 5,453,496 A | 9/1995 | Caruthers et al. | |
| 5,455,233 A | 10/1995 | Spielvogel et al. | |
| 5,457,187 A | 10/1995 | Gmelner et al. | |
| 5,459,255 A | 10/1995 | Cook et al. | |
| 5,466,677 A | 11/1995 | Baxter et al. | |
| 5,466,786 A | 11/1995 | Buhr et al. | |
| 5,470,967 A | 11/1995 | Huie et al. | |
| 5,476,925 A | 12/1995 | Letsinger et al. | |
| 5,484,908 A | 1/1996 | Froehler et al. | |
| 5,489,677 A | 2/1996 | Sanghvi et al. | |
| 5,491,133 A | 2/1996 | Walder et al. | |
| 5,502,177 A | 3/1996 | Matteucci et al. | |
| 5,508,270 A | 4/1996 | Baxter et al. | |
| 5,514,785 A | 5/1996 | Van Ness et al. | |
| 5,519,126 A | 5/1996 | Hecht | |
| 5,519,134 A | 5/1996 | Acevedo et al. | |
| 5,525,711 A | 6/1996 | Hawkins et al. | |
| 5,527,899 A | 6/1996 | Froehler | |
| 5,536,821 A | 7/1996 | Agrawal et al. | |
| 5,541,306 A | 7/1996 | Agrawal et al. | |
| 5,541,307 A | 7/1996 | Cook et al. | |
| 5,550,111 A | 8/1996 | Suhadolnik et al. | |
| 5,552,540 A | 9/1996 | Haralambidis | |
| 5,561,225 A | 10/1996 | Maddry et al. | |
| 5,563,253 A | 10/1996 | Agrawal et al. | |
| 5,565,350 A | 10/1996 | Kmiec | |
| 5,565,555 A | 10/1996 | Froehler et al. | |
| 5,567,811 A | 10/1996 | Mistura et al. | |
| 5,571,799 A | 11/1996 | Tkachuk et al. | |
| 5,576,427 A | 11/1996 | Cook et al. | |
| 5,587,361 A | 12/1996 | Cook et al. | |
| 5,587,469 A | 12/1996 | Cook et al. | |
| 5,591,722 A | 1/1997 | Montgomery et al. | |
| 5,594,121 A | 1/1997 | Froehler et al. | |
| 5,596,086 A | 1/1997 | Matteucci | |
| 5,596,091 A | 1/1997 | Switzer | |
| 5,597,909 A | 1/1997 | Urdea et al. | |
| 5,602,240 A | 2/1997 | De Mesmaeker et al. | |
| 5,608,046 A | 3/1997 | Cook et al. | |
| 5,610,289 A | 3/1997 | Cook et al. | |
| 5,610,300 A | 3/1997 | Altmann et al. | |
| 5,614,617 A | 3/1997 | Cook et al. | |
| 5,618,704 A | 4/1997 | Sanghvi et al. | |
| 5,623,065 A | 4/1997 | Cook et al. | |
| 5,623,070 A | 4/1997 | Cook et al. | |
| 5,625,050 A | 4/1997 | Beaton et al. | |
| 5,627,053 A | 5/1997 | Usman et al. | |
| 5,633,360 A | 5/1997 | Bischofberger et al. | |
| 5,639,873 A | 6/1997 | Barascut et al. | |
| 5,645,985 A | 7/1997 | Froehler et al. | |
| 5,646,265 A | 7/1997 | McGee | |
| 5,646,269 A | 7/1997 | Matteucci | |
| 5,652,355 A | 7/1997 | Metelev et al. | |
| 5,652,356 A | 7/1997 | Agrawal | |
| 5,663,312 A | 9/1997 | Chaturvedula | |
| 5,670,633 A | 9/1997 | Cook et al. | |
| 5,672,697 A | 9/1997 | Buhr et al. | |
| 5,677,437 A | 10/1997 | Teng et al. | |
| 5,677,439 A | 10/1997 | Weis et al. | |
| 5,681,941 A | 10/1997 | Cook et al. | |
| 5,700,920 A | 12/1997 | Altmann et al. | |
| 5,700,922 A | 12/1997 | Cook | |
| 5,712,378 A | 1/1998 | Wang | |
| 5,721,218 A | 2/1998 | Froehler | |
| 5,750,692 A | 5/1998 | Cook et al. | |
| 5,763,588 A | 6/1998 | Matteucci et al. | |
| 5,792,608 A | 8/1998 | Swaminathan et al. | |
| 5,792,847 A | 8/1998 | Buhr et al. | |
| 5,830,653 A | 11/1998 | Froehler et al. | |
| 5,929,226 A * | 7/1999 | Padmapriya et al. | 536/25.3 |
| 5,969,116 A | 10/1999 | Martin | |
| 6,005,096 A | 12/1999 | Matteucci et al. | |
| 6,426,220 B1 | 7/2002 | Bennett et al. | |
| 6,600,032 B1 | 7/2003 | Manoharan et al. | |
| 7,427,672 B2 | 9/2008 | Imanishi et al. | |
| 7,452,987 B2 | 11/2008 | Giese et al. | |
| 2001/0044145 A1 | 11/2001 | Monia et al. | |
| 2004/0171570 A1 | 9/2004 | Allerson et al. | |
| 2006/0074035 A1 | 4/2006 | Hong et al. | |
| 2011/0076681 A1 | 3/2011 | Waterhouse et al. | |

FOREIGN PATENT DOCUMENTS

| | | |
|---|---|---|
| WO | WO 92/13869 | 8/1992 |
| WO | WO 94/02499 | 2/1994 |
| WO | WO 94/17093 | 8/1994 |
| WO | WO 94/22890 | 10/1994 |
| WO | WO 96/04295 | 2/1996 |
| WO | WO 98/00434 | 1/1998 |
| WO | WO 99/14226 | 3/1999 |
| WO | WO 01/14400 | 3/2001 |
| WO | WO 02/36743 | 5/2002 |
| WO | WO 03/073989 | 9/2003 |
| WO | WO 2005/012371 | 12/2005 |
| WO | WO 2005/012372 | 12/2005 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |

OTHER PUBLICATIONS

European Search Report for application EP 12151431.9 dated Oct. 2, 2012.

Chen et al., "Strand-specific 5'-O-methylation of siRNA duplexes controls guide strand selection and targeting specificity" RNA (2008) 14:263-274.

Haringsma et al., "mRNA knockdown by single strand RNA is improved by chemical modifications" Nucleic Acids Research (2012) 40(9):4125-4136.

Lima et al., "Binding and Cleavage Specificities of Human Argonatue2" Journal of Biological Chemistry (2009) 284(38):26017-26028.

Lima et al., "Single-Stranded siRNAs Activate RNAi in Animals" Cell (2012) 15:883-894.

Agrawal et al., *Protocols for Oligonucleotide Conjugates*, Humana Press; New Jersey, 1994, 26, Ch 3.

Altschul et al., "Basic Local Alignment Search Tool" J. Mol. Biol. (1990) 215:403-410.

Ausubel et al., Current Protocols in Molecular Biology, vol. 2, pp. 11.12.1-11.12.9, John Wiley & Sons, 1997.

Barany et al., "A New Amino Protecting Group Removable by Reduction. Chemistry of the Dithiasuccinoyl (Dts) Function" J. Am. Chem. Soc. (1977) 99:7363-7365.

Barany et al., "Kinetics and Mechanisms of the Thiolytic Removal of the Dithiasuccinoyl (Dts) Amino Protecting Group" J. Am. Chem. Soc. (1980) 102:3084-3095.

Bass, "Double-stranded RNA as a template for gene silencing" Cell (2000) 101:235-238.

Beaucage et al., "The Functionalization of Oligonucleotides via Phosphoramidite Derivatives" Tetrahedron (1993) 49:1925-1963.

Beaucage et al., "The Synthesis of Specific Ribonucleotides and Unrelated Phosphorylated Biomolecules by the Phosphoramidite Method" Tetrahedron (1993) 49:10441-10488.

(56) References Cited

OTHER PUBLICATIONS

Beaucage et al., "Advances in the Synthesis of Oligonucleotides by the Phosphoramidite Approach" Tetrahedron (1992) 48:2223-2311.
Belikova et al., "Synthesis of Ribonucleosides and Diribonucleoside Phosphates Containing 2-Chloro-Ethylamine and Nitrogen Mustard Residues" Tet. Lett. (1967) 37:3557-3562.
Brazma et al., "Gene expression data analysis" FEBS Letters (2000) 480:17-24.
Carulli et al., "High Throughput Analysis of Differential Gene Expression" J. Cell. Biochem. Suppl. (1998) 30:286-296.
Celis et al., "Gene expression profiling: monitoring transcription and translation products using DNA microarrays and proteomics" FEBS Lett (2000) 480:2-16.
De Mesmaeker et al., "Amide-Modified Oligonucleotides with Preorganized Backbone and Furanose Rings: Highly Increased Thermodynamic Stability of the Duplexes Formed with their RNA and DNA Complements" Synlett (1997) 1287-1290.
Elbashir, "Duplexes of 21-nucleotide RNAs mediate RNA interference in cultured mammalian cells" Nature (2001) 411:494-498.
Elbashir, "RNA interference is mediated by 21- and 22-nucleotide RNAs" Genes & Devel. (2001) 15:188-200.
Englisch et al., "Chemically Modified Oligonucleotides as Probes and Inhibitors" Agnew Chem. Int. Ed. Engl. (1991) 30:613-629.
Eppacher et al., "Synthesis and Incorporation of C(5')-Ethynylated Uracil-Derived Phosphoramidites into RNA" Helvetica Chimica Acta (2004) 87(12):3004-3020.
Fire et al., "Potent and Specific Genetic Interference by Double-Stranded RNA in Caenorhabditis Elegans" Nature (1998) 391:806-811.
Fuchs et al., "Identification of Differentially Expressed Genes by Mutually Subtracted RNA Fingerprinting" Anal. Biochem. (2000) 286:91-98.
Gait et al., "Application of chemically synthesized RNA" RNA: Protein Interactions (1998) 1-36.
Gallo et al., "2'-C-Methyluridine Phosphoramidite: A New Building Block for the Preparation of RNA Analogues Carrying the 2'-Dydroxyl Group" Tetrahedron (2001) 57: 5707-5713.
Going et al., "Molecular Pathology and Future Developments" Eur. J. Cancer (1999) 35:1895-1904.
Jahn-Hofmann et al., "Efficient Solid Phase Synthesis of Cleavable Oligodeoxynucleotides Based on a Novel Strategy for the Synthesis of 5'-S-(4,4'-Dimethoxytrityl)-2'-deoxy-5'-thionucleoside Phosphoramidites" Helvetica Chimica Acta (2004) 87:2812-2828.
Jungblut et al., "Proteomics in human disease: Cancer, heart and infections diseases" Electrophoresis (1999) 20:2100-2110.
Jurecic et al., "Long-distance DD-PCR and cDNA microarrays" Curr. Opin. Microbio. (2000) 3:316-321.
Kroschwitz, "Polynucleotides" Concise Encyclopedia of Polymer Science and Engineering (1990) John Wiley & Sons, NY pp. 858-859.
Larson et al., "Rapid DNA Fingerprinting of Pathogens by Flow Cytometry" Cytometry (2000) 41:203-208.
Larsson et al., "High-throughput protein expression of cDNA products as a tool in functional genomics" J. Biotech. (2000) 80:143-157.
Liu et al., "Uridylyl-(3'-5')-(5'-thiouridine). An Exceptionally Base-labile Di-ribonucleoside Phosphate Analogue" Tetrahedron Letters (1995) 36(19):3413-3416.
Madden et al., "Serial analysis of gene expression: from gene discovery to target identification" DDT (2000) 5:415-425.
Mag et al., "Synthesis and selective cleavage of oligodeoxyribonucleotldes containing non-chiral intemucieotlde phosphoramidate linkages" Nucleic Acids Res. (1989) 17(15):5973-5988.
Matulic-Ademic et al., "Synthesis and incorporation of 5'-amino- and 5'-mercapto-5'-deoxy-2'-O-methyl nucleosides into hammerhead ribozymes" Nucleosides & Nucleotides (1997) 16:1933-1950.
Mikhailov et al., "Substrate Properties of C'-Methylnucleoside and C'-Methyl-2'-Deoxynucleoside 5'-Triphosphates in RNA and DNA Synthesis Reactions Catalysed by RNA and DNA Polymerases" Nucleosides &Nucleotides (1991) 10(1-3):339-343.
Miura et al., "Fluorometric determination of total mRNA with oligo(dT) immobilized on microtiter plates" Clin. Chem. (1996) 42:1758-1764.
Montgomery et al., "RNA as a target of double-stranded RNA-mediated genetic interference in Caenorhabditis elegans" Proc Natl. Acad. Sci. (1998) 95:15502-7.
Nishikura, "A Short Primer on RNAi: RNA-Directed RNA Polymerase Acts as a Key Catalyst" Cell (2001) 107:415-418.
Prashar et al., "READS: A Method for Display of 3'-End Fragment of Restriction Enzyme-Digested cDNAs for Analysis of Differential Gene Expression" Methods Enzymol. (1999) 303:258-272.
Saha et al., "5'-Me-DNA—A New Oligonucleotide Analog: Synthesis and Biochemical Properties" J. Org. Chem. (1995) 60:788-789.
Sanghvi, Chapter 15, Antisense Research and Applications, pp. 289-302, Crooke and Lebleu ed., CRC Press (1993).
Sutcliffe et al., "TOGA: An automated parsing technology for analyzing expression of nearly all genes" PNAS (2000) 97:1976-1981.
Tabara et al., "RNAi in C. elegans: Soaking in the Genome Sequence" Science (1998) 282:430-431.
Tijsterman et al., "RNA hellcase MUT-14-dependent gene silencing triggered in C. elegans by short antisense RNAs" Science (2002) 295:694-7.
Timmons et al., "Ingestion of bacterially expressed dsRNAs can produce specific and potent genetic interference in Caenorhabditis elegans" Gene (2001) 263:103-112.
Timmons et al., "Specific Interference by Ingested dsRNA" Nature (1998) 395:854.
To, "Identification of Differential Gene Expression by High Throughput Analysis" Comb. Chem. High Throughput Screen (2000) 3:235-241.
Tuschl et al., "Targeted mRNA degradation by double-stranded RNA in vitro" Genes Dev. (1999) 13:3191-7.
Wang et al., "Biophysical and Biochemical Properties of Oligodeoxynucleotides Containing 4'-C- and 5'-C- Substituted Thymidines" Bioorg. Med. Chem. Lett. (1999) 9:885-890.
Wang et al., "Synthesis of Azole Nucleoside 5'-Monophosphate Mimics (PIMs) and Their Inhibitory Properties of IMP Dehydrogenases" Nucleosides Nucleotides & Nucleic Acids (2004) 23(1&2):317-337.
Wu et al., "Functionalization of the Sugar Moiety of Oligoribonucleotides on Solid Support" Bioconjugate Chem. (1999) 10:921-924.
Wu et al., "Synthesis of 5'-C- and 2'-O-(Bromoalkyl)-Substituted Ribonucleoside Phosphoramidites for the Post-synthetic Functionalization of Oligonucleotides on Solid Support" Helvetica Chimica Acta (2000) 83:1127-1143.
Zamecnik et al., "Inhibition of Rous sarcoma virus replication and cell transformation by a specific oligodeoxynucleotide" PNAS (1978) 75:280-284.
Zhang et al., "PowerBLAST: A New Network BLAST Application for Interactive or Automated Sequence Analysis and Annotation" Genome Res. (1997) 7:649-656.
Zhou et al., "Fine Tuning of Electrostatics around the Interncleotidic Phosphate through Incorporation of Modified 2',4'-Carbocyclic-LNAs and -ENAs Leads to Significant Modulation of Antisense Properties" J. Org. Chem. (2009) 74:118-134.
International Search Report for application PCT/US2009/061913 dated Jul. 27, 2010.
International Search Report for application PCT/US2009/061959 dated Aug. 19, 2010.
Bertrand et al., "Comparison of antisense oligonucleotides and siRNAs in cell culture and in vivo" Biochemical and Biophysical Research Communications (2002) 296:1000-1004.
Matulic-Ademic et al., "Synthesis of 5'-Deoxy-5'-difluoromethyl Phosphonate Nucleotide Analogs" J. Org. Chem. (1995) 60:2563-2569.

\* cited by examiner

5' AND 2' BIS-SUBSTITUTED NUCLEOSIDES AND OLIGOMERIC COMPOUNDS PREPARED THEREFROM

CROSS REFERENCED TO RELATED APPLICATIONS

This application is a U.S. National Phase filing under 35 U.S.C. 371 claiming priority to International Serial No. PCT/US2009/061913 filed Oct. 23, 2009, which claims priority to U.S. Provisional Applications: 61/108,457, filed Oct. 24, 2008; 61/149,297, filed Feb. 2, 2009; 61/163,217, filed Mar. 25, 2009; 61/174,137, filed Apr. 30, 2009; 61/239,672, filed Sep. 3, 2009; and 61/150,492, filed Feb. 6, 2009, each of which is incorporated herein by reference in its entirety.

STATEMENT OF GOVERNMENT SUPPORT

This invention was made with United States Government support under contract #5R44GM076793-03 awarded by the NIH. The United States Government has certain rights in the invention.

SEQUENCE LISTING

The present application is being filed along with a Sequence Listing in electronic format. The Sequence Listing is provided as a file entitled CHEM0055USA2SEO.TXT, created on Apr. 13, 2011, which is 8 Kb in size. The information in the electronic format of the sequence listing is incorporated herein by reference in its entirety.

FIELD OF THE INVENTION

Provided herein are modified nucleosides and oligomeric compounds prepared therefrom. More particularly, modified nucleosides are provided having at least one 5'-substituent and a 2'-substituent, oligomeric compounds comprising at least one of these modified nucleosides and compositions comprising at least one of these oligomeric compounds. In some embodiments, the oligomeric compounds provided herein are expected to hybridize to a portion of a target RNA resulting in loss of normal function of the target RNA. The oligomeric compounds are also expected to be useful as primers and probes in diagnostic applications.

BACKGROUND OF THE INVENTION

Targeting disease-causing gene sequences was first suggested more than thirty years ago (Belikova et al., Tet. Lett., 1967, 37, 3557-3562), and antisense activity was demonstrated in cell culture more than a decade later (Zamecnik et al., Proc. Natl. Acad. Sci. U.S.A., 1978, 75, 280-284). One advantage of antisense technology in the treatment of a disease or condition that stems from a disease-causing gene is that it is a direct genetic approach that has the ability to modulate (increase or decrease) the expression of specific disease-causing genes. Another advantage is that validation of a therapeutic target using antisense compounds results in direct and immediate discovery of the drug candidate; the antisense compound is the potential therapeutic agent.

Generally, the principle behind antisense technology is that an antisense compound hybridizes to a target nucleic acid and modulates gene expression activities or function, such as transcription or translation. The modulation of gene expression can be achieved by, for example, target degradation or occupancy-based inhibition. An example of modulation of RNA target function by degradation is RNase H-based degradation of the target RNA upon hybridization with a DNA-like antisense compound. Another example of modulation of gene expression by target degradation is RNA interference (RNAi). RNAi generally refers to antisense-mediated gene silencing involving the introduction of dsRNA leading to the sequence-specific reduction of targeted endogenous mRNA levels. An additional example of modulation of RNA target function by an occupancy-based mechanism is modulation of microRNA function. MicroRNAs are small non-coding RNAs that regulate the expression of protein-coding RNAs. The binding of an antisense compound to a microRNA prevents that microRNA from binding to its messenger RNA targets, and thus interferes with the function of the microRNA. Regardless of the specific mechanism, this sequence-specificity makes antisense compounds extremely attractive as tools for target validation and gene functionalization, as well as therapeutics to selectively modulate the expression of genes involved in the pathogenesis of malignancies and other diseases.

Antisense technology is an effective means for reducing the expression of one or more specific gene products and can therefore prove to be uniquely useful in a number of therapeutic, diagnostic, and research applications. Chemically modified nucleosides are routinely used for incorporation into antisense compounds to enhance one or more properties, such as nuclease resistance, pharmacokinetics or affinity for a target RNA. In 1998, the antisense compound, Vitravene® (fomivirsen; developed by Isis Pharmaceuticals Inc., Carlsbad, Calif.) was the first antisense drug to achieve marketing clearance from the U.S. Food and Drug Administration (FDA), and is currently a treatment of cytomegalovirus (CMV)-induced retinitis in AIDS patients.

New chemical modifications have improved the potency and efficacy of antisense compounds, uncovering the potential for oral delivery as well as enhancing subcutaneous administration, decreasing potential for side effects, and leading to improvements in patient convenience. Chemical modifications increasing potency of antisense compounds allow administration of lower doses, which reduces the potential for toxicity, as well as decreasing overall cost of therapy. Modifications increasing the resistance to degradation result in slower clearance from the body, allowing for less frequent dosing. Different types of chemical modifications can be combined in one compound to further optimize the compound's efficacy.

The synthesis of 5'-substituted DNA and RNA derivatives and their incorporation into oligomeric compounds has been reported in the literature (Saha et al., *J. Org. Chem.,* 1995, 60, 788-789; Wang et al., *Bioorganic & Medicinal Chemistry Letters,* 1999, 9, 885-890; and Mikhailov et al., *Nucleosides & Nucleotides,* 1991, 10(1-3), 339-343; Leonid et al., 1995, 14(3-5), 901-905; and Eppacher et al., *Helvetica Chimica Acta,* 2004, 87, 3004-3020). The 5'-substituted monomers have also been made as the monophosphate with modified bases (Wang et al., *Nucleosides Nucleotides & Nucleic Acids,* 2004, 23 (1 & 2), 317-337).

A genus of modified nucleosides including optional modification at a plurality of positions including the 5'-position and the 2'-position of the sugar ring and oligomeric compounds incorporating these modified nucleosides therein has been reported (see International Application Number: PCT/US94/02993, Published on Oct. 13, 1994 as WO 94/22890).

The synthesis of 5'-CH$_2$ substituted 2'-O-protected nucleosides and their incorporation into oligomers has been previously reported (see Wu et al., *Helvetica Chimica Acta,* 2000, 83, 1127-1143 and Wu et al. *Bioconjugate Chem.* 1999, 10, 921-924).

Amide linked nucleoside dimers have been prepared for incorporation into oligonucleotides wherein the 3' linked nucleoside in the dimer (5' to 3') comprises a 2'-OCH$_3$ and a 5'-(S)—CH$_3$ (Mesmaeker et al., *Synlett,* 1997, 1287-1290).

A genus of 2'-substituted 5'-CH$_2$ (or O) modified nucleosides and a discussion of incorporating them into oligonucleotides has been previously reported (see International Application Number: PCT/US92/01020, published on Feb. 7, 1992 as WO 92/13869).

The synthesis of modified 5'-methylene phosphonate monomers having 2'-substitution and their use to make modified antiviral dimers has been previously reported (see U.S. patent application Ser. No. 10/418,662, published on Apr. 6, 2006 as US 2006/0074035).

There remains a long-felt need for agents that specifically regulate gene expression via antisense mechanisms. Disclosed herein are oligomeric compounds such as antisense compounds useful for modulating gene expression pathways, including those relying on mechanisms of action such as RNaseH, RNAi and dsRNA enzymes, as well as other antisense mechanisms based on target degradation or target occupancy. One having skill in the art, once armed with this disclosure will be able, without undue experimentation, to identify, prepare and exploit antisense compounds for these uses.

BRIEF SUMMARY OF THE INVENTION

Provided herein are modified nucleosides having at least one 2' substituent group and either a 5' substituent group, a 5' phosphorus moiety or both a 5' substituent group and a 5' phosphorus moiety, oligomeric compounds that include such modified nucleosides and methods of using the oligomeric compounds. Also provided herein are intermediates and methods for preparing these modified nucleosides and oligomeric compounds. In certain embodiments, modified nucleosides are provided that are 5'-mono (R, S or mixed) or bis substituted and 2'-O-substituted, that can be incorporated into oligomeric compounds. The modified nucleosides provided herein are expected to be useful for enhancing one or more properties of the oligomeric compounds they are incorporated into such as for example nuclease resistance. In certain embodiments, the oligomeric compounds and compositions provided herein that incorporate one or more of these modified nucleosides are expected to hybridize to a portion of a target RNA resulting in loss of normal function of the target RNA. The oligomeric compounds are also expected to be useful as primers and probes in diagnostic applications.

The variables are defined individually in further detail herein. It is to be understood that the modified nucleosides and oligomeric compounds provided herein include all combinations of the embodiments disclosed and variables defined herein.

In certain embodiments, compounds are provided herein having Formula I:

wherein:
Bx is a heterocyclic base moiety;
A is O, S or N(R$_1$);
R$_1$ is H, C$_1$-C$_6$ alkyl or substituted C$_1$-C$_6$ alkyl;
one of T$_1$ and T$_2$ is H, a protecting group or a phosphorus moiety and the other of T$_1$ and T$_2$ is H, a protecting group or a reactive phosphorus group;
one of Q$_1$ and Q$_2$ is H, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl or substituted C$_2$-C$_6$ alkynyl and the other of Q$_1$ and Q$_2$ is C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl or substituted C$_2$-C$_6$ alkynyl;
G$_1$ is O—[C(R$_2$)(R$_3$)]$_n$—[(C=O)$_m$—X]$_j$—Z or halogen;
each R$_2$ and R$_3$ is, independently, H or halogen;
X is O, S or N(E$_1$);
Z is H, halogen, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl or N(E$_2$)(E$_3$);
E$_1$, E$_2$ and E$_3$ are each, independently, H, C$_1$-C$_6$ alkyl or substituted C$_1$-C$_6$ alkyl;
n is from 1 to about 6;
m is 0 or 1;
j is 0 or 1;
each substituted group comprises one or more optionally protected substituent groups independently selected from halogen, OJ$_1$, N(J$_1$)(J$_2$), =NJ$_1$, SJ$_1$, N$_3$, CN, OC(=L)J$_1$, OC(=L)N(J$_1$)(J$_2$) and C(=L)N(J$_1$)(J$_2$);
L is O, S or NJ$_3$;
each J$_1$, J$_2$ and J$_3$ is, independently, H or C$_1$-C$_6$ alkyl; and
when j is 1 then Z is other than halogen or N(E$_2$)(E$_3$) and when A is O then G$_1$ is other than halogen.

In certain embodiments, Bx is uracil, 5-thiazolo-uracil, 2-thio-uracil, 5-propynyl-uracil, thymine, 2'-thio-thymine, cytosine, 5-methylcytosine, 5-thiazolo-cytosine, 5-propynyl-cytosine, adenine, guanine, 2,6-diaminopurine, 1H-pyrimido[5,4-b][1,4benzoxazin-2(3H)-one), 1H-pyrimido[5,4-b][1,4]benzothiazin-2(3H)-one, 9-(2-aminoethoxy)-H-pyrimido[5,4-b][1,4]benzoxazin-2(3H)-one, 2H-pyrimido[4,5-b]indol-2-one or H-pyrido[3',2':4,5]pyrrolo[2,3-d]pyrimidin-2-one. In certain embodiments, Bx is uracil, thymine, cytosine, 5-methylcytosine, adenine or guanine.

In certain embodiments, Q$_1$ is H. In certain embodiments, Q$_2$ is H. In certain embodiments, Q$_1$ and Q$_2$ are each other than H. In certain embodiments, Q$_1$ and Q$_2$ is substituted C$_1$-C$_6$ alkyl. In certain embodiments, the substituted C$_1$-C$_6$ alkyl comprises at least one substituent group selected from halogen, C$_2$-C$_6$ alkenyl, OJ$_1$, NJ$_1$J$_2$ and CN, wherein each J$_1$ and J$_2$ is, independently, H or C$_1$-C$_6$ alkyl. In certain embodiments, the substituted C$_1$-C$_6$ alkyl comprises at least one substituent group selected from fluoro and OCH$_3$.

In certain embodiments, at least one of Q$_1$ and Q$_2$ is C$_1$-C$_6$ alkyl. In certain embodiments, Q$_1$ is methyl. In certain embodiments, Q$_2$ is methyl.

In certain embodiments, G$_1$ is OCH$_3$, OCH$_2$F, OCHF$_2$, OCF$_3$, OCH$_2$CH$_3$, O(CH$_2$)$_2$F, OCH$_2$CHF$_2$, OCH$_2$CF$_3$, OCH$_2$—CH=CH$_2$, O(CH$_2$)$_2$—OCH$_3$, O(CH$_2$)$_2$—SCH$_3$, O(CH$_2$)$_2$OCF$_3$, O(CH$_2$)$_3$—N(R$_4$)(R$_5$), O(CH$_2$)$_2$—ON(R$_4$)(R$_5$), O(CH$_2$)$_2$—O(CH$_2$)$_2$—N(R$_4$)(R$_5$), OCH$_2$C(=O)—N(R$_4$)(R$_5$), OCH$_2$C(=O)—N(R$_6$)—(CH$_2$)$_2$—N(R$_4$)(R$_5$) or O(CH$_2$)$_2$—N(R$_6$)—C(=NR$_7$)[N(R$_4$)(R$_5$)] wherein R$_4$, R$_5$, R$_6$ and R$_7$ are each independently, H or C$_1$-C$_6$ alkyl. In certain embodiments, G$_1$ is OCH$_3$, OCF$_3$, OCH$_2$CH$_3$, OCH$_2$CF$_3$, OCH$_2$—CH=CH$_2$, O(CH$_2$)$_2$—OCH$_3$, O(CH$_2$)$_2$, O(CH$_2$)$_2$—N(CH$_3$)$_2$, OCH$_2$C(=O)—N(H)CH$_3$, OCH$_2$C(=O)—N(H)—(CH$_2$)$_2$—N(CH$_3$)$_2$ or OCH$_2$—N(H)—C(=NH)NH$_2$. In certain embodiments, G$_1$ is OCH$_3$, O(CH$_2$)$_2$—OCH$_3$, OCH$_2$C(=O)—N(H)CH$_3$ or OCH$_2$C (=O)—N(H)—(CH$_2$)$_2$—N(CH$_3$)$_2$. In certain embodiments, G$_1$ is O(CH$_2$)$_2$—OCH$_3$. In certain embodiments, G$_1$ is F.

In certain embodiments, at least one of T$_1$ and T$_2$ is a hydroxyl protecting group selected from benzyl, benzoyl, 2,6-dichlorobenzyl, t-butyldimethylsilyl, t-butyldiphenylsilyl, mesylate, tosylate, dimethoxytrityl (DMT), 9-phenylxanthine-9-yl (Pixyl) and 9-(p-methoxyphenyl)xanthine-9-yl (MOX). In certain embodiments, T$_1$ is selected from acetyl, benzyl, t-butyldimethylsilyl, t-butyldiphenylsilyl and dimethoxytrityl. In certain embodiments, T$_1$ is 4,4'-dimethoxytrityl.

In certain embodiments, T$_1$ is a phosphorus moiety. In certain embodiments, the phosphorus moiety In certain embodiments, the phosphorus moiety has the formula:

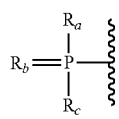

wherein:

R$_a$ and R$_c$ are each, independently, OH, SH, C$_1$-C$_6$ alkyl, substituted C$_1$-C$_6$ alkyl, C$_1$-C$_6$ alkoxy, substituted C$_1$-C$_6$ alkoxy, amino or substituted amino; and R$_b$ is O or S.

In certain embodiments, R$_a$ and R$_c$ are each OH. In certain embodiments, R$_a$ and R$_c$ are each OCH$_3$. In certain embodiments, R$_a$ and R$_c$ are each OCH$_2$CH$_3$. In certain embodiments, R$_b$ is O. In certain embodiments, R$_b$ is S.

In certain embodiments, R$_a$ is different than R$_c$. In certain embodiments, R$_a$ and R$_c$ are each other than OH.

In certain embodiments, T$_2$ is a reactive phosphorus group. In certain embodiments, T$_2$ is a reactive phosphorus group selected from diisopropylcyanoethoxy phosphoramidite and H-phosphonate. In certain embodiments, T$_1$ is 4,4'-dimethoxytrityl and T$_2$ is diisopropylcyanoethoxy phosphoramidite. In certain embodiments, T$_1$ is a phosphorus moiety and T$_2$ is diisopropylcyanoethoxy phosphoramidite.

In certain embodiments, A is O. In certain embodiments, A is S. In certain embodiments, A is N(R$_1$). In certain embodiments, R$_1$ is H or CH$_3$.

In certain embodiments, the compounds provided herein have the configuration of Formula Ia:

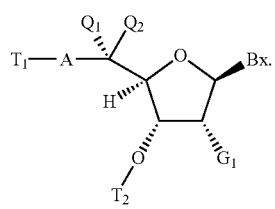

In certain embodiments; compounds are provided having Formula Ia wherein: Bx is a heterocyclic base moiety; A is O; T$_1$ is H or a protecting group; T$_2$ is H, a protecting group or a reactive phosphorus group; one of Q$_1$ and Q$_2$ is C$_1$-C$_6$ alkyl and the other of Q$_1$ and Q$_2$ is H; and G$_1$ is OCH$_3$, O(CH$_2$)$_2$—OCH$_3$, OCH$_2$C(=O)—N(H)CH$_3$ or OCH$_2$C(=O)—N(H)—(CH$_2$)$_2$—N(CH$_3$)$_2$. In certain embodiments; compounds are provided having Formula Ia wherein: Bx is a heterocyclic base moiety; A is O; T$_1$ is H or a protecting group; T$_2$ is H, a protecting group or a reactive phosphorus group; Q$_1$ is CH$_3$ and Q$_2$ is H, and G$_1$ is OCH$_3$, O(CH$_2$)$_2$—OCH$_3$, OCH$_2$C(=O)—N(H)CH$_3$ or OCH$_2$C(=O)—N(H)—(CH$_2$)$_2$—N(CH$_3$)$_2$. In certain embodiments; compounds are provided having Formula Ia wherein: Bx is a heterocyclic base moiety; A is O; T$_1$ is H or a protecting group; T$_2$ is H, a protecting group or a reactive phosphorus group; Q$_1$ is CH$_3$ and Q$_2$ is H, and G$_1$ is O(CH$_2$)$_2$—OCH$_3$.

In certain embodiments; compounds are provided having Formula Ia wherein: Bx is a heterocyclic base moiety; A is O; T$_1$ is H or a protecting group; T$_2$ is H, a protecting group or a reactive phosphorus group; Q$_2$ is CH$_3$ and Q$_1$ is H, and G$_1$ is OCH$_3$, O(CH$_2$)$_2$—OCH$_3$, OCH$_2$C(=O)—N(H)CH$_3$ or OCH$_2$C(=O)—N(H)—(CH$_2$)$_2$—N(CH$_3$)$_2$. In certain embodiments; compounds are provided having Formula Ia wherein: Bx is a heterocyclic base moiety; A is O; T$_1$ is H or a protecting group; T$_2$ is H, a protecting group or a reactive phosphorus group; Q$_2$ is CH$_3$ and Q$_2$ is H, and G$_1$ is O(CH$_2$)$_2$—OCH$_3$.

In certain embodiments, oligomeric compounds are provided comprising at least one monomer of Formula II:

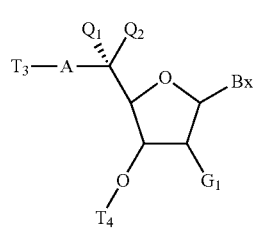

wherein independently for each monomer of Formula II:

Bx is a heterocyclic base moiety;

A is O, S or N(R$_1$);

R$_1$ is H, C$_1$-C$_6$ alkyl or substituted C$_1$-C$_6$ alkyl;

one of T$_3$ and T$_4$ is an internucleoside linking group linking the monomer to the oligomeric compound and the other of T$_3$ and T$_4$ is H, a protecting group, a phosphorus moiety, a 5' or 3'-terminal group or an internucleoside linking group linking the monomer to the oligomeric compound;

one of Q$_1$ and Q$_2$ is H, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl or substituted C$_2$-C$_6$ alkynyl and the other of Q$_1$ and Q$_2$ is C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl or substituted C$_2$-C$_6$ alkynyl;

G$_1$ is O—[C(R$_2$)(R$_3$)]$_n$—[(C=O)$_m$—X]$_j$—Z or halogen;

each R$_2$ and R$_3$ is, independently, H or halogen;

X is O, S or N(E$_1$);

Z is H, halogen, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl or N(E$_2$)(E$_3$);

E$_1$, E$_2$ and E$_3$ are each, independently, H, C$_1$-C$_6$ alkyl or substituted C$_1$-C$_6$ alkyl;

n is from 1 to about 6;

m is 0 or 1;

j is 0 or 1;

each substituted group comprises one or more optionally protected substituent groups independently selected from halogen, OJ$_1$, N(J$_1$)(J$_2$), =NJ$_1$, SJ$_1$, N$_3$, CN, OC(=L)J$_1$, OC(=L)N(J$_1$)(J$_2$) and C(=L)N(J$_1$)(J$_2$);

L is O, S or NJ$_3$;

each J$_1$, J$_2$ and J$_3$ is, independently, H or C$_1$-C$_6$ alkyl; and when j is 1 then Z is other than halogen or N(E$_2$)(E$_3$) and when A is O then G$_1$ is other than halogen.

In certain embodiments, each Bx is, independently, uracil, 5-thiazolo-uracil, 2-thio-uracil, 5-propynyl-uracil, thymine, 2'-thio-thymine, cytosine, 5-methylcytosine, 5-thiazolo-cytosine, 5-propynyl-cytosine, adenine, guanine, 2,6-diaminopurine, 1H-pyrimido[5,4-b][1,4benzoxazin-2(3H)-one), 1H-pyrimido[5,4-b][1,4]benzothiazin-2(3H)-one, 9-(2-aminoethoxy)-H-pyrimido[5,4-b][1,4]benzoaxin-2(3H)-one, 2H-pyrimido[4,5-b]indol-2-one or H-pyrido[3',2':4,5]pyrrolo[2,3-d]pyrimidin-2-one. In certain embodiments, each Bx is, independently, uracil, thymine, cytosine, 5-methylcytosine, adenine or guanine.

In certain embodiments, oligomeric compounds are provided comprising at least one monomer of Formula II, wherein for each monomer of Formula II $Q_1$ is H. In certain embodiments, each $Q_2$ is H. In certain embodiments, each $Q_1$ and each $Q_2$ are other than H. In certain embodiments, for each monomer of Formula II at least one of $Q_1$ and $Q_2$ is substituted $C_1$-$C_6$ alkyl. In certain embodiments, each substituted $C_1$-$C_6$ alkyl comprises at least one substituent group independently selected from halogen, $C_2$-$C_6$ alkenyl, $OJ_1$, $NJ_1J_2$ and CN, wherein each $J_1$ and $J_2$ is, independently, H or $C_1$-$C_6$ alkyl. In certain embodiments, each substituted $C_1$-$C_6$ alkyl comprises at least one substituent group independently selected from fluoro and $OCH_3$.

In certain embodiments, oligomeric compounds are provided comprising at least one monomer of Formula II, wherein for each monomer of Formula II at least one of $Q_1$ and $Q_2$ is $C_1$-$C_6$ alkyl. In certain embodiments, each monomer of Formula II $Q_1$ is methyl. In certain embodiments, each monomer of Formula II $Q_2$ is methyl.

In certain embodiments, oligomeric compounds are provided comprising at least one monomer of Formula II, wherein independently for each monomer of Formula II $G_1$ is $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—CH=$CH_2$, $O(CH_2)_2$—$OCH_3$, $O(CH_2)_2$—$SCH_3$, $O(CH_2)_2$—$OCF_3$, $O(CH_2)_3$—N$(R_4)(R_5)$, $O(CH_2)_2$—$ON(R_4)(R_5)$, $O(CH_2)_2$—$O(CH_2)_2$—N$(R_4)(R_5)$, $OCH_2C(=O)$—N$(R_4)(R_5)$, $OCH_2C(=O)$—N$(R_6)$—$(CH_2)_2$—N$(R_4)(R_5)$ or $O(CH_2)_2$—N$(R_6)$—C$(=NR_7)$[N$(R_4)(R_5)$] wherein $R_4$, $R_5$, $R_6$ and $R_7$ are each, independently, H or $C_1$-$C_6$ alkyl. In certain embodiments, each $G_1$ is independently, $OCH_3$, $OCF_3$, $OCH_2CH_3$, $OCH_2CF_3$, $OCH_2$—CH=$CH_2$, $O(CH_2)_2$—$OCH_3$, $O(CH_2)_2$—$O(CH_2)_2$—N$(CH_3)_2$, $OCH_2C(=O)N(H)CH_3$, $OCH_2C(=O)$—N(H)—$(CH_2)_2$—N$(CH_3)_2$ or $OCH_2$—N(H)—C$(=NH)NH_2$. In certain embodiments, each $G_1$ is independently, $G_1$ is $OCH_3$, $O(CH_2)_2$—$OCH_3$, $OCH_2C(=O)$—N(H)$CH_3$ or $OCH_2C(=O)$—N(H)—$(CH_2)_2$—N$(CH_3)_2$. In certain embodiments, each $G_1$ is independently, $G_1$ is $O(CH_2)_2$—$OCH_3$. In certain embodiments, each $G_1$ is F.

In certain embodiments, oligomeric compounds are provided comprising at least one monomer of Formula II, wherein at least one of $T_3$ and $T_4$ is a 5' or 3'-terminal group. In certain embodiments, oligomeric compounds are provided comprising at least one monomer of Formula II, wherein at least one of $T_3$ and $T_4$ is a conjugate group. In certain embodiments, oligomeric compounds are provided comprising one monomer of Formula II, wherein $T_3$ is a phosphorus moiety.

In certain embodiments, oligomeric compounds are provided comprising at least one monomer of Formula II, wherein one $T_2$ is a phosphorus moiety having the formula:

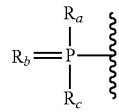

wherein:
$R_a$ and $R_c$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino; and
$R_b$ is O or S.

In certain embodiments, $R_a$ and $R_c$ are each OH. In certain embodiments, $R_a$ and $R_c$ are each $OCH_3$. In certain embodiments, $R_a$ and $R_c$ are each $OCH_2CH_3$. In certain embodiments, $R_b$ is O. In certain embodiments, $R_b$ is S.

In certain embodiments, $R_a$ is different than $R_c$. In certain embodiments, $R_a$ and $R_c$ are each other than OH.

In certain embodiments, oligomeric compounds are provided comprising at least one monomer of Formula II, wherein, each monomer of Formula II has the configuration of Formula IIa:

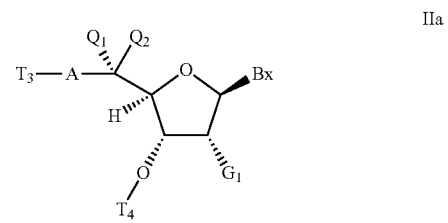

IIa

In certain embodiments, oligomeric compounds are provide having at least one monomer of Formula IIa wherein independently for each monomer of Formula IIa: Bx is a heterocyclic base moiety; A is O; one of $T_3$ and $T_4$ is an internucleoside linking group linking the monomer to the oligomeric compound and the other of $T_3$ and $T_4$ is H, a protecting group, a phosphorus moiety, a 5' or 3'-terminal group or an internucleoside linking group linking the monomer to the oligomeric compound; one of $Q_1$ and $Q_2$ is $CH_3$ and the other of $Q_1$ and $Q_2$ is H; and $G_1$ is $OCH_3$, $O(CH_2)_2$—$OCH_3$, $OCH_2C(=O)$—N(H)$CH_3$ or $OCH_2C(=O)$—N(H)—$(CH_2)_2$—N$(CH_3)_2$.

In certain embodiments, oligomeric compounds are provide having at least one monomer of Formula IIa wherein independently for each monomer of Formula IIa: Bx is a heterocyclic base moiety; A is O; one of $T_3$ and $T_4$ is an internucleoside linking group linking the monomer to the oligomeric compound and the other of $T_3$ and $T_4$ is H, a protecting group, a phosphorus moiety, a 5' or 3'-terminal group or an internucleoside linking group linking the monomer to the oligomeric compound; $Q_1$ is $CH_3$ and $Q_2$ is H and $G_1$ is $OCH_3$, $O(CH_2)_2$—$OCH_3$, $OCH_2C(=O)$—N(H)$CH_3$ or $OCH_2C(=O)$—N(H)—$(CH_2)_2$—N$(CH_3)_2$. $Q_1$ is $CH_3$ and $Q_2$ is H.

In certain embodiments, oligomeric compounds are provide having at least one monomer of Formula IIa wherein independently for each monomer of Formula IIa: Bx is a heterocyclic base moiety; A is O; one of $T_3$ and $T_4$ is an internucleoside linking group linking the monomer to the oligomeric compound and the other of $T_3$ and $T_4$ is H, a protecting group, a phosphorus moiety, a 5' or 3'-terminal group or an internucleoside linking group linking the monomer to the oligomeric compound; $Q_1$ is $CH_3$ and $Q_2$ is H and $G_1$ is $O(CH_2)_2$—$OCH_3$.

In certain embodiments, oligomeric compounds are provide having at least one monomer of Formula IIa wherein independently for each monomer of Formula IIa: Bx is a heterocyclic base moiety; A is O; one of $T_3$ and $T_4$ is an internucleoside linking group linking the monomer to the oligomeric compound and the other of $T_3$ and $T_4$ is H, a protecting group, a phosphorus moiety, a 5' or 3'-terminal group or an internucleoside linking group linking the monomer to the oligomeric compound; $Q_2$ is $CH_3$ and $Q_1$ is H and $G_1$ is $OCH_3$, $O(CH_2)_2$—$OCH_3$, $OCH_2C(=O)$—$N(H)CH_3$ or $OCH_2C(=O)$—$N(H)$—$(CH_2)_2$—$N(CH_3)_2$.

In certain embodiments, oligomeric compounds are provide having at least one monomer of Formula IIa wherein independently for each monomer of Formula IIa: Bx is a heterocyclic base moiety; A is O; one of $T_3$ and $T_4$ is an internucleoside linking group linking the monomer to the oligomeric compound and the other of $T_3$ and $T_4$ is H, a protecting group, a phosphorus moiety, a 5' or 3'-terminal group or an internucleoside linking group linking the monomer to the oligomeric compound; $Q_2$ is $CH_3$ and $Q_1$ is H and $G_1$ is $O(CH_2)_2$—$OCH_3$.

In certain embodiments, oligomeric compounds are provided comprising one monomer of Formula II at the 5' end.

In certain embodiments, oligomeric compounds are provided comprising at least one region having at least 2 contiguous monomers of Formula II. In certain embodiments, the at least one region comprises from 2 to 5 contiguous monomers of Formula II.

In certain embodiments, oligomeric compounds are provided comprising at least two regions wherein each region independently comprises from 1 to about 5 contiguous monomers of Formula II and wherein each region is separated by at least one monomer subunit that is different from the monomers having Formula II and independently selected from nucleosides and modified nucleosides. In certain embodiments, gapped oligomeric compounds are provided comprising one region of contiguous monomers of Formula II is located at the 5'-end and a second region of contiguous monomers of Formula II is located at the 3'-end, wherein the two regions are separated by an internal region comprising from about 6 to about 18 monomer subunits independently selected from nucleosides and modified nucleosides that are different from the monomers having Formula II. In certain embodiments, the internal region comprises from about 8 to about 14 contiguous β-D-2'-deoxyribofuranosyl nucleosides. In certain embodiments, the internal region comprises from about 9 to about 12 contiguous β-D-2'-deoxyribofuranosyl nucleosides.

In certain embodiments, oligomeric compounds are provided comprising one region of from 2 to 3 contiguous monomers of Formula II, an optional second region of from 1 to 3 contiguous monomers of Formula II and a third region of from 8 to 14 β-D-2'-deoxyribofuranosyl nucleosides wherein said third region is located between said first and said second regions.

In certain embodiments, oligomeric compounds are provided wherein each internucleoside linking group is, independently, a phosphodiester internucleoside linking group or a phosphorothioate internucleoside linking group. In certain embodiments, oligomeric compounds are provided wherein essentially each internucleoside linking group is a phosphorothioate internucleoside linking group.

In certain embodiments, double stranded compositions are provided comprising a first oligomeric compound and a second oligomeric compound wherein the first oligomeric compound is complementary to the second oligomeric compound and the second oligomeric compound is complementary to a nucleic acid target and at least one of the first and second oligomeric compounds is an oligomeric compound as provided herein and wherein said composition optionally comprise one or more 5' or 3' terminal groups.

In certain embodiments, methods are provided herein comprising contacting a cell with an oligomeric compound or a double stranded composition as provided herein, wherein the oligomeric compound or one strand of the double stranded composition is complementary to a target RNA. In certain embodiments, the cell is in an animal. In certain embodiments, the cell is in a human. In certain embodiments, the target RNA is selected from mRNA, pre-mRNA, micro RNA and other non-coding RNA. In certain embodiments, the target RNA is mRNA. In certain embodiments, the target RNA is human mRNA. In certain embodiments, the target RNA is cleaved thereby inhibiting its function. In certain embodiments, the methods further comprise evaluating the antisense activity of the oligomeric compound or the double stranded composition on said cell. In certain embodiments, the evaluating comprises detecting the levels of target RNA. In certain embodiments, the evaluating comprises detecting the levels of a protein. In certain embodiments, the evaluating comprises detection of one or more phenotypic effects.

In certain embodiments, the oligomeric compound and the double stranded compositions are provided for use in therapy. In certain embodiments the therapy comprises treating a disease characterized by undesired gene expression. In certain embodiments, the therapy is treating a disease by inhibiting gene expression. In certain embodiments, the therapy involves the modulation of non-coding RNAs (reducing or increasing) which in turn affect the expression of other genes which are involved in creating a diseased state. In certain embodiments, the therapy comprises contacting a cell in an animal with an oligomeric compound or the double stranded composition as provided herein.

In certain embodiments, the oligomeric compounds and double stranded compositions are provided for the manufacture of a medicament for the treatment of a disease characterized by undesired gene expression.

In certain embodiments, the oligomeric compounds and double stranded compositions are provided for the manufacture of a medicament for treating a disease by inhibiting gene expression.

In certain embodiments, pharmaceutical compositions are provided comprising an oligomeric compound or a double stranded composition as provided herein and a pharmaceutically acceptable carrier.

In certain embodiments, compounds are provided having Formula III:

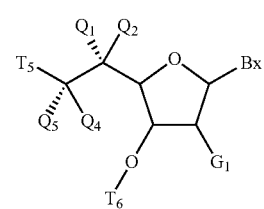

III wherein:
Bx is a heterocyclic base moiety;
$T_5$ is a phosphorus moiety or a reactive phosphorus group;
$T_6$ is H, a protecting group or a reactive phosphorus group;

$Q_1$, $Q_2$, $Q_3$ and $Q_4$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$G_1$ is O—$[C(R_2)(R_3)]_n$—$[(C=O)_m$—$X]_j$—Z or halogen;

each $R_2$ and $R_3$ is, independently, H or halogen;

X is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkyl; $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=L)J_1$, $OC(=L)N(J_1)(J_2)$ and $C(=L)N(J_1)(J_2)$;

L is O, S or $NJ_3$;

each $J_1$, $J_2$ and $J_3$ is, independently, H or $C_1$-$C_6$ alkyl;

when j is 1 then Z is other than halogen or $N(E_2)(E_3)$; and when $Q_1$, $Q_2$, $Q_3$ and $Q_4$ are each H or when $Q_1$ and $Q_2$ are H and $Q_3$ and $Q_4$ are each F or when $Q_1$ and $Q_2$ are each H and one of $Q_3$ and $Q_4$ is H and the other of Q and $Q_4$ is $R_9$ then $G_1$ is other than H, hydroxyl, $OR_9$, halogen, $CF_3$, $CCl_3$, $CHCl_2$ and $CH_2OH$ wherein $R_9$ is alkyl, alkenyl, alkynyl, aryl In certain embodiments, Bx is uracil, 5-thiazolo-uracil, 2-thio-uracil, 5-propynyl-uracil, thymine, 2'-thio-thymine, cytosine, 5-methylcytosine, 5-thiazolo-cytosine, 5-propynyl-cytosine, adenine, guanine, 2,6-diaminopurine, 1H-pyrimido[5,4-b][1,4benzoxazin-2(3H)-one), 1H-pyrimido[5,4-b][1,4] benzothiazin-2-(3H)-one, one, 9-(2-aminoethoxy)-H-pyrimido[5,4-b][1,4]benzoxazin-2(3H)-one, 2H-pyrimido[4,5-b]indol-2-one or H-pyrido[3',2':4,5]pyrrolo[2,3-d]pyrimidin-2-one. In certain embodiments, Bx is uracil, thymine, cytosine, 5-methylcytosine, adenine or guanine.

In certain embodiments, $G_1$ is $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—CH=$CH_2$, $O(CH_2)_2$—$OCH_3$, $O(CH_2)_2$—$SCH_3$, $O(CH_2)_2$—$OCF_3$, $O(CH_2)_3$—$N(R_4)(R_5)$, $O(CH_2)_2$—ON $(R_4)(R_5)$, $O(CH_2)_2$—$O(CH_2)_2$—$N(R_4)(R_5)$, $OCH_2C$ $(=O)$—$N(R_4)(R_5)$, $OCH_2C(=O)$—$N(R_6)$—$(CH_2)_2$—N $(R_4)(R_5)$ or $O(CH_2)_2$—$N(R_6)$—$C(=NR_7)[N(R_4)(R_5)]$ wherein $R_4$, $R_5$, $R_6$ and $R_7$ are each, independently, H or $C_1$-$C_6$ alkyl. In certain embodiments, $G_1$ is $OCH_3$, $OCF_3$, $OCH_2CH_3$, $OCH_2CF_3$, $OCH_2$—CH=$CH_2$, $O(CH_2)_2$—$OCH_3$, $O(CH_2)_2$—$O(CH_2)_2$—$N(CH_3)_2$, $OCH_2C(=O)$—N $(H)CH_3$, $OCH_2C(=O)$—$N(H)$—$(CH_2)_2$—$N(CH_3)_2$ or $OCH_2$—$N(H)$—$C(=NH)NH_2$. In certain embodiments, $G_1$ is $OCH_3$, $O(CH_2)_2$—$OCH_3$, $OCH_2C(=O)$—$N(H)CH_3$ or $OCH_2C(=O)$—$N(H)$—$(CH_2)_2$—$N(CH_3)_2$. In certain embodiments, $G_1$ is F.

In certain embodiments, $T_5$ is a phosphorus moiety. In certain embodiments, the phosphorus moiety has the formula:

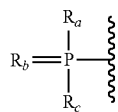

wherein:

$R_a$ and $R_c$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino; and $R_b$ is O or S.

In certain embodiments, $R_a$ and $R_c$ are each OH. In certain embodiments, $R_a$ and $R_c$ are each $OCH_3$. In certain embodiments, $R_a$ and $R_c$ are each $OCH_2CH_3$. In certain embodiments, $R_b$ is O. In certain embodiments, $R_b$ is S.

In certain embodiments, $R_a$ is different than $R_c$. In certain embodiments, $R_a$ and $R_c$ are each other than OH.

In certain embodiments, $T_5$ is an reactive phosphorus group. In certain embodiments, $T_6$ is selected from acetyl, benzyl, t-butyldimethylsilyl, t-butyldiphenylsilyl and dimethoxytrityl. In certain embodiments, $T_6$ is 4,4'-dimethoxytrityl. In certain embodiments, $T_6$ is a reactive phosphorus group. In certain embodiments, $T_6$ is a reactive phosphorus group selected from diisopropylcyanoethoxy phosphoramidite and H-phosphonate. In certain embodiments, $T_5$ is a phosphorus moiety and $T_6$ is diisopropylcyanoethoxy phosphoramidite.

In certain embodiments, the phosphorus moiety is —$P(OH)_2(=O)$.

In certain embodiments, one of $Q_1$, $Q_2$, $Q_3$ and $Q_4$ is substituted $C_1$-$C_6$ alkyl. In certain embodiments, $Q_1$, $Q_2$, $Q_3$ and $Q_4$ are H. In certain embodiments, the substituted $C_1$-$C_6$ alkyl comprises at least one substituent group selected from halogen, $C_2$-$C_6$ alkenyl, $OJ_1$, $NJ_1J_2$ and CN, wherein each $J_1$ and independently, H or $C_1$-$C_6$ alkyl. In certain embodiments, the substituted $C_1$-$C_6$ alkyl comprises at least one substituent group selected from fluoro and $OCH_3$.

In certain embodiments, one of $Q_1$, $Q_2$, $Q_3$ and $Q_4$ is $C_1$-$C_6$ alkyl. In certain embodiments, one of $Q_1$ and $Q_2$ is $C_1$-$C_6$ alkyl. In certain embodiments, $Q_3$ and $Q_4$ is $C_1$-$C_6$ alkyl. In certain embodiments, the $C_1$-$C_6$ alkyl is methyl. In certain embodiments, the other three of $Q_1$, $Q_2$, $Q_3$ and $Q_4$ are H. In certain embodiments, one of $Q_1$, $Q_2$, $Q_3$ and $Q_4$ is F. In certain embodiments, two of $Q_1$, $Q_2$, $Q_3$ and $Q_4$ are F. In certain embodiments, $Q_1$ and $Q_2$ are each F. In certain embodiments, $Q_3$ and $Q_4$ are each F. In certain embodiments, each of $Q_1$, $Q_2$, $Q_3$ and $Q_4$ is F or H.

In certain embodiments, compounds are provided having the configuration:

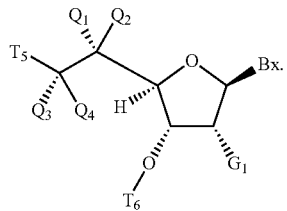

In certain embodiments, oligomeric compounds are provided comprising at least one monomer of Formula IV:

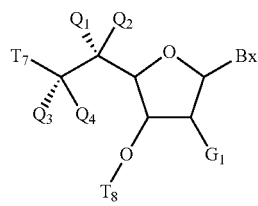

wherein independently for each monomer of Formula IV:

Bx is a heterocyclic base moiety;

one of $T_7$ and $T_8$ is an internucleoside linking group linking the monomer to the oligomeric compound and the other of $T_7$ and $T_8$ is H, a hydroxyl protecting group, a phosphorus moiety, a 5' or 3'-terminal group or an internucleoside linking group linking the monomer to the oligomeric compound;

$Q_1$, $Q_2$, $Q_3$ and $Q_4$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$G_1$ is O—[C($R_2$)($R_3$)]$_n$—[(C=O)$_m$—X]$_j$—Z or halogen;

each $R_2$ and $R_3$ is, independently, H or halogen;

X is O, S or N($E_1$);

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or N($E_2$)($E_3$);

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, OC(=L)$J_1$, OC(=L)N($J_1$)($J_2$) and C(=L)N($J_1$)($J_2$);

L is O, S or $NJ_3$;

each $J_1$, $J_2$ and $J_3$ is, independently, H or $C_1$-$C_6$ alkyl;

when j is 1 then Z is other than halogen or N($E_2$)($E_3$); and when $Q_1$, $Q_2$, $Q_3$ and $Q_4$ are each H or when $Q_1$ and $Q_2$ are H and $Q_3$ and $Q_4$ are each F or when $Q_1$ and $Q_2$ are each H and one of $Q_3$ and $Q_4$ is H and the other of $Q_3$ and $Q_4$ is $R_9$ then $G_1$ is other than H, hydroxyl, $OR_9$, halogen, $CF_3$, $CCl_3$, $CHCl_2$ and $CH_2OH$ wherein $R_9$ is alkyl, alkenyl, alkynyl, aryl or alkaryl.

In certain embodiments, oligomeric compounds are provided comprising at least one monomer of Formula IV, wherein each Bx is, independently, uracil, 5-thiazolo-uracil, 2-thio-uracil, 5-propynyl-uracil, thymine, 2'-thio-thymine, cytosine, 5-methylcytosine, 5-thiazolo-cytosine, 5-propynyl-cytosine, adenine, guanine, 2,6-diaminopurine, 1H-pyrimido[5,4-b][1,4benzoxazin-2(3H)-one), 1H-pyrimido[5,4-b][1,4]benzothiazin-2(3H)-one, 9-(2-aminoethoxy)-H-pyrimido[5,4-b][1,4]benzoxazin-2(3H)-one, 2H-pyrimido[4,5-b]indol-2-one or H-pyrido[3',2':4,5]pyrrolo[2,3-d]pyrimidin-2-one. In certain embodiments, each Bx is, independently, uracil, thymine, cytosine, 5-methylcytosine, adenine or guanine.

In certain embodiments, oligomeric compounds are provided comprising at least one monomer of Formula IV, wherein independently for each monomer of Formula IV, $G_1$ is $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—CH=$CH_2$, $O(CH_2)_2$—$OCH_3$, $O(CH_2)_2$—$SCH_3$, $O(CH_2)_2$—$OCF_3$, $O(CH_2)_3$—N($R_4$)($R_5$), $O(CH_2)_2$—ON($R_4$)($R_5$), $O(CH_2$—O($CH_2)_2$—N($R_4$)($R_4$), $OCH_2C$(=O)—N($R_4$)($R_5$), $OCH_2C$(=O)—N($R_6$)—($CH_2)_2$—N($R_4$)($R_5$) or $O(CH_2)_2$—N($R_6$)—C(=$NR_7$)[N($R_4$)($R_5$)] wherein $R_4$, $R_5$, $R_6$ and $R_7$ are each, independently, H or $C_1$-$C_6$ alkyl. In certain embodiments, independently for each monomer of Formula IV, $G_1$ is $OCH_3$, $OCF_3$, $OCH_2CH_3$, $OCH_2CF_3$, $OCH_2$—CH=$CH_2$, $O(CH_2)_2$—$OCH_3$, $O(CH_2)_2$—$O(CH_2)_2$—N($CH_3$)$_2$, $OCH_2C$(=O)—N(H)$CH_3$, $OCH_2C$(=O)—N(H)—($CH_2)_2$—N($CH_3$)$_2$ or $OCH_2$—N(H)—C(=NH)$NH_2$. In certain embodiments, independently for each monomer of Formula IV, $G_1$ is $OCH_3$, $O(CH_2)_2$—$OCH_3$, $OCH_2C$(=O)—N(H)$CH_3$ or $OCH_2C$(=O)—N(H)—($CH_2)_2$—N($CH_3$)$_2$. In certain embodiments, for each monomer of Formula IV $G_1$ is F.

In certain embodiments, one $T_8$ is a 3'-terminal group. In certain embodiments, at least one of $T_7$ and $T_8$ is a conjugate group. In certain embodiments, one $T_7$ is a phosphorus moiety. In certain embodiments, the phosphorus moiety has the formula:

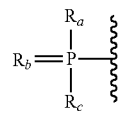

wherein:

$R_a$ and $R_c$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino; and $R_b$ is O or S.

In certain embodiments, $R_a$ and $R_c$ are each OH. In certain embodiments, $R_a$ and $R_c$ are each $OCH_3$. In certain embodiments, $R_a$ and $R_c$ are each $OCH_2CH_3$. In certain embodiments, $R_b$ is O. In certain embodiments, $R_b$ is S.

In certain embodiments, $R_a$ is different than $R_c$. In certain embodiments, $R_a$ and $R_b$ are each other than OH.

In certain embodiments, one of $Q_1$, $Q_2$, $Q_3$ and $Q_4$ is substituted $C_1$-$C_6$ alky for each monomer of Formula IV. In certain embodiments, one of $Q_1$, $Q_2$, $Q_3$ and $Q_4$ is substituted $C_1$-$C_6$ alkyl and the other three of $Q_1$, $Q_2$, $Q_3$ and $Q_4$ are H for each monomer of Formula IV. In certain embodiments, one of $Q_1$, $Q_2$, $Q_3$ and $Q_4$ is substituted $C_1$-$C_6$ alkyl and the other three of $Q_1$, $Q_2$, $Q_3$ and $Q_4$ are H for each monomer of Formula IV. In certain embodiments, the substituted $C_1$-$C_6$ alkyl comprises at least one substituent group selected from halogen, $C_2$-$C_6$ alkenyl, $OJ_1$, $NJ_1J_2$ and CN, wherein each $J_1$ and $J_2$ is, independently, H or $C_1$-$C_6$ alkyl. In certain embodiments, the substituted $C_1$-$C_6$ alkyl comprises at least one substituent group selected from fluoro and $OCH_3$.

In certain embodiments, one of $Q_1$, $Q_2$, $Q_3$ and $Q_4$ is $C_1$-$C_6$ alkyl for each monomer of Formula IV. In certain embodiments, one of $Q_1$ and $Q_2$ is $C_1$-$C_6$ alkyl for each monomer of Formula IV. In certain embodiments, one of $Q_3$ and $Q_4$ is $C_1$-$C_6$ alkyl for each monomer of Formula IV. In certain embodiments, the $C_1$-$C_6$ alkyl group is methyl.

In certain embodiments, three of $Q_1$, $Q_2$, $Q_3$ and $Q_4$ are H for each monomer of Formula IV. In certain embodiments, one of $Q_1$, $Q_2$, $Q_3$ and $Q_4$ is F for each monomer of Formula IV. In certain embodiments, two of $Q_1$, $Q_2$, $Q_3$ and $Q_4$ are F for each monomer of Formula IV. In certain embodiments, $Q_1$ and $Q_2$ are each F for each monomer of Formula IV. In certain embodiments, $Q_3$ and $Q_4$ are each F for each monomer of Formula IV. In certain embodiments, $Q_1$, $Q_2$, $Q_3$ and $Q_4$ are each F or H for each monomer of Formula IV.

In certain embodiments, oligomeric compounds are provided comprising at least one monomer of Formula IV, wherein each monomer of Formula IV has the configuration:

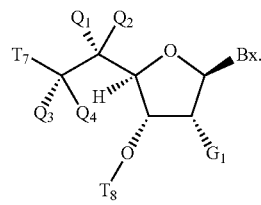

In certain embodiments, oligomeric compounds are provided comprising one monomer of Formula IV at the 5' end.

In certain embodiments, oligomeric compounds are provided comprising at least one region having at least 2 contiguous monomers of Formula IV. In certain embodiments, the at least one region comprises from 2 to 5 contiguous monomers of Formula IV.

In certain embodiments, oligomeric compounds are provided comprising at least two regions wherein each region independently comprises from 1 to about 5 contiguous monomers of Formula IV and wherein each region is separated by at least one monomer subunit that is different from the monomers having Formula IV and independently selected from nucleosides and modified nucleosides. In certain embodiments, gapped oligomeric compounds are provided comprising
one region of contiguous monomers of Formula IV is located at the 5'-end and a second region of contiguous monomers of Formula IV is located at the 3'-end, wherein the two regions are separated by an internal region comprising from about 6 to about 18 monomer subunits independently selected from nucleosides and modified nucleosides that are different from the monomers having Formula IV. In certain embodiments, the internal region comprises from about 8 to about 14 contiguous β-D-2'-deoxyribofuranosyl nucleosides. In certain embodiments, the internal region comprises from about 9 to about 12 contiguous β-D-2'-deoxyribofuranosyl nucleosides.

In certain embodiments, oligomeric compounds are provided comprising one region of from 2 to 3 contiguous monomers of Formula IV, an optional second region of from 1 to 3 contiguous monomers of Formula IV and a third region of from 8 to 14β-D-2'-deoxyribofuranosyl nucleosides wherein said third region is located between said first and said second regions.

In certain embodiments, oligomeric compounds are provided wherein each internucleoside linking group is, independently, a phosphodiester internucleoside linking group or a phosphorothioate internucleoside linking group. In certain embodiments, oligomeric compounds are provided wherein essentially each internucleoside linking group is a phosphorothioate internucleoside linking group.

In certain embodiments, double stranded compositions are provided comprising a first oligomeric compound and a second oligomeric compound wherein the first oligomeric compound is complementary to the second oligomeric compound and the second oligomeric compound is complementary to a nucleic acid target and at least one of the first and second oligomeric compounds is an oligomeric compound as provided herein and wherein said composition optionally comprise one or more 5' or 3' terminal groups.

In certain embodiments, methods are provided herein comprising contacting a cell with an oligomeric compound or a double stranded composition as provided herein, wherein the oligomeric compound or one strand of the double stranded composition is complementary to a target RNA. In certain embodiments, the cell is in an animal. In certain embodiments, the cell is in a human. In certain embodiments, the target RNA is selected from mRNA, pre-mRNA and micro RNA. In certain embodiments, the target RNA is mRNA. In certain embodiments, the target RNA is human mRNA. In certain embodiments, the target RNA is cleaved thereby inhibiting its function. In certain embodiments, the methods further comprise evaluating the antisense activity of the oligomeric compound or the double stranded composition on said cell. In certain embodiments, the evaluating comprises detecting the levels of target RNA. In certain embodiments, the evaluating comprises detecting the levels of a protein. In certain embodiments, the evaluating comprises detection of one or more phenotypic effects.

In certain embodiments, the oligomeric compound and the double stranded compositions are provided for use in therapy. In certain embodiments the therapy comprises treating a disease characterized by undesired gene expression. In certain embodiments, the therapy is treating a disease by inhibiting gene expression. In certain embodiments, the therapy involves the modulation of non-coding RNAs (reducing or increasing) which in turn affect the expression of other genes which are involved in creating a diseased state. In certain embodiments, the therapy comprises contacting a cell in an animal with an oligomeric compound or the double stranded composition as provided herein.

In certain embodiments, the oligomeric compounds and double stranded compositions are provided for the manufacture of a medicament for the treatment of a disease characterized by undesired gene expression.

In certain embodiments, the oligomeric compounds and double stranded compositions are provided for the manufacture of a medicament for treating a disease by inhibiting gene expression.

In certain embodiments, pharmaceutical compositions are provided comprising an oligomeric compound or a double stranded composition as provided herein and a pharmaceutically acceptable carrier.

Provided herein are compounds having Formula I:

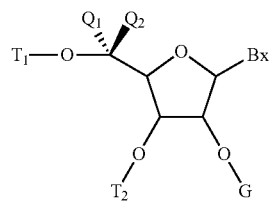

wherein:
Bx is a heterocyclic base moiety;
one of $T_1$ and $T_2$ is H or a hydroxyl protecting group and the other of $T_1$ and $T_2$ is H, a hydroxyl protecting group or a reactive phosphorus group;
one of $Q_1$ and $Q_2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl and the other of $Q_1$ and $Q_2$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
G is $[C(R_1)(R_2)]_n$—$[(C=O)_m$—$X]_j$—Z;
each $R_1$ and $R_2$ is, independently, H or halogen;
X is O, S or $N(E_1)$;
Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_1)(E_2)$;
$E_1$ and $E_2$ are each, independently, H, $C_1$-$C_6$ alkyl or substituted $C_1$-$C_6$ alkyl;
n is from 1 to about 6;
m is 0 or 1;
j is 0 or 1;
wherein each substituted group comprises one or more optionally protected substituent groups independently selected from halogen, $OJ_1$, $N(J_1)(J_2)$, =$NJ_1$, $SJ_1$, $N_3$, CN, $OC(=L)J_1$, $OC(=L)N(J_1)(J_2)$ and $C(=L)N(J_1)(J_2)$, wherein each $J_1$, $J_2$ and $J_3$ is, independently, H or $C_1$-$C_6$ alkyl, and L is O, S or $NJ_3$; and
when j is 1 then Z is other than halogen or $N(E_2)(E_3)$.

In certain embodiments, Bx is uracil, 5-methyluracil, 5-thiazolo-uracil, 2-thio-uracil, 5-propynyl-uracil, thymine, 2'-thio-thymine, cytosine, 5-methylcytosine, 5-thiazolo-cytosine, 5-propynyl-cytosine, adenine, guanine, 2,6-diaminopurine, 1H-pyrimido[5,4-b][1,4benzoxazin-2(3H)-one), 1H-pyrimido[5,4]-b][1,4]benzothiazin-2(3H)-one, 9-(2-aminoethoxy)-H-pyrimido[5,4-b][1,4]benzoxazin-2(3H)-one, 2H-pyrimido[4,5-b]indol-2-one or H-pyrido[3',2':4,5]pyrrolo[2,3-d]pyrimidin-2-one. In certain embodiments, Bx is uracil, 5-methyluracil, thymine, cytosine, 5-methylcytosine, adenine or guanine.

In certain embodiments, at least one of $T_1$ and $T_2$ is a hydroxyl protecting group selected from benzyl, benzoyl, 2,6-dichlorobenzyl, t-butyldimethylsilyl, t-butyldiphenylsilyl, mesylate, tosylate, dimethoxytrityl (DMT), 9-phenylxanthine-9-yl (Pixyl) and 9-(p-methoxyphenyl)xanthine-9-yl (MOX). In certain embodiments, $T_1$ is selected from acetyl, benzyl, t-butyldimethylsilyl, t-butyldiphenylsilyl and dimethoxytrityl. In certain embodiments, $T_1$ is 4,4'-dimethoxytrityl. In certain embodiments, $T_2$ is a reactive phosphorus group. In certain embodiments, $T_2$ is a reactive phosphorus group selected from diisopropylcyanoethoxy phosphoramidite and H-phosphonate. In certain embodiments, $T_1$ is 4,4'-dimethoxytrityl and $T_2$ is diisopropylcyanoethoxy phosphoramidite.

In certain embodiments, $Q_1$ is H. In certain embodiments, $Q_2$ is H. In certain embodiments, $Q_1$ and $Q_2$ are each other than H. In certain embodiments, one of $Q_1$ and $Q_2$ is substituted $C_1$-$C_6$ alkyl. In certain embodiments, the substituted $C_1$-$C_6$ alkyl comprises at least one substituent group selected from halogen, $C_2$-$C_6$ alkenyl, $OJ_1$, $NJ_1J_2$ and CN, wherein each $J_1$ and $J_2$ is, independently, H or $C_1$-$C_6$ alkyl. In certain embodiments, the substituted $C_1$-$C_6$ alkyl comprises at least one substituent group selected from fluoro and $OCH_3$. In certain embodiments, $Q_1$ and $Q_2$ is $C_1$-$C_6$ alkyl. In certain embodiments, at least one of $Q_1$ and $Q_2$ is methyl.

In certain embodiments, G is $CH_3$, $CH_2F$, $CHF_2$, $CF_3$, $CH_2CH_3$, $CH_2CH_2F$, $CH_2CHF_2$, $CH_2CF_3$, $CH_2$—$CH$=$CH_2$, $(CH_2)_2$—O—$CH_3$, $(CH_2)_2$—S—$CH_3$, $(CH_2)_2$—O—$CF_3$, $(CH_2)_3$—$N(A_1)(A_2)$, $(CH_2)_2$—O—$N(A_1)(A_2)$, $(CH_2)_2$—O—$(CH_2)_2$—$N(A_1)(A_2)$, $CH_2C$(=O)—$N(A_1)(A_2)$, $CH_2C$(=O)—$N(A_3)$-$(CH_2)_2$—$N(A_1)(A_2)$ or $CH_2$—$N(A_3)$-C(=$NA_4$)[$N(A_1)(A_2)$] wherein $A_1$, $A_2$, $A_3$ and $A_4$ are each, independently, H or $C_1$-$C_6$ alkyl. In certain embodiments, G is $CH_3$, $CF_3$, $CH_2CH_3$, $CH_2CF_3$, $CH_2$—$CH$=$CH_2$, $(CH_2)_2$—O—$CH_3$, $(CH_2)_2$—O—$(CH_2)_2$—$N(CH_3)_2$, $CH_2C$(=O)N(H)$CH_3$, $CH_2C$(=O)—N(H)—$(CH_2)_2$—$N(CH_3)_2$ or $CH_2$—N(H)—C(=NH)$NH_2$. In certain embodiments, G is $CH_3$, $CH_2CH_2$—O—$CH_3$, $CH_2C$(=O)N(H)$CH_3$ or $CH_2C$(=O)—N(H)—$(CH_2)_2$—$N(CH_3)_2$.

In certain embodiments, the compounds provided herein have the configuration:

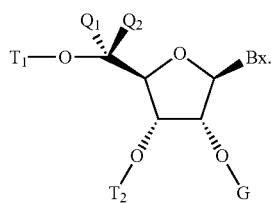

Also provided herein are oligomeric compounds, wherein each oligomeric compound comprises at least one monomer of Formula II:

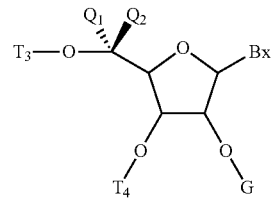

wherein independently for each monomer of Formula II:
Bx is a heterocyclic base moiety;
one of $T_3$ and $T_4$ is an internucleoside linking group linking the monomer to the oligomeric compound and the other of $T_3$ and $T_4$ is H, a hydroxyl protecting group, a 5' or 3'-terminal group or an internucleoside linking group linking the monomer to the oligomeric compound;
one of $Q_1$ and $Q_2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl and the other of $Q_1$ and $Q_2$ is $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
G is $[C(R_1)(R_2)]_n$—$[(C=O)_m$—$X]_j$—Z;
each $R_1$ and $R_2$ is, independently, H or halogen;
X is O, S or $N(E_1)$;
Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_1)(E_2)$;
$E_1$ and $E_2$ are each, independently, H, $C_1$-$C_6$ alkyl or substituted $C_1$-$C_6$ alkyl;
n is from 1 to about 6;
m is 0 or 1;
j is 0 or 1;
wherein each substituted group comprises one or more optionally protected substituent groups independently selected from halogen, $OJ_1$, $N(J_1)(J_2)$, =$NJ_1$, $SJ_1$, $N_3$, CN, $OC(=L)J_1$, $OC(=L)N(J_1)(J_2)$ and $C(=L)N(J_1)(J_2)$, wherein each $J_1$, $J_2$ and $J_3$ is, independently, H or $C_1$-$C_6$ alkyl, and L is O, S or $NJ_3$; and
when j is 1 then Z is other than halogen or $N(E_2)(E_3)$.

In certain embodiments, each Bx is, independently, uracil, 5-methyluracil, 5-thiazolo-uracil, 2-thio-uracil, 5-propynyl-uracil, thymine, 2'-thio-thymine, cytosine, 5-methylcytosine, 5-thiazolo-cytosine, 5-propynyl-cytosine, adenine, guanine, 2,6-diaminopurine, 1H-pyrimido[5,4-b][1,4benzoxazin-2(3H)-one), 1H-pyrimido[5,4-b][1,4]benzothiazin-2(3H)-one, 9-(2-aminoethoxy)-H-pyrimido[5,4-b][1,4]benzoxazin-2(3H)-one, 2H-pyrimido[4,5-b]indol-2-one or H-pyrido[3',2':4,5]pyrrolo[2,3-d]pyrimidin-2-one. In certain embodiments, each Bx is, independently, uracil, 5-methyluracil, thymine, cytosine, 5-methylcytosine, adenine or guanine.

In certain embodiments, at least one of $T_3$ and $T_4$ is a 5' or 3'-terminal group. In certain embodiments, at least one of $T_3$ and $T_4$ is a conjugate group or a phosphate moiety.

In certain embodiments, each $Q_1$ is H. In certain embodiments, each $Q_2$ is H. In certain embodiments, each $Q_1$ and each $Q_2$ are other than H. In certain embodiments, at least one of $Q_1$ and $Q_2$ is substituted $C_1$-$C_6$ alkyl for each monomer of Formula II. In certain embodiments, each substituted $C_1$-$C_6$ alkyl comprises at least one substituent group selected from halogen, $C_2$-$C_6$ alkenyl, $OJ_1$, $NJ_1J_2$ and CN, wherein each $J_1$ and $J_2$ is, independently, H or $C_1$-$C_6$ alkyl. In certain embodiments, each substituted $C_1$-$C_6$ alkyl comprises at least one substituent group selected from fluoro and $OCH_3$. In certain embodiments, at least one of $Q_1$ and $Q_2$ is $C_1$-$C_6$ alkyl for each monomer of Formula II. In certain embodiments, at least one of $Q_1$ and $Q_2$ is methyl for each monomer of Formula II.

In certain embodiments, G is $CH_3$, $CH_2F$, $CHF_2$, $CF_3$, $CH_2CH_3$, $CH_2CH_2F$, $CH_2CHF_2$, $CH_2CF_3$, $CH_2$—$CH=CH_2$, $(CH_2)_2$—O—$CH_3$, $(CH_2)_2$—S—$CH_3$, $(CH_2)_2$—O—$CF_3$, $(CH_2)_3$—$N(A_1)(A_2)$, $(CH_2)_2$—O—$N(A_1)(A_2)$, $(CH_2)_2$—O—$(CH_2)_2$—$N(A_1)(A_2)$, $CH_2C(=O)$—$N(A_1)(A_2)$, $CH_2C(=O)$—$N(A_3)$-$(CH_2)_2$—$N(A_1)(A_2)$ or $CH_2$—$N(A_3)$-$C(=NA_4)[N(A_1)(A_2)]$ wherein $A_1$, $A_2$, $A_3$ and $A_4$ are each, independently, H or $C_1$-$C_6$ alkyl for each monomer of Formula II. In certain embodiments, G is $CH_3$, $CF_3$, $CH_2CH_3$, $CH_2CF_3$, $CH_2$—$CH=CH_2$, $(CH_2)_2$—O—$CH_3$, $(CH_2)_2$—O—$(CH_2)_2$—$N(CH_3)_2$, $CH_2C(=O)N(H)CH_3$, $CH_2C(=O)$—$N(H)$—$(CH_2)_2$—$N(CH_3)_2$ or $CH_2$—$N(H)$—$C(=NH)NH_2$ for each monomer of Formula II. In certain embodiments, G is $CH_3$, $CH_2CH_2$—O—$CH_3$, $CH_2C(=O)N(H)CH_3$ or $CH_2C(=O)$—$N(H)$—$(CH_2)_2$—$N(CH_3)_2$ for each monomer of Formula II.

In certain embodiments, oligomeric compounds are provided wherein each monomer of Formula II has the configuration:

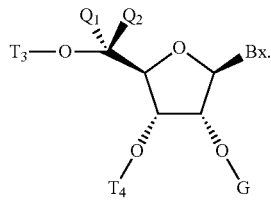

In certain embodiments, oligomeric compounds are provided comprising at least one region having at least 2 contiguous monomers of Formula II. In certain embodiments, the at least one region comprises from 2 to 5 contiguous monomers of Formula II.

In certain embodiments, oligomeric compounds are provided comprising at least two regions wherein each region independently comprises from 1 to about 5 contiguous monomers of Formula II and wherein the two regions are separated by an internal region comprising at least one monomer subunits different from monomers having Formula II and independently selected from nucleosides and modified nucleosides. In certain embodiments, oligomeric compounds are provided comprising a gapped oligomeric compound wherein one region of contiguous monomers of Formula II is located at the 5'-end and a second region of contiguous monomers of Formula II is located at the 3'-end, wherein the two regions are separated by an internal region comprising from about 6 to about 18 monomer subunits different from monomers having Formula II and independently selected from nucleosides and modified nucleosides. In certain embodiments, the internal region comprises from about 8 to about 14 contiguous β-D-2'-deoxyribofuranosyl nucleosides. In certain embodiments, the internal region comprises from about 9 to about 12 contiguous β-D-2'-deoxyribofuranosyl nucleosides.

In certain embodiments, oligomeric compounds are provided comprising one region of from 2 to three contiguous monomers of Formula II, an optional second region of 1 or 2 contiguous monomers of Formula II and a third region of from 8 to 14 β-D-2'-deoxyribofuranosyl nucleosides wherein said third region is located between said first and said second regions.

In certain embodiments, oligomeric compounds are provided wherein each internucleoside linking group is, independently, a phosphodiester internucleoside linking group or a phosphorothioate internucleoside linking group. In certain embodiments, oligomeric compounds are provided wherein essentially each internucleoside linking group is a phosphorothioate internucleoside linking group.

In certain embodiments, methods are provided comprising contacting a cell with an oligomeric compound as provided herein, wherein said oligomeric compound is complementary to a target RNA. In certain embodiments, the cell is in an animal. In certain embodiments, the cell is in a human. In certain embodiments, the target RNA is selected from mRNA, pre-mRNA and micro RNA. In certain embodiments, the target RNA is mRNA. In certain embodiments, the target RNA is human mRNA. In certain embodiments, the target RNA is cleaved thereby inhibiting its function.

In certain embodiments, the methods further comprise evaluating the antisense activity of said oligomeric compound on said cell. In certain embodiments, the evaluation includes detecting the levels of target RNA. In certain embodiments, the evaluation includes detecting the levels of a protein. In certain embodiments, the evaluation includes detection of one or more phenotypic effects.

In certain embodiments, the oligomeric compounds are provided for use in therapy. In certain embodiments, the therapy is treating a disease characterized by undesired gene expression. In certain embodiments, the therapy is treating a disease by inhibiting gene expression. In certain embodiments, the therapy involves the modulation of non-coding RNAs (reducing or increasing) which in turn affect the expression of other genes which are involved in creating a diseased state. In certain embodiments, the therapy comprises contacting a cell in an animal with an oligomeric compound or the double stranded composition as provided herein. In certain embodiments, a cell in an animal is to be contacted with the oligomeric compound.

In certain embodiments, the use of an oligomeric compound is provided for the manufacture of a medicament for the treatment of a disease characterized by undesired gene expression. In certain embodiments, the use of an oligomeric compound is provided for the manufacture of a medicament for treating a disease by inhibiting gene expression.

Also provided are pharmaceutical compositions that each comprise an oligomeric compound as provided herein and a pharmaceutically acceptable carrier.

DETAILED DESCRIPTION OF THE INVENTION

In certain embodiments, modified nucleosides are provided having at least one 5'-substitutent group and a 2'-substitutent group, oligomeric compounds that include such modified nucleosides and methods of using the oligomeric compounds. Also provided herein are intermediates and methods for preparing these modified nucleosides and oligomeric compounds. More particularly, modified nucleosides are provided that are 5'-mono (R, S or mixed) or bis substituted and 2'-substituted, that can be incorporated into oligomeric compounds. The modified nucleosides provided herein are expected to be useful for enhancing one or more properties of the oligomeric compounds they are incorporated into such as for example nuclease resistance. In certain embodiments, the oligomeric compounds and compositions provided herein are expected to hybridize to a portion of a target RNA resulting in loss of normal function of the target RNA. The oligomeric compounds are also expected to be useful as primers and probes in diagnostic applications.

In one aspect of the present invention compounds are provided having Formula I:

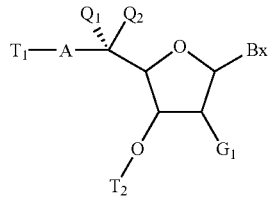

wherein:
Bx is a heterocyclic base moiety;
A is O, S or $N(R_1)$;
$R_1$ is H, $C_1$-$C_6$ alkyl or substituted $C_1$-$C_6$ alkyl;
one of $T_1$ and $T_2$ is H, a protecting group or a phosphorus moiety and the other of $T_1$ and $T_2$ is H, a protecting group or a reactive phosphorus group;
one of $Q_1$ and $Q_2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl and the other of $Q_1$ and $Q_2$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
$G_1$ is O—$[C(R_2)(R_3)]_n$—$[(C=O)_m$—$X]_j$—Z or halogen;
each $R_2$ and $R_3$ is, independently, H or halogen;
X is O, S or $N(E_1)$;
Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;
$E_1$, $E_2$ and $E_3$ are each, independently, H, $C_1$-$C_6$ alkyl or substituted $C_1$-$C_6$ alkyl;
n is from 1 to about 6;
m is 0 or 1;
j is 0 or 1;
each substituted group comprises one or more optionally protected substituent groups independently selected from halogen, $OJ_1$, $N(J_1)(J_2)$, $=NJ_1$, $SJ_1$, $N_3$, CN, $OC(=L)J_1$, $OC(=L)N(J_1)(J_2)$ and $C(=L)N(J_1)(J_2)$;
L is O, S or $NJ_3$;
each $J_1$, $J_2$ and $J_3$ is, independently, H or $C_1$-$C_6$ alkyl; and
when j is 1 then Z is other than halogen or $N(E_2)(E_3)$ and when A is O then $G_1$ is other than halogen.

In certain embodiments, the compounds of Formula I are provided having the configuration:

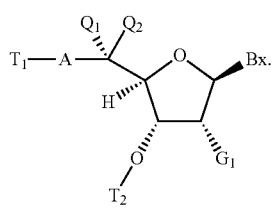

In one aspect of the present invention oligomeric compounds are provided comprising at least one monomer having Formula II:

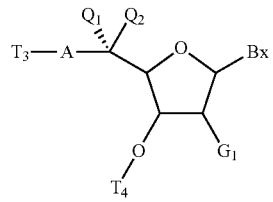

wherein independently for each monomer of Formula II:
Bx is a heterocyclic base moiety;
A is O, S or $N(R_1)$;
$R_1$ is H, $C_1$-$C_6$ alkyl or substituted $C_1$-$C_6$ alkyl;
one of $T_3$ and $T_4$ is an internucleoside linking group linking the monomer to the oligomeric compound and the other of $T_3$ and $T_4$ is H, a protecting group, a phosphorus moiety, a 5' or 3'-terminal group or an internucleoside linking group linking the monomer to the oligomeric compound;
one of $Q_1$ and $Q_2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl and the other of $Q_1$ and $Q_2$ is $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
$G_1$ is O—$[C(R_2)(R_3)]_n$—$[(C=O)_m$—$X]_j$—Z or halogen;
each $R_2$ and $R_3$ is, independently, H or halogen;
X is O, S or $N(E_1)$;
Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;
$E_1$, $E_2$ and $E_3$ are each, independently, H, $C_1$-$C_6$ alkyl or substituted $C_1$-$C_6$ alkyl;
n is from 1 to about 6;
m is 0 or 1;
j is 0 or 1;
each substituted group comprises one or more optionally protected substituent groups independently selected from halogen, $OJ_1$, $N(J_1)(J_2)$, $=NJ_1$, $SJ_1$, $N_3$, CN, $OC(=L)J_1$, $OC(=L)N(J_1)(J_2)$ and $C(=L)N(J_1)(J_2)$;
L is O, S or $NJ_3$;
each $J_1$, $J_2$ and $J_3$ is, independently, H or $C_1$-$C_6$ alkyl; and
when j is 1 then Z is other than halogen or $N(E_2)(E_3)$ and when A is O then $G_1$ is other than halogen.

In certain embodiments, oligomeric compounds are provided comprising at least one monomer having Formula II, wherein each monomer of Formula II has the configuration:

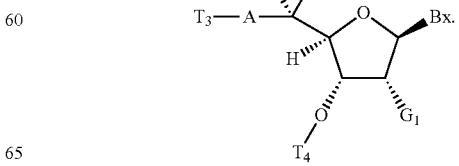

In one aspect of the present invention compounds are provided having Formula III:

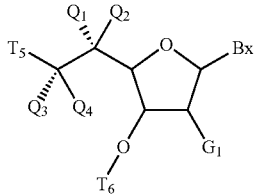

III wherein:
Bx is a heterocyclic base moiety;
$T_5$ is a phosphorus moiety or a reactive phosphorus group;
$T_6$ is H, a protecting group or a reactive phosphorus group;
$Q_1$, $Q_2$, $Q_3$ and $Q_4$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
$G_1$ is O—$[C(R_2)(R_3)]_n$—$[(C=O)_m$—$X]_j$—Z or halogen;
each $R_2$ and $R_3$ is, independently, H or halogen;
X is O, S or $N(E_1)$;
Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;
$E_1$, $E_2$ and $E_3$ are each, independently, H, $C_1$-$C_6$ alkyl or substituted $C_1$-$C_6$ alkyl;
n is from 1 to about 6;
m is 0 or 1;
j is 0 or 1;
each substituted group comprises one or more optionally protected substituent groups independently selected from halogen, $OJ_1$, $N(J_1)(J_2)$, $=NJ_1$, $SJ_1$, $N_3$, CN, $OC(=L)J_1$, $OC(=L)N(J_1)(J_2)$ and $C(=L)N(J_1)(J_2)$;
L is O, S or $NJ_3$;
each $J_1$, $J_2$ and $J_3$ is, independently, H or $C_1$-$C_6$ alkyl;
when j is 1 then Z is other than halogen or $N(E_2)(E_3)$; and
when $Q_1$, $Q_2$, $Q_3$ and $Q_4$ are each H or when $Q_1$ and $Q_2$ are H and $Q_3$ and $Q_4$ are each F or when $Q_1$ and $Q_2$ are each H and one of $Q_3$ and $Q_4$ is H and the other of $Q_3$ and $Q_4$ is $R_9$ then $G_1$ is other than H, hydroxyl, $OR_9$, halogen, $CF_3$, $CCl_3$, $CHCl_2$ and $CH_2OH$ wherein $R_9$ is alkyl, alkenyl, alkynyl, aryl or alkaryl.

In certain embodiments, the compounds of Formula III are provided having the configuration:

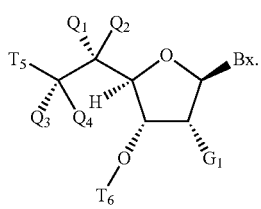

In one aspect of the present invention oligomeric compounds are provided comprising at least one monomer having Formula IV:

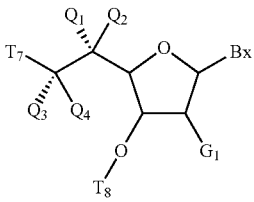

IV wherein independently for each monomer of Formula IV:
Bx is a heterocyclic base moiety;
one of $T_7$ and $T_8$ is an internucleoside linking group linking the monomer to the oligomeric compound and the other of $T_7$ and $T_8$ is H, a hydroxyl protecting group, a phosphorus moiety, a 5' or 3'-terminal group or an internucleoside linking group linking the monomer to the oligomeric compound;
$Q_1$, $Q_2$, $Q_3$ and $Q_4$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
$G_1$ is O—$[C(R_2)(R_3)]_n$—$[(C=O)_m$—$X]_j$—Z or halogen;
each $R_2$ and $R_3$ is, independently, H or halogen;
X is O, S or $N(E_1)$;
Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;
$E_1$, $E_2$ and $E_3$ are each, independently, H, $C_1$-$C_6$ alkyl or substituted $C_1$-$C_6$ alkyl;
n is from 1 to about 6;
m is 0 or 1;
j is 0 or 1;
each substituted group comprises one or more optionally protected substituent groups independently selected from halogen, $OJ_1$, $N(J_1)(J_2)$, $=NJ_1$, $SJ_1$, $N_3$, CN, $OC(=L)J_1$, $OC(=L)N(J_1)(J_2)$ and $C(=L)N(J_1)(J_2)$;
L is O, S or $NJ_3$;
each $J_1$, $J_2$ and $J_3$ is, independently, H or $C_1$-$C_6$ alkyl;
when j is 1 then Z is other than halogen or $N(E_2)(E_3)$; and
when $Q_1$, $Q_2$, $Q_3$ and $Q_4$ are each H or when $Q_1$ and $Q_2$ are H and $Q_3$ and $Q_4$ are each F or when $Q_1$ and $Q_2$ are each H and one of $Q_3$ and $Q_4$ is H and the other of $Q_3$ and $Q_4$ is $R_9$ then $G_1$ is other than H, hydroxyl, $OR_9$, halogen, $CF_3$, $CCl_3$, $CHCl_2$ and $CH_2OH$ wherein $R_9$ is alkyl, alkenyl, alkynyl, aryl or alkaryl.

In certain embodiments, oligomeric compounds are provided comprising at least one monomer having Formula IV, wherein each monomer of Formula IV has the configuration:

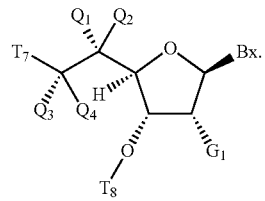

In certain embodiments, double stranded compositions are provided comprising at least one of the oligomeric compounds as provided herein. In certain embodiments, each of such oligomeric compounds can include one or more monomers selected from monomers of formula II and or monomers of formula IV. In certain embodiments, only one strand of the double stranded composition comprises one or more of the monomers as provided herein. In certain embodiments, only one strand of the double stranded composition comprises a single monomers as provided herein wherein a preferred position for such monomer is as the 5'-terminal monomer.as In certain embodiments, the 5' and 2'-modified nucleosides provided herein are useful for modifying oligomeric compounds at one or more positions. Such modified oligomeric compounds can be described as having a particular motif. Motifs include without limitation, gapped motifs, hemimer motifs, blockmer motifs, uniformly fully modified motifs, positionally modified motifs and alternating motifs. In conjunction with these motifs a wide variety of internucleoside linkages can also be used including but not limited to phosphodiester and phosphorothioate internucleoside linkages which can be incorporated uniformly or in various combinations. The oligomeric compounds can further include at least one 5' or 3' terminal group such as for example a conjugate or reporter group. The positioning of the 5' and 2'-modified nucleosides provided herein, the use of linkage strategies and 5' or 3' terminal groups can be easily optimized to enhance a desired activity for a selected target.

As used herein the term "motif" refers to the pattern created by the relative positioning of monomer subunits within an oligomeric compound wherein the pattern is determined by comparing the sugar groups. The only determinant for the motif of an oligomeric compound is the differences or lack of differences between the sugar groups. As used herein the term "sugar group" as it applies to motifs includes naturally occurring sugars having a furanose ring, sugars having a modified furanose ring and sugar surrogates wherein the furanose ring has been replaced with another ring system such as for example a morpholino or hexitol ring system. When each sugar group is the same (DNA, RNA, modified or surrogate) the motif is termed uniformly fully modified. When two or more types of sugar groups are present the motif is defined by the pattern created from the positioning of monomer subunits having one type of sugar group relative to the positioning of monomer subunits having different types of sugar groups within an oligomeric compound.

Illustrative examples of some different types of sugar groups useful in the preparation of oligomeric compounds having motifs include without limitation, β-D-ribose, β-D-2'-deoxyribose, substituted sugars (such as 2', 5' and bis substituted sugars), 4'-S-sugars (such as 4'-S-ribose, 4'-S-2'-deoxyribose and 4'-S-2'-substituted ribose), bicyclic modified sugars (such as the 2'—O—CH$_2$-4' or 2'-O—(CH$_2$)$_2$-4' bridged ribose derived bicyclic sugars) and sugar surrogates (such as when the ribose ring has been replaced with a morpholino or a hexitol ring system). The type of heterocyclic base and internucleoside linkage used at each position is variable and is not a factor in determining the motif. The presence of one or more other groups including but not limited to capping groups, conjugate groups and other 5' or 3'-terminal groups is also not a factor in determining the motif.

Representative U.S. patents that teach the preparation of motifs include without limitation, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety. Motifs are also disclosed in International Applications PCT/US2005/019219, filed Jun. 2, 2005 and published as WO 2005/121371 on Dec. 22, 2005 and PCT/US2005/019220, filed Jun. 2, 2005 and published as WO 2005/121372 on Dec. 22, 2005; each of which is incorporated by reference herein in its entirety.

As used herein the term "alternating motif" refers to a an oligomeric compound comprising a contiguous sequence of linked monomer subunits wherein the monomer subunits have two different types of sugar groups that alternate for essentially the entire sequence of the oligomeric compound. Oligomeric compounds having an alternating motif can be described by the formula: 5'-A(-L-B-L-A)$_n$(-L-B)$_{nn}$-3' where A and B are monomer subunits that have different sugar groups, each L is, independently, an internucleoside linking group, n is from about 4 to about 12 and nn is 0 or 1. The heterocyclic base and internucleoside linkage is independently variable at each position. The motif further optionally includes the use of one or more other groups including but not limited to capping groups, conjugate groups and other 5' or 3'-terminal groups. This permits alternating oligomeric compounds from about 9 to about 26 monomer subunits in length. This length range is not meant to be limiting as longer and shorter oligomeric compounds are also amenable to oligomeric compounds provided herein. In certain embodiments, one of A and B is a 5' and 2'-modified nucleoside as provided herein.

As used herein the term "uniformly fully modified motif" refers to an oligomeric compound comprising a contiguous sequence of linked monomer subunits that each have the same type of sugar group. The heterocyclic base and internucleoside linkage is independently variable at each position. The motif further optionally includes the use of one or more other groups including but not limited to capping groups, conjugate groups and other 5' or 3'-terminal groups. In certain embodiments, the uniformly fully modified motif includes a contiguous sequence of 5' and 2'-modified nucleosides. In certain embodiments, one or both of the 5' and 3'-ends of the contiguous sequence of 5' and 2'-modified nucleosides, comprise 5' or 3'-terminal groups such as one or more unmodified nucleosides.

As used herein the term "hemimer motif" refers to an oligomeric compound comprising a contiguous sequence of monomer subunits that each have the same type of sugar group with a further short contiguous sequence of monomer subunits located at the 5' or the 3' end that have a different type of sugar group. The heterocyclic base and internucleoside linkage is independently variable at each position. The motif further optionally includes the use of one or more other groups including but not limited to capping groups, conjugate groups and other 5' or 3'-terminal groups. In general, a hemimer is an oligomeric compound of uniform sugar groups further comprising a short region (1, 2, 3, 4 or about 5 monomer subunits) having uniform but different sugar groups located on either the 3' or the 5' end of the oligomeric compound.

In certain embodiments, the hemimer motif comprises a contiguous sequence of from about 10 to about 28 monomer subunits having one type of sugar group with from 1 to 5 or from 2 to about 5 monomer subunits having a second type of sugar group located at one of the termini. In certain embodiments, the hemimer is a contiguous sequence of from about 8 to about 20β-D-2'-deoxyribonucleosides having from 1-12 contiguous 5' and 2'-modified nucleosides located at one of the termini. In certain embodiments, the hemimer is a contiguous sequence of from about 8 to about 20β-D-2'-deoxyribonucleosides having from 1-5 contiguous 5' and 2'-modified nucleosides located at one of the termini. In certain embodiments, the hemimer is a contiguous sequence of from about 12 to about 18β-D-2'-deoxyribonucleosides having from 1-3 contiguous 5' and 2'-modified nucleosides located at one of the termini. In certain embodiments, the hemimer is a contiguous sequence of from about 10 to about 14β-D-2'-deoxyribonucleosides having from 1-3 contiguous 5' and 2'-modified nucleosides located at one of the termini.

As used herein the term "blockmer motif" refers to an oligomeric compound comprising an otherwise contiguous sequence of monomer subunits wherein the sugar groups of each monomer subunit is the same except for an interrupting internal block of contiguous monomer subunits having a different type of sugar group. The heterocyclic base and internucleoside linkage is independently variable at each position of a blocker oligomeric compound. The motif further optionally includes the use of one or more other groups including but not limited to capping groups, conjugate groups and other 5' or 3'-terminal groups. A blockmer overlaps somewhat with a gapmer in the definition but typically only the monomer subunits in the block have non-naturally occurring sugar groups in a blockmer and only the monomer subunits in the external regions have non-naturally occurring sugar groups in a gapmer with the remainder of monomer subunits in the blockmer or gapmer being β-D-2'-deoxyribonucleosides or β-D-ribonucleosides. In certain embodiments, blockmer oligomeric compounds are provided herein wherein all of the monomer subunits comprise non-naturally occurring sugar groups.

As used herein the term "positionally modified motif" is meant to include an otherwise contiguous sequence of monomer subunits having one type of sugar group that is interrupted with two or more regions of from 1 to about 5 contiguous monomer subunits having another type of sugar group. Each of the two or more regions of from 1 to about 5 contiguous monomer subunits are independently uniformly modified with respect to the type of sugar group. In certain embodiments, each of the two or more regions have the same type of sugar group. In certain embodiments, each of the two or more regions have a different type of sugar group. In certain embodiments, each of the two or more regions, independently, have the same or a different type of sugar group. The heterocyclic base and internucleoside linkage is independently variable at each position of a positionally modified oligomeric compound. The motif further optionally includes the use of one or more other groups including but not limited to capping groups, conjugate groups and other 5' or 3'-terminal groups. In certain embodiments, positionally modified oligomeric compounds are provided comprising a sequence of from 8 to 20β-D-2'-deoxyribonucleosides that further includes two or three regions of from 2 to about 5 contiguous 5' and 2'-modified nucleosides each. Positionally modified oligomeric compounds are distinguished from gapped motifs, hemimer motifs, blockmer motifs and alternating motifs because the pattern of regional substitution defined by any positional motif does not fit into the definition provided herein for one of these other motifs. The term positionally modified oligomeric compound includes many different specific substitution patterns.

As used herein the term "gapmer" or "gapped oligomeric compound" refers to an oligomeric compound having two external regions or wings and an internal region or gap. The three regions form a contiguous sequence of monomer subunits with the sugar groups of the external regions being different than the sugar groups of the internal region and wherein the sugar group of each monomer subunit within a particular region is essentially the same. In certain embodiments, each monomer subunit within a particular region has the same sugar group. When the sugar groups of the external regions are the same the gapmer is a symmetric gapmer and when the sugar group used in the 5'-external region is different from the sugar group used in the 3'-external region, the gapmer is an asymmetric gapmer. In certain embodiments, the external regions are small (each independently 1, 2, 3, 4 or about 5 monomer subunits) and the monomer subunits comprise non-naturally occurring sugar groups with the internal region comprising β-D-2'-deoxyribo-nucleosides. In certain embodiments, the external regions each, independently, comprise from 1 to about 5 monomer subunits having non-naturally occurring sugar groups and the internal region comprises from 6 to 18 unmodified nucleosides. The internal region or the gap generally comprises β-D-2'-deoxyribonucleosides but can comprise non-naturally occurring sugar groups. The heterocyclic base and internucleoside linkage is independently variable at each position of a gapped oligomeric compound. The motif further optionally includes the use of one or more other groups including but not limited to capping groups, conjugate groups and other 5' or 3'-terminal groups.

In certain embodiments, the gapped oligomeric compounds comprise an internal region of β-D-2'-deoxyribonucleosides with one of the external regions comprising 5' and 2'-modified nucleosides as disclosed herein. In certain embodiments, the gapped oligomeric compounds comprise an internal region of deoxyribonucleosides with both of the external regions comprising 5' and 2'-modified nucleosides as provided herein. In certain embodiments, gapped oligomeric compounds are provided herein wherein all of the monomer subunits comprise non-naturally occurring sugar groups.

In certain embodiments, gapped oligomeric compounds are provided comprising one or two 5' and 2'-modified nucleosides at the 5'-end, two or three 5' and 2'-modified nucleosides at the 3'-end and an internal region of from 10 to 16β-D-2'-deoxyribonucleosides. In certain embodiments, gapped oligomeric compounds are provided comprising one 5' and 2'-modified nucleosides at the 5'-end, two 5' and 2'-modified nucleosides at the 3'-end and an internal region of from 10 to 16β-D-2'-deoxyribonucleosides. In certain embodiments, gapped oligomeric compounds are provided comprising one 5' and 2'-modified nucleosides at the 5'-end, two 5' and 2'-modified nucleosides at the 3'-end and an internal region of from 10 to 14β-D-2'-deoxyribonucleosides.

In certain embodiments, gapped oligomeric compounds are provided that are from about 10 to about 21 monomer subunits in length. In certain embodiments, gapped oligomeric compounds are provided that are from about 12 to about 16 monomer subunits in length. In certain embodiments, gapped oligomeric compounds are provided that are from about 12 to about 14 monomer subunits in length.

The terms "substituent" and "substituent group," as used herein, are meant to include groups that are typically added to other groups or parent compounds to enhance desired properties or provide other desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to a parent compound.

Substituent groups amenable herein include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino(=N$R_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)N($R_{bb}$)($R_{cc}$)), thiouredio (—N($R_{bb}$)C(S)N($R_{bb}$)—($R_{cc}$)), guanidinyl (—N($R_{bb}$)C(=N$R_{bb}$)N($R_{bb}$)($R_{cc}$)), amidinyl (—C(=N$R_{bb}$)

N($R_{bb}$)($R_{cc}$) or —N($R_{bb}$)C(=N$R_{bb}$)($R_{aa}$)), thiol (—S$R_{bb}$), sulfinyl (—S(O)$R_{bb}$), sulfonyl (—S(O)$_2$$R_{bb}$) and sulfonamidyl (—S(O)$_2$N($R_{bb}$)($R_{cc}$) or —N($R_{bb}$) or —N($R_{bb}$)S—(O)$_2$$R_{bb}$). Wherein each $R_{aa}$, $R_{bb}$ and $R_{cc}$ is, independently, H, an optionally linked chemical functional group or a further substituent group with a preferred list including without limitation, H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

The terms "stable compound" and "stable structure" as used herein are meant to indicate a compound that is sufficiently robust to survive isolation to a useful degree of purity from a reaction mixture, and formulation into an efficacious therapeutic agent. Only stable compounds are contemplated herein.

The term "alkyl," as used herein, refers to a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substituent groups.

The term "alkenyl," as used herein, refers to a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

The term "alkynyl," as used herein, refers to a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

The term "acyl," as used herein, refers to a radical formed by removal of a hydroxyl group from an organic acid and has the general formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

The term "alicyclic" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

The term "alkoxy," as used herein, refers to a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

The term "aminoalkyl" as used herein, refers to an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

The terms "aralkyl" and "arylalkyl," as used herein, refer to an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

The terms "aryl" and "aromatic," as used herein, refer to a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

The terms "halo" and "halogen," as used herein, refer to an atom selected from fluorine, chlorine, bromine and iodine.

The terms "heteroaryl," and "heteroaromatic," as used herein, refer to a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

The term "heteroarylalkyl," as used herein, refers to a heteroaryl group as previously defined that further includes a covalently attached $C_1$-$C_{12}$ alkyl radical. The alkyl radical portion of the resulting heteroarylalkyl group is capable of forming a covalent bond with a parent molecule. Examples include without limitation, pyridinylmethyl, pyrimidinylethyl, napthyridinylpropyl and the like. Heteroarylalkyl groups as used herein may optionally include further substituent groups on one or both of the heteroaryl or alkyl portions.

The term "heterocyclic radical" as used herein, refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic radical typically includes at least one atom selected from sulfur, nitrogen or oxygen. Examples of heterocyclic radicals include, [1,3]dioxolanyl, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substituent groups.

The term "hydrocarbyl" includes radical groups that comprise C, O and H. Included are straight, branched and cyclic groups having any degree of saturation. Such hydrocarbyl groups can include one or more heteroatoms selected from N, O and S and can be further mono or poly substituted with one or more substituent groups.

The term "mono or poly cyclic structure" as used herein includes all ring systems selected from single or polycyclic radical ring systems wherein the rings are fused or linked and is meant to be inclusive of single and mixed ring systems individually selected from aliphatic, alicyclic, aryl, heteroaryl, aralkyl, arylalkyl, heterocyclic, heteroaryl, heteroaromatic and heteroarylalkyl. Such mono and poly cyclic structures can contain rings that each have the same level of saturation or each, independently, have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or poly cyclic structures can be further substituted with substituent groups such as for example phthalimide which has two =O groups attached to one of the rings. Mono or poly cyclic structures can be attached to parent molecules using various strategies such as directly through a ring atom, through a substituent group or through a bifunctional linking moiety.

The term "oxo" refers to the group (=O).

Linking groups or bifunctional linking moieties such as those known in the art are useful for attachment of chemical functional groups, conjugate groups, reporter groups and other groups to selective sites in a parent compound such as for example an oligomeric compound. In general, a bifunctional linking moiety comprises a hydrocarbyl moiety having two functional groups. One of the functional groups is selected to bind to a parent molecule or compound of interest and the other is selected to bind to essentially any selected group such as a chemical functional group or a conjugate group. In some embodiments, the linker comprises a chain structure or a polymer of repeating units such as ethylene glycols or amino acid units. Examples of functional groups that are routinely used in bifunctional linking moieties include without limitation, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include without limitation, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, the oligomeric compounds as provided herein can be modified by covalent attachment of one or more conjugate groups. In general, conjugate groups modify one or more properties of the oligomeric compounds they are attached to. Such oligonucleotide properties include without limitation, pharmacodynamics, pharmacokinetics, binding, absorption, cellular distribution, cellular uptake, charge and clearance. Conjugate groups are routinely used in the chemical arts and are linked directly or via an optional linking moiety or linking group to a parent compound such as an oligomeric compound. A preferred list of conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes.

In certain embodiments, the oligomeric compounds as provided herein can be modified by covalent attachment of one or more 5' or 3'-terminal groups. The terms "5' or 3'-terminal groups", "5-terminal groups" and "3'-terminal group" as used herein are meant to include useful groups known to the art skilled that can be placed on one or both of the 5' and 3'-ends of an oligomeric compound respectively, for various purposes such as enabling the tracking of the oligomeric compound (a fluorescent label or other reporter group), improving the pharmacokinetics or pharmacodynamics of the oligomeric compound (such as for example: enhancing uptake and/or delivery) or enhancing one or more other desirable properties of the oligomeric compound (a group for improving nuclease stability or binding affinity). In certain embodiments, 5' and 3'-terminal groups include without limitation, modified or unmodified nucleosides; two or more linked nucleosides that are independently, modified or unmodified; conjugate groups; capping groups; phosphate moieties; and protecting groups. In certain embodiments, 5' and 3'-terminal groups include without limitation, modified or unmodified nucleosides; one or more linked nucleosides that are independently, modified or unmodified and can be hybridizing or non-hybridizing to either a nucleic acid target and or a second strand as for example in a double stranded composition; conjugate groups; capping groups; phosphate moieties; and protecting groups.

The term "phosphate moiety" as used herein, refers to a terminal phosphate group that includes phosphates as well as modified phosphates. The phosphate moiety can be located at either terminus but is preferred at the 5'-terminal nucleoside. In one aspect, the terminal phosphate is unmodified having the formula —O—P(=O)(OH)OH. In another aspect, the terminal phosphate is modified such that one or more of the O and OH groups are replaced with H, O, S, N(R) or alkyl where R is H, an amino protecting group or unsubstituted or substituted alkyl. In certain embodiments, the 5' and or 3' terminal group can comprise from 1 to 3 phosphate moieties that are each, independently, unmodified or modified.

As used herein, the term "phosphorus moiety" refers to monovalent $P^V$ phosphorus radical group. In certain embodiments, the phosphorus moiety has the formula:

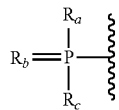

wherein:

$R_a$ and $R_c$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino; and $R_b$ is O or S.

The term "protecting group," as used herein, refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene's Protective Groups in Organic Synthesis, 4th edition, John Wiley & Sons, New York, 2007.

Groups can be selectively incorporated into oligomeric compounds as provided herein as precursors. For example an amino group can be placed into a compound as provided herein as an azido group that can be chemically converted to the amino group at a desired point in the synthesis. Generally, groups are protected or present as precursors that will be inert to reactions that modify other areas of the parent molecule for conversion into their final groups at an appropriate time. Further representative protecting or precursor groups are discussed in Agrawal et al., *Protocols for Oligonucleotide Conjugates*, Humana Press; New Jersey, 1994, 26, 1-72.

The term "orthogonally protected" refers to functional groups which are protected with different classes of protecting groups, wherein each class of protecting group can be removed in any order and in the presence of all other classes (see, Barany et al., *J. Am. Chem. Soc.,* 1977, 99, 7363-7365; Barany et al., *J. Am. Chem. Soc.,* 1980, 102, 3084-3095). Orthogonal protection is widely used in for example automated oligonucleotide synthesis. A functional group is deblocked in the presence of one or more other protected functional groups which is not affected by the deblocking procedure. This deblocked functional group is reacted in some manner and at some point a further orthogonal protecting group is removed under a different set of reaction conditions. This allows for selective chemistry to arrive at a desired compound or oligomeric compound.

Examples of hydroxyl protecting groups include without limitation, acetyl, t-butyl, t-butoxymethyl, methoxymethyl, tetrahydropyranyl, 1-ethoxyethyl, 1-(2-chloroethoxy)ethyl, p-chlorophenyl, 2,4-dinitrophenyl, benzyl, 2,6-dichlorobenzyl, diphenylmethyl, p-nitrobenzyl, bis(2-acetoxyethoxy) methyl (ACE), 2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate, chloroacetyl, trichloroacetyl, trifluoro-acetyl, pivaloyl, benzoyl, p-phenylbenzoyl, 9-fluorenylmethyl carbonate, mesylate, tosylate, triphenylmethyl (trityl), monomethoxytrityl, dimethoxytrityl (DMT), trimethoxytrityl, 1(2-fluorophenyl)-4-methoxypiperidin-4-yl (FPMP), 9-phenylxanthine-9-yl (Pixyl) and 9-(p-methoxyphenyl)xanthine-9-yl (MOX). Wherein more commonly used hydroxyl protecting groups include without limitation, benzyl, 2,6-dichlorobenzyl, t-butyldimethylsilyl, t-butyldiphenylsilyl, benzoyl, mesylate, tosylate, dimethoxytrityl (DMT), 9-phenylxanthine-9-yl (Pixyl) and 9-(p-methoxyphenyl)xanthine-9-yl (MOX).

Examples of amino protecting groups include without limitation, carbamate-protecting groups, such as 2-trimethylsilylethoxycarbonyl (Teoc), 1-methyl-1-(4-biphenyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

Examples of thiol protecting groups include without limitation, triphenylmethyl (trityl), benzyl (Bn), and the like.

In certain embodiments, oligomeric compounds as provided herein can be prepared having one or more optionally protected phosphorus containing internucleoside linkages. Representative protecting groups for phosphorus containing internucleoside linkages such as phosphodiester and phosphorothioate linkages include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. Nos. 4,725, 677 and Re. 34,069 (β-cyanoethyl); Beaucage et al., *Tetrahedron,* 1993, 49(10), 1925-1963; Beaucage et al., *Tetrahedron,* 1993, 49(46), 10441-10488; Beaucage et al., *Tetrahedron,* 1992, 48(12), 2223-2311.

In certain embodiments, compounds having reactive phosphorus groups are provided that are useful for forming internucleoside linkages including for example phosphodiester and phosphorothioate internucleoside linkages. Such reactive phosphorus groups are known in the art and contain phosphorus atoms in $P^{III}$ or $P^V$ valence state including, but not limited to, phosphoramidite, H-phosphonate, phosphate triesters and phosphorus containing chiral auxiliaries. In certain embodiments, reactive phosphorus groups are included that provide a 5'-methylene phosphonate internucleoside linkage upon reaction with a free 3'-hydroxyl group. Such reactive phosphorus groups include without limitation 6'-(P=$R_c$)(O$R_d$)$_2$ wherein each $R_d$ is, independently, a protecting group, $C_1$-$C_6$ alkyl, substituted $C_1$-$C_6$ alkyl, aryl or substituted aryl and $R_e$ is O or S. In certain embodiments, reactive phosphorus groups are selected from diisopropylcyanoethoxy phosphoramidite (—O*—P[N[(CH(CH$_3$)$_2$]$_2$]O(CH$_2$)$_2$CN), H-phosphonate (—O*—P(=O)(H)OH), wherein the O* is provided from the Markush group for the monomer. A preferred synthetic solid phase synthesis utilizes phosphoramidites ($P^{III}$ chemistry) as reactive phosphites. The intermediate phosphite compounds are subsequently oxidized to the phosphate or thiophosphate ($P^V$ chemistry) using known methods to yield, phosphodiester or phosphorothioate internucleoside linkages. Additional reactive phosphates and phosphites are disclosed in Tetrahedron Report Number 309 (Beaucage and Iyer, *Tetrahedron*, 1992, 48, 2223-2311).

As used herein the term "internucleoside linkage" or "internucleoside linking group" is meant to include all manner of internucleoside linking groups known in the art including but not limited to, phosphorus containing internucleoside linking groups such as phosphodiester and phosphorothioate, and non-phosphorus containing internucleoside linking groups such as formacetyl and methyleneimino. Internucleoside linkages also includes neutral non-ionic internucleoside linkages such as amide-3 (3'-$CH_2$—C(=O)—N(H)-5'), amide-4(3'-$CH_2$—N(H)—C(=O)-5') and methylphosphonate wherein a phosphorus atom is not always present.

In certain embodiments, oligomeric compounds as provided herein can be prepared having one or more internucleoside linkages containing modified e.g. non-naturally occurring internucleoside linkages. The two main classes of internucleoside linkages are defined by the presence or absence of a phosphorus atom. Modified internucleoside linkages having a phosphorus atom include without limitation, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus containing linkages include without limitation, U.S. Pat. Nos. 3,687,808; 4,469,863; 4,476,301; 5,023,243; 5,177,196; 5,188,897; 5,194,599; 5,264,423; 5,276,019; 5,278,302; 5,286,717; 5,321,131; 5,399,676; 5,405,939; 5,453,496; 5,455,233; 5,466,677; 5,476,925; 5,519,126; 5,527,899; 5,536,821; 5,541,306; 5,550,111; 5,563,253; 5,565,555; 5,571,799; 5,587,361; 5,625,050; 5,672,697 and 5,721,218, certain of which are commonly owned with this application, and each of which is herein incorporated by reference.

In certain embodiments, oligomeric compounds as provided herein can be prepared having one or more non-phosphorus containing internucleoside linkages. Such oligomeric compounds include without limitation, those that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include without limitation, U.S. Pat. Nos. 5,034,506; 5,166,315; 5,185,444; 5,214,134; 5,216, 141; 5,235,033; 5,264,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; 5,677,439; 5,646,269 and 5,792,608, certain of which are commonly owned with this application, and each of which is herein incorporated by reference.

As used herein the phrase "neutral internucleoside linkage" is intended to include internucleoside linkages that are non-ionic. Neutral internucleoside linkages include without limitation, phosphotriesters, methylphosphonates, MMI (3'-$CH_2$—N($CH_3$)—O-5'), amide-3 (3'-$CH_2$—C(=O)—N(H)-5'), amide-4 (3'-$CH_2$—N(H)—C(=O)-5'), formacetal (3'-O—$CH_2$—O-5'), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

The 5' and 2'-modified nucleosides provided herein can be prepared by any of the applicable techniques of organic synthesis, as, for example, illustrated in the examples below. Many such techniques are well known in the art. However, many of the known techniques are elaborated in *Compendium of Organic Synthetic Methods*, John Wiley & Sons, New York: Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade Jr., 1980; Vol. 5, Leroy G. Wade Jr., 1984; and Vol. 6, Michael B. Smith; as well as March, J., *Advanced Organic Chemistry*, 3rd Edition, John Wiley & Sons, New York, 1985; *Comprehensive Organic Synthesis. Selectivity, Strategy & Efficiency in Modern Organic Chemistry*, in 9 Volumes, Barry M. Trost, Editor-in-Chief, Pergamon Press, New York, 1993; *Advanced Organic Chemistry, Part B: Reactions and Synthesis,* 4th Edition; Carey and Sundberg, Kluwer Academic/Plenum Publishers, New York, 2001; *Advanced Organic Chemistry, Reactions, Mechanisms, and Structure*, 2nd Edition, March, McGraw Hill, 1977; Greene, T. W., and Wutz, P. G. M., *Protecting Groups in Organic Synthesis*, 4th Edition, John Wiley & Sons, New York, 1991; and Larock, R. C., *Comprehensive Organic Transformations*, 2nd Edition, John Wiley & Sons, New York, 1999.

The compounds described herein contain one or more asymmetric centers and thus give rise to enantiomers, diastereomers, and other stereoisomeric forms that may be defined, in terms of absolute stereochemistry, as (R)- or (S)-, α or β, or as (D)- or (L)-such as for amino acids. Included herein are all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions*, John Wiley & Sons, 1981. When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to limit a particular configuration unless the text so states.

As is known in the art, a nucleoside is a base-sugar combination. The base portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond. However, open linear structures are generally desired. Within the oligonucleotide structure, the phosphate groups are commonly referred to as forming the internucleoside linkages of the oligonucleotide. The normal internucleoside linkage of RNA and DNA is a 3' to 5' phosphodiester linkage.

The term "nucleotide mimetic" as used herein is meant to include monomers that incorporate into oligomeric compounds with sugar and linkage surrogate groups, such as for example peptide nucleic acids (PNA) or morpholinos (linked by —N(H)—C(=O)—O—). In general, the heterocyclic base at each position is maintained for hybridization to a nucleic acid target but the sugar and linkage is replaced with surrogate groups that are expected to function similar to native groups but have one or more enhanced properties.

As used herein the term "nucleoside mimetic" is intended to include those structures used to replace the sugar and the base at one or more positions of an oligomeric compound. Examples of nucleoside mimetics include without limitation replacement of the heterocyclic base moiety with a mimetic thereof such as a phenoxazine moiety (for example the 9-(2-aminoethoxy)-1,3-diazaphenoxazine-2-one group, also referred to as a G-clamp which forms four hydrogen bonds when hybridized with a guanosine base) and further replacement of the sugar group with a group such as for example a morpholino, a cyclohexenyl or a bicyclo[3.1.0]hexyl.

As used herein the term "modified nucleoside" is meant to include all manner of modified nucleosides that can be incorporated into an oligomeric compound using oligomer synthesis. The term is intended to include modifications made to a nucleoside such as modified stereochemical configurations, one or more substitutions, and deletion of groups as opposed to the use of surrogate groups which are described elsewhere herein. The term includes nucleosides having a furanose sugar (or 4'-S analog) portion and can include a heterocyclic base but abasic modified nucleosides are also envisioned. One group of representative modified nucleosides includes without limitation, substituted nucleosides (such as 2', 5', and/or 4' substituted nucleosides) 4'-S-modified nucleosides, (such as 4'-S-ribonucleosides, 4'-S-2'-deoxyribonucleosides and 4'-S-2'-substituted ribonucleosides), bicyclic modified nucleosides (such as for example, bicyclic nucleosides wherein the sugar group has a 2'-O—CHR$_a$-4' bridging group, wherein R$_a$ is H, alkyl or substituted alkyl) and base modified nucleosides. The sugar can be modified with more than one of these modifications listed such as for example a bicyclic modified nucleoside further including a 5'-substitution or a 5' or 4' substituted nucleoside further including a 2' substituent. The term modified nucleoside also includes combinations of these modifications such as a base and sugar modified nucleosides. These modifications are meant to be illustrative and not exhaustive as other modifications are known in the art and are also envisioned as possible modifications for the modified nucleosides described herein.

As used herein the term "monomer subunit" is meant to include all manner of monomer units that are amenable to oligomer synthesis with one preferred list including monomer subunits such as β-D-ribonucleosides, β-D-2'-deoxyribonucleosides, modified nucleosides, including substituted nucleosides (such as 2', 5' and bis substituted nucleosides), 4'-S-modified nucleosides, (such as 4'-S-ribonucleosides, 4'-S-2'-deoxyribonucleosides and 4'-S-2'-substituted ribonucleosides), bicyclic modified nucleosides (such as bicyclic nucleosides wherein the sugar group has a 2'-O—CHR$_a$-4' bridging group, wherein R$_a$ is H, alkyl or substituted alkyl), other modified nucleosides, nucleoside mimetics and nucleosides having sugar surrogates.

The term "oligonucleotide" refers to an oligomer or polymer of ribonucleic acid (RNA) or deoxyribonucleic acid (DNA). This term includes oligonucleotides composed of naturally-occurring nucleobases, sugars and covalent internucleoside linkages. The term "oligonucleotide analog" refers to oligonucleotides that have one or more non-naturally occurring portions. Such non-naturally occurring oligonucleotides are often desired over naturally occurring forms because of desirable properties such as, for example, enhanced cellular uptake, enhanced affinity for nucleic acid target and/or increased stability in the presence of nucleases.

The term "oligonucleoside" refers to a sequence of nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include without limitation, siloxane, sulfide, sulfoxide, sulfone, acetyl, formacetyl, thioformacetyl, methylene formacetyl, thioformacetyl, alkeneyl, sulfamate, methyleneimino, methylenehydrazino, sulfonate, sulfonamide, amide and others having mixed N, O, S and CH$_2$ component parts.

The terms "heterocyclic base moiety" and "nucleobase" as used herein, include unmodified or naturally occurring nucleobases, modified or non-naturally occurring nucleobases as well as synthetic mimetics thereof (such as for example phenoxazines). In general, a heterocyclic base moiety is heterocyclic system that contains one or more atoms or groups of atoms capable of hydrogen bonding to a base of a nucleic acid.

As used herein the terms, "unmodified nucleobase" and "naturally occurring nucleobase" include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-13][1,4]benzoxazin-2 (3H)-one), carbazole cytidine pyrimido[4,5-b]indol-2-one), pyridoindole cytidine (H-pyrido[3',2':4,5]pyrrolo[2,3-d]pyrimidine-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

The heterocyclic base moiety of each of the 5' and 2'-modified nucleosides can be modified with one or more substituent groups to enhance one or more properties such as affinity for a target strand or affect some other property in an advantageous manner. Modified nucleobases include without limitation, universal bases, hydrophobic bases, promiscuous bases, size-expanded bases, and fluorinated bases as defined herein. Certain of these nucleobases are particularly useful for increasing the binding affinity of the oligomeric compounds as provided herein. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (*Antisense Research and Applications*, Sanghvi, Y. S., Crooke, S. T. and Lebleu, B., Eds., CRC Press, Boca Raton, 1993, 276-278).

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

In general, the term "oligomeric compound" refers to a contiguous sequence of linked monomer subunits. In general, each linked monomer subunit is directly or indirectly attached to a heterocyclic base moiety but abasic sites are also possible. At least some and generally most if not essentially all of the heterocyclic bases in an oligomeric compound are capable of hybridizing to a nucleic acid molecule, normally a preselected RNA target. The term "oligomeric compound" therefore includes oligonucleotides, oligonucleotide analogs and oligonucleosides. It also includes polymers having a plurality of non-naturally occurring nucleoside mimetics and/or nucleosides having sugar surrogate groups. In certain embodiments, oligomeric compounds comprise a plurality of monomer subunits independently selected from naturally occurring nucleosides, non-naturally occurring nucleosides, modified nucleosides, nucleoside mimetics, and nucleosides having sugar surrogate groups.

When preparing oligomeric compounds having specific motifs as disclosed herein it can be advantageous to mix non-naturally occurring monomer subunits such as the 5' and 2'-modified nucleosides as provided herein with other non-naturally occurring monomer subunits, naturally occurring monomer subunits (nucleosides) or mixtures thereof. In certain embodiments, oligomeric compounds are provided herein comprising a contiguous sequence of linked monomer subunits wherein at least one monomer subunit is a 5' and 2'-modified nucleoside as provided herein. In certain embodiments, oligomeric compounds are provided comprising a plurality of 5' and 2'-modified nucleosides as provided herein.

Oligomeric compounds are routinely prepared linearly but can also be joined or otherwise prepared to be circular and/or can be prepared to include branching. Oligomeric compounds can form double stranded constructs such as for example two strands hybridized to form a double stranded composition. Double stranded compositions can be linked or separate and can include various other groups such as conjugates and/or overhangs on the ends.

Oligomeric compounds provided herein can optionally contain one or more nucleosides wherein the sugar group has been modified. Such sugar modified nucleosides may impart enhanced nuclease stability, increased binding affinity or some other beneficial biological property to the oligomeric compounds. As used herein the term "modified sugar" refers to modifications that can be made to the furanose sugar portion of otherwise unmodified or modified nucleosides useful herein. Such modified sugars include without limitation substitution with one or more substituent groups, bridging of two non-geminal ring carbon atoms to form a bicyclic nucleoside or substitution of the 4'-O atom with a disubstituted methylene group [$C(R)_2$] or a heteroatom or substituted heteroatom (NR). Modified sugar moieties can also comprise mixtures of these modifications such as for example putting a 5'-substituent group on a bicyclic nucleoside.

In certain embodiments, examples of substituent groups useful for modifying furanose sugar moieties (e.g., sugar substituent groups used for nucleosides), include without limitation 2'-F, 2'-allyl, 2'-amino, 2'-azido, 2'-thio, 2'-O-allyl, 2'-OCF$_3$, 2'-O—C$_1$-C$_{10}$ alkyl, 2'-O—CH$_3$, OCF$_3$, 2'-O—CH$_2$CH$_3$, 2'-O—(CH$_2$)$_2$—O—(CH$_2$)$_2$—O—CH$_3$, 2O(CH$_2$)$_2$SCH$_3$, 2'-O—CH$_2$—CH═CH$_2$(MOE), 2'-O—(CH$_2$)$_3$—N(R$_m$)(R$_n$), 2'-O—(CH$_2$)$_2$—O—N(R$_m$)(R$_n$), 2'-O—(CH$_2$)$_2$—O—(CH$_2$)$_2$—N(R$_m$)(R$_n$), 2'-O—CH$_2$C(═O)—N(H)—(CH$_2$)$_2$—N(R$_m$)(R$_n$) and 2'-O—CH$_2$—N(H)—C(═NR$_m$)[N(R$_m$)(R$_n$)], 5'-vinyl, 5'-methyl (R or S) and 4'-S wherein each R$_m$ and R$_n$ is, independently, H, substituted or unsubstituted C$_1$-C$_{10}$ alkyl or a protecting group. Further examples of modified sugar moieties include without limitation bicyclic sugars (e.g. bicyclic nucleic acids or bicyclic nucleosides discussed below).

Combinations of these modifications are also provided for herein without limitation, such as 2'-F-5'-methyl substituted nucleosides (see PCT International Application WO 2008/101157 Published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group).

As used herein the terms "bicyclic nucleic acid" and "bicyclic nucleoside" refer to nucleosides wherein the sugar portion of the nucleoside is bicyclic (e.g. bicyclic sugar). In certain embodiments, a bicyclic nucleic acid comprises a nucleoside wherein the furanose ring comprises a bridge between two non-geminal ring carbon atoms. Examples of bicyclic nucleosides include without limitation nucleosides comprising a bridge between the 4' and the 2' ribosyl ring atoms. In certain embodiments, oligomeric compounds provided herein include one or more bicyclic nucleosides wherein the bridge comprises one of the formulae: 4'-(CH$_2$)—O-2' (LNA); 4'-(CH$_2$)—S-2; 4'-(CH$_2$)$_2$—O-2' (ENA); 4'-CH(CH$_3$)—O-2' and 4'-C—H(CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see published International Application WO/2009/006478, published Jan. 8, 2009); 4'-CH$_2$—N(OCH$_3$)-2' (and analogs thereof see published International Application WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya, et al., *J. Org. Chem.*, 2009, 74, 118-134); and 4'-CH$_2$—C(=CH$_2$)-2' (and analogs thereof see published International Application WO 2008/154401, published on Dec. 8, 2008). Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

As used herein the term "sugar surrogate" refers to replacement of the nucleoside furanose ring with a non-furanose (or 4'-substituted furanose) group with another structure such as another ring system or open system. Such structures can be as simple as a six membered ring as opposed to the five membered furanose ring or can be more complicated as is the case with the non-ring system used in peptide nucleic acid. The term is meant to include replacement of the sugar group with all manner of sugar surrogates know in the art and includes without limitation sugar surrogate groups such as morpholinos, cyclohexenyls and cyclohexitols. In most monomer subunits having a sugar surrogate group the heterocyclic base moiety is generally maintained to permit hybridization.

In certain embodiments, nucleosides having sugar surrogate groups include without limitation, replacement of the ribosyl ring with a surrogate ring system such as a tetrahydropyranyl ring system (also referred to as hexitol) as illustrated below:

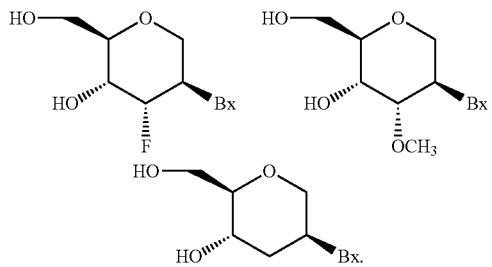

Many other monocyclic, bicyclic and tricyclic ring systems are known in the art and are suitable as sugar surrogates that can be used to modify nucleosides for incorporation into oligomeric compounds as provided herein (see for example review article: Leumann, Christian J.). Such ring systems can undergo various additional substitutions to further enhance their activity.

Some representative U.S. patents that teach the preparation of such modified sugars include without limitation, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005 certain of which are commonly owned with the instant application, and each of which is herein incorporated by reference in its entirety.

Those skilled in the art, having possession of the present disclosure will be able to prepare oligomeric compounds, comprising a contiguous sequence of linked monomer subunits, of essentially any viable length to practice the methods disclosed herein. Such oligomeric compounds will include at least one and preferably a plurality of the 5' and 2'-modified nucleosides provided herein and may also include other monomer subunits including but not limited to nucleosides, modified nucleosides, nucleosides comprising sugar surrogate groups and nucleoside mimetics.

In certain embodiments, oligomeric compounds provided herein comprise from about 8 to about 80 monomer subunits in length. One having ordinary skill in the art will appreciate that this embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 monomer subunits in length, or any range therewithin.

In certain embodiments, oligomeric compounds provided herein comprise from about 8 to 40 monomer subunits in length. One having ordinary skill in the art will appreciate that this embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 monomer subunits in length, or any range therewithin.

In certain embodiments, oligomeric compounds provided herein comprise from about 8 to 20 monomer subunits in length. One having ordinary skill in the art will appreciate that this embodies oligomeric compounds of 8, 9, 10, 11, 12, 13, 14, 15, 16, 17, 18, 19 or 20 monomer subunits in length, or any range therewithin.

In certain embodiments, oligomeric compounds provided herein comprise from about 8 to 16 monomer subunits in length. One having ordinary skill in the art will appreciate that this embodies oligomeric compounds of 8, 9, 10, 11, 12, 13, 14, 15 or 16 monomer subunits in length, or any range therewithin.

In certain embodiments, oligomeric compounds provided herein comprise from about 10 to 14 monomer subunits in length. One having ordinary skill in the art will appreciate that this embodies oligomeric compounds of 10, 11, 12, 13 or 14 monomer subunits in length, or any range therewithin.

In certain embodiments, oligomeric compounds provided herein comprise from about 10 to 18 monomer subunits in length. One having ordinary skill in the art will appreciate that this embodies oligomeric compounds of 10, 11, 12, 13, 14, 15, 16, 17 or 18 monomer subunits in length, or any range therewithin.

In certain embodiments, oligomeric compounds provided herein comprise from about 10 to 21 monomer subunits in length. One having ordinary skill in the art will appreciate that this embodies oligomeric compounds of 10, 11, 12, 13, 14, 15, 16, 17, 18, 19, 20 or 21 monomer subunits in length, or any range therewithin.

In certain embodiments, oligomeric compounds provided herein comprise from about 12 to 14 monomer subunits in length. One having ordinary skill in the art will appreciate that this embodies oligomeric compounds of 12, 13 or 14 monomer subunits in length, or any range therewithin.

In certain embodiments, oligomeric compounds provided herein comprise from about 12 to 18 monomer subunits in length. One having ordinary skill in the art will appreciate that this embodies oligomeric compounds of 12, 13, 14, 15, 16, 17 or 18 monomer subunits in length, or any range therewithin.

In certain embodiments, oligomeric compounds provided herein comprise from about 12 to 21 monomer subunits in length. One having ordinary skill in the art will appreciate that this embodies oligomeric compounds of 12, 13, 14, 15, 16, 17, 18, 19, 20 or 21 monomer subunits in length, or any range therewithin.

In certain embodiments, oligomeric compounds provided herein comprise from about 14 to 18 monomer subunits in length. One having ordinary skill in the art will appreciate that this embodies oligomeric compounds of 14, 15, 16, 17 or 18 monomer subunits in length, or any range therewithin.

In certain embodiments, oligomeric compounds of any of a variety of ranges of lengths of linked monomer subunits are provided. In certain embodiments, oligomeric compounds are provided consisting of X—Y linked monomer subunits, where X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, this provides oligomeric compounds comprising: 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 11-12, 11-13, 11-14, 11-15, 11-16, 11-17, 11-18, 11-19, 11-20, 11-21, 11-22, 11-23, 11-24, 11-25, 11-26, 11-27, 11-28, 11-29, 11-30, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 13-14, 13-15, 13-16, 13-17, 13-18, 13-19, 13-20, 13-21, 13-22, 13-23, 13-24, 13-25, 13-26, 13-27, 13-28, 13-29, 13-30, 14-15, 14-16, 14-17, 14-18, 14-19, 14-20, 14-21, 14-22, 14-23, 14-24, 14-25, 14-26, 14-27, 14-28, 14-29, 14-30, 15-16, 15-17, 15-18, 15-19, 15-20, 15-21, 15-22, 15-23, 15-24, 15-25, 15-26, 15-27, 15-28, 15-29, 15-30, 16-17, 16-18, 16-19, 16-20, 16-21, 16-22, 16-23, 16-24, 16-25, 16-26, 16-27, 16-28, 16-29, 16-30, 17-18, 17-19, 17-20, 17-21, 17-22, 17-23, 17-24, 17-25, 17-26, 17-27, 17-28, 17-29, 17-30, 18-19, 18-20, 18-21, 18-22, 18-23, 18-24, 18-25, 18-26, 18-27, 18-28, 18-29, 18-30, 19-20, 19-21, 19-22, 19-23, 19-24, 19-25, 19-26, 19-29, 19-28, 19-29, 19-30, 20-21, 20-22, 20-23, 20-24, 20-25, 20-26, 20-27, 20-28, 20-29, 20-30, 21-22, 21-23, 21-24, 21-25, 21-26, 21-27, 21-28, 21-29, 21-30, 22-23, 22-24, 22-25, 22-26, 22-27, 22-28, 22-29, 22-30, 23-24, 23-25, 23-26, 23-27, 23-28, 23-29, 23-30, 24-25, 24-26, 24-27, 24-28, 24-29, 24-30, 25-26, 25-27, 25-28, 25-29, 25-30, 26-27, 26-28, 26-29, 26-30, 27-28, 27-29, 27-30, 28-29, 28-30, or 29-30 linked monomer subunits.

In certain embodiments, the ranges for the oligomeric compounds listed herein are meant to limit the number of monomer subunits in the oligomeric compounds, however such oligomeric compounds may further include 5' and/or 3'-terminal groups including but not limited to protecting groups such as hydroxyl protecting groups, optionally linked conjugate groups and/or other substituent groups.

In certain embodiments, the preparation of oligomeric compounds as disclosed herein is performed according to literature procedures for DNA: Protocols for Oligonucleotides and Analogs, Agrawal, Ed., Humana Press, 1993, and/or RNA: Scaringe, *Methods,* 2001, 23, 206-217; Gait et al., *Applications of Chemically synthesized RNA in RNA:Protein Interactions*, Smith, Ed., 1998, 1-36; Gallo et al., *Tetrahedron,* 2001, 57, 5707-5713. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069.

Oligomeric compounds are routinely prepared using solid support methods as opposed to solution phase methods. Commercially available equipment commonly used for the preparation of oligomeric compounds that utilize the solid support method is sold by several vendors including, for example, Applied Biosystems (Foster City, Calif.). Any other means for such synthesis known in the art may additionally or alternatively be employed. Suitable solid phase techniques, including automated synthesis techniques, are described in *Oligonucleotides and Analogues, a Practical Approach*, F. Eckstein, Ed., Oxford University Press, New York, 1991.

The synthesis of RNA and related analogs relative to the synthesis of DNA and related analogs has been increasing as efforts in RNA interference and micro RNA increase. The primary RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl] (FPMP), 2'-O-[(triisopropylsilyl)oxy]methyl (2'-O—$CH_2$—O—Si(iPr)$_3$ (TOM) and the 5'-O-silyl ether-T-ACE (5'-O-bis(trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. The primary groups being used for commercial RNA synthesis are: TBDMS: 5'-O-DMT-2'-O-t-butyldimethylsilyl; TOM: 2'-O-[(triisopropylsilyl)oxy]methyl; DOD/ACE: (5'-O-bis(trimethylsiloxy)cyclododecyloxysilyl ether-2'-O-bis(2-acetoxyethoxy)methyl; and FPMP: 5'-O-DMT-2'-O[1(2-fluorophenyl)-4-ethoxypiperidin-4-yl].

In certain embodiments, each of the aforementioned RNA synthesis strategies can be used herein. In certain embodiments, the aforementioned RNA synthesis strategies can be performed together in a hybrid fashion e.g. using a 5'-protecting group from one strategy with a 2'-O-protecting from another strategy.

As used herein the term "hybridization" includes the pairing of complementary strands of oligomeric compounds such as including the binding of an oligomeric compound as provided herein to a target nucleic acid. In certain embodiments, the mechanism of pairing involves hydrogen bonding, which may be Watson-Crick, Hoogsteen or reversed Hoogsteen hydrogen bonding, between complementary heterocyclic base moieties of nucleosides (or monomer subunits) that are in close enough proximity to hydrogen bond. For example, adenine and thymine are complementary nucleobases which pair through the formation of hydrogen bonds. Hybridization can occur under varying circumstances.

An oligomeric compound is specifically hybridizable when binding of the compound to the target nucleic acid interferes with the normal function of the target nucleic acid resulting in a loss of activity. To be specifically hybridizable also requires a sufficient degree of complementarity to avoid non-specific binding of the oligomeric compound to non-target nucleic acid sequences under the conditions in which specific binding is desired, i.e., under physiological conditions (for in vivo assays or therapeutic treatment) or other diagnostic conditions (for performing in vitro assays).

As used herein the term "complementary," refers to the capacity for precise pairing of two nucleobases regardless of where the two nucleobases are located. For example, if a nucleobase at a certain position of an oligomeric compound is capable of hydrogen bonding with a nucleobase at a certain position of a target nucleic acid, the target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between an oligomeric compound and its target nucleic acid.

It is understood in the art that the sequence of an oligomeric compound need not be 100% complementary to that of its target nucleic acid to be specifically hybridizable. Moreover, an oligomeric compound may hybridize over one or more segments such that intervening or adjacent segments are not involved in the hybridization event (e.g., a loop structure or hairpin structure). In certain embodiments, oligomeric compounds can comprise at least about 70%, at least about 80%, at least about 90%, at least about 95%, or at least about 99% sequence complementarity to a target region within the target nucleic acid sequence to which they are targeted. For example, an oligomeric compound in which 18 of 20 nucleobases of the oligomeric compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within this scope. Percent complementarity of an oligomeric compound with a region of a target nucleic acid can be determined routinely using BLAST programs (basic local alignment search tools) and PowerBLAST programs known in the art (Altschul et al., *J. Mol. Biol.*, 1990, 215, 403-410; Zhang and Madden, *Genome Res.*, 1997, 7, 649-656).

Further included herein are oligomeric compounds such as antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these oligomeric compounds may be introduced in the form of single-stranded, double-stranded, circular or hairpin oligomeric compounds and may contain structural elements such as internal or terminal bulges or loops. Once introduced to a system, the oligomeric compounds provided herein may elicit the action of one or more enzymes or structural proteins to effect modification of the target nucleic acid. Alternatively, the oligomeric compound may inhibit the activity the target nucleic acid through an occupancy-based method, thus interfering with the activity of the target nucleic acid.

One non-limiting example of such an enzyme is RNAse H, a cellular endonuclease which cleaves the RNA strand of an RNA:DNA duplex. It is known in the art that single-stranded oligomeric compounds which are "DNA-like" elicit RNase H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While one form of oligomeric compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

In certain embodiments, oligomeric compounds of the present invention bind and/or activate one or more nucleases. In certain embodiments, such binding and/or activation ultimately results in antisense activity. In certain embodiments, an oligomeric compound of the invention interacts with a target nucleic acid and with a nuclease, resulting in activation of the nuclease and cleavage of the target nucleic acid. In certain embodiments, an oligomeric compound of the invention interacts with a target nucleic acid and with a nuclease, resulting in activation of the nuclease and inactivation of the target nucleic acid. In certain embodiments, an oligomeric compound of the invention forms a duplex with a target nucleic acid and that duplex activates a nuclease, resulting in cleavage and/or inactivation of one or both of the oligomeric compound and the target nucleic acid. In certain embodiments, an oligomeric compound of the invention binds and/or activates a nuclease and the bound and/or activated nuclease cleaves or inactivates a target nucleic acid. Nucleases include, but are not limited to, ribonucleases (nucleases that specifically cleave ribonucleotides), double-strand nucleases (nucleases that specifically cleave one or both strands of a double-stranded duplex), and double-strand ribonucleases. For example, nucleases include, but are not limited to RNase H, an argonaute protein (including, but not limited to Ago2), and dicer.

In certain embodiments, oligomeric compounds of the present invention activate RNase H. RNase H is a cellular nuclease that cleaves the RNA strand of a duplex comprising an RNA strand and a DNA or DNA-like strand. In certain embodiments, an oligomeric compound of the present invention is sufficiently DNA-like to activate RNase H, resulting in cleavage of an RNA nucleic acid target. In certain such embodiments, the oligomeric compound comprises at least one region comprised of DNA or DNA-like nucleosides and one or more regions comprised of nucleosides that are otherwise modified. In certain embodiments, such otherwise modified nucleosides increase stability of the oligomeric compound and/or its affinity for the target nucleic acid. Certain such oligomeric compounds posses a desirable combination of properties. For example, certain such compounds, by virtue of the DNA or DNA-like region, are able to support RNase H activity to cleave a target nucleic acid; and by virtue of the otherwise modified nucleosides, have enhanced affinity for the target nucleic acid and/or enhanced stability (including resistance to single-strand-specific nucleases). In certain embodiments, such otherwise modified nucleosides result in oligomeric compounds having desired properties, such as metabolic profile and/or pharmacologic profile.

In certain embodiments, oligomeric compounds of the present invention interact with an argonaute protein (Ago). In certain embodiments, such oligomeric compounds first enter the RISC pathway by interacting with another member of the pathway (e.g., dicer). In certain embodiments, oligomeric compounds first enter the RISC pathway by interacting with Ago. In certain embodiments, such interaction ultimately results in antisense activity. In certain embodiments, the invention provides methods of activating Ago comprising contacting Ago with an oligomeric compound. In certain embodiments, such oligomeric compounds comprise a modified 5'-phosphate group. In certain embodiments, the invention provides methods of modulating the expression or amount of a target nucleic acid in a cell comprising contacting the cell with an oligomeric compound capable of activating Ago, ultimately resulting in cleavage of the target nucleic acid. In certain embodiments, the cell is in an animal. In certain embodiments, the cell is in vitro. In certain embodiments, the methods are performed in the presence of manganese. In certain embodiments, the manganese is endogenous. In certain embodiment the methods are performed in the absence of magnesium. In certain embodiments, the Ago is endogenous to the cell. In certain such embodiments, the cell is in an animal. In certain embodiments, the Ago is human Ago. In certain embodiments, the Ago is Ago2. In certain embodiments, the Ago is human Ago2.

In certain embodiments, oligomeric compounds of the present invention interact with the enzyme dicer. In certain such embodiments, oligomeric compounds bind to dicer and/or are cleaved by dicer. In certain such embodiments, such interaction with dicer ultimately results in antisense activity. In certain embodiments, the dicer is human dicer. In certain embodiments, oligomeric compounds that interact with dicer are double-stranded oligomeric compounds. In certain embodiments, oligomeric compounds that interact with dicer are single-stranded oligomeric compounds.

In embodiments in which a double-stranded oligomeric compound interacts with dicer, such double-stranded oligomeric compound forms a dicer duplex. In certain embodiments, any oligomeric compound described herein may be suitable as one or both strands of a dicer duplex. In certain embodiments, each strand of the dicer duplex is an oligomeric compound of the present invention. In certain embodiments, one strand of the dicer duplex is an oligomeric compound of the present invention and the other strand is any modified or unmodified oligomeric compound. In certain embodiments, one or both strands of a dicer duplex comprises a nucleoside of Formula II or a nucleoside of Formula IV at the 5' end. In certain embodiments, one strand of a dicer duplex is an antisense oligomeric compound and the other strand is its sense complement.

In certain embodiments, the dicer duplex comprises a 3'-overhang at one or both ends. In certain embodiments, such overhangs are additional nucleosides. In certain embodiments, the dicer duplex comprises a 3' overhang on the sense oligonucleotide and not on the antisense oligonucleotide. In certain embodiments, the dicer duplex comprises a 3' overhang on the antisense oligonucleotide and not on the sense oligonucleotide. In certain embodiments, 3' overhangs of a dicer duplex comprise 1-4 nucleosides. In certain embodiments, such overhangs comprise two nucleosides. In certain embodiments, the nucleosides in the 3'-overhangs comprise purine nucleobases. In certain embodiments, the nucleosides in the 3' overhangs comprise adenine nucleobases. In certain embodiments, the nucleosides in the 3' overhangs comprise pyrimidines. In certain embodiments, dicer duplexes comprising 3'-purine overhangs are more active as antisense compounds than dicer duplexes comprising 3' pyrimidine overhangs. In certain embodiments, oligomeric compounds of a dicer duplex comprise one or more 3' deoxy nucleosides. In certain such embodiments, the 3' deoxy nucleosides are dT nucleosides.

In certain embodiments, the 5' end of each strand of a dicer duplex comprises a phosphate moiety. In certain embodiments the antisense strand of a dicer duplex comprises a phosphate moiety and the sense strand of the dicer duplex does not comprise a phosphate moiety. In certain embodiments the sense strand of a dicer duplex comprises a phosphate moiety and the antisense strand of the dicer duplex does not comprise a phosphate moiety. In certain embodiments, a dicer duplex does not comprise a phosphate moiety at the 3' end. In certain embodiments, a dicer duplex is cleaved by dicer. In such embodiments, dicer duplexes do not comprise 2'-OMe modifications on the nucleosides at the cleavage site. In certain embodiments, such cleavage site nucleosides are RNA.

In certain embodiments, interaction of an oligomeric compound with dicer ultimately results in antisense activity. In certain embodiments, dicer cleaves one or both strands of a double-stranded oligomeric compound and the resulting product enters the RISC pathway, ultimately resulting in antisense activity. In certain embodiments, dicer does not cleave either strand of a double-stranded oligomeric compound, but nevertheless facilitates entry into the RISC pathway and ultimately results in antisense activity. In certain embodiments, dicer cleaves a single-stranded oligomeric compound and the resulting product enters the RISC pathway, ultimately resulting in antisense activity. In certain embodiments, dicer does not cleave the single-stranded oligomeric compound, but nevertheless facilitates entry into the RISC pathway and ultimately results in antisense activity.

In certain embodiments, the invention provides methods of activating dicer comprising contacting dicer with an oligomeric compound. In certain such embodiments, the dicer is in a cell. In certain such embodiments, the cell is in an animal.

In some embodiments, "suitable target segments" may be employed in a screen for additional oligomeric compounds that modulate the expression of a selected protein. "Modulators" are those oligomeric compounds that decrease or increase the expression of a nucleic acid molecule encoding a protein and which comprise at least an 8-nucleobase portion which is complementary to a suitable target segment. The screening method comprises the steps of contacting a suitable target segment of a nucleic acid molecule encoding a protein with one or more candidate modulators, and selecting for one or more candidate modulators which decrease or increase the expression of a nucleic acid molecule encoding a protein. Once it is shown that the candidate modulator or modulators are capable of modulating (e.g. either decreasing or increasing) the expression of a nucleic acid molecule encoding a peptide, the modulator may then be employed herein in further investigative studies of the function of the peptide, or for use as a research, diagnostic, or therapeutic agent. In the case of oligomeric compounds targeted to microRNA, candidate modulators may be evaluated by the extent to which they increase the expression of a microRNA target RNA or protein (as interference with the activity of a microRNA will result in the increased expression of one or more targets of the microRNA).

Suitable target segments may also be combined with their respective complementary oligomeric compounds provided herein to form stabilized double-stranded (duplexed) oligonucleotides. Such double stranded oligonucleotide moieties have been shown in the art to modulate target expression and regulate translation as well as RNA processing via an antisense mechanism. Moreover, the double-stranded moieties may be subject to chemical modifications (Fire et al., *Nature*, 1998, 391, 806-811; Timmons and Fire, *Nature*, 1998, 395, 854; Timmons et al., *Gene*, 2001, 263, 103-112; Tabara et al., *Science*, 1998, 282, 430-431; Montgomery et al., *Proc. Natl. Acad. Sci. USA*, 1998, 95, 15502-15507; Tuschl et al., *Genes Dev.*, 1999, 13, 3191-3197; Elbashir et al., *Nature*, 2001, 411, 494-498; Elbashir et al., *Genes Dev.*, 2001, 15, 188-200). For example, such double-stranded moieties have been shown to inhibit the target by the classical hybridization of antisense strand of the duplex to the target, thereby triggering enzymatic degradation of the target (Tijsterman et al., *Science*, 2002, 295, 694-697).

The oligomeric compounds provided herein can also be applied in the areas of drug discovery and target validation. In certain embodiments, provided herein is the use of the oligomeric compounds and targets identified herein in drug discovery efforts to elucidate relationships that exist between proteins and a disease state, phenotype, or condition. These methods include detecting or modulating a target peptide comprising contacting a sample, tissue, cell, or organism with one or more oligomeric compounds provided herein, measuring the nucleic acid or protein level of the target and/or a related phenotypic or chemical endpoint at some time after treatment, and optionally comparing the measured value to a non-treated sample or sample treated with a further oligomeric compound as provided herein. These methods can also be performed in parallel or in combination with other experiments to determine the function of unknown genes for the process of target validation or to determine the validity of a particular gene product as a target for treatment or prevention of a particular disease, condition, or phenotype. In certain embodiments, oligomeric compounds are provided for use in therapy. In certain embodiments, the therapy is reducing target RNA.

As used herein, the term "dose" refers to a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

In certain embodiments, chemically-modified oligomeric compounds are provided herein that may have a higher affinity for target RNAs than does non-modified DNA. In certain such embodiments, higher affinity in turn provides increased potency allowing for the administration of lower doses of such compounds, reduced potential for toxicity, improvement in therapeutic index and decreased overall cost of therapy.

Effect of nucleoside modifications on RNAi activity is evaluated according to existing literature (Elbashir et al., *Nature*, 2001, 411, 494-498; Nishikura et al., *Cell*, 2001, 107, 415-416; and Bass et al., *Cell*, 2000, 101, 235-238.)

In certain embodiments, oligomeric compounds provided herein can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway. In certain embodiments, oligomeric compounds provided herein can be utilized either alone or in combination with other oligomeric compounds or other therapeutics as tools in differential and/or combinatorial analyses to elucidate expression patterns of a portion or the entire complement of genes expressed within cells and tissues. Oligomeric compounds can also be effectively used as primers and probes under conditions favoring gene amplification or detection, respectively. These primers and probes are useful in methods requiring the specific detection of nucleic acid molecules encoding proteins and in the amplification of the nucleic acid molecules for detection or for use in further studies. Hybridization of oligomeric compounds as provided herein, particularly the primers and probes, with a nucleic acid can be detected by means known in the art. Such means may include conjugation of an enzyme to the oligonucleotide, radiolabelling of the oligonucleotide or any other suitable detection means. Kits using such detection means for detecting the level of selected proteins in a sample may also be prepared.

As one nonlimiting example, expression patterns within cells or tissues treated with one or more of the oligomeric compounds provided herein are compared to control cells or tissues not treated with oligomeric compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds and or oligomeric compounds which affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. USA*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (To, *Comb. Chem. High Throughput Screen*, 2000, 3, 235-41).

While in certain embodiments, oligomeric compounds provided herein can be utilized as described, the following examples serve only to illustrate and are not intended to be limiting.

EXAMPLES (GENERAL)

$^1$H and $^{13}$C NMR spectra were recorded on a 300 MHz and 75 MHz Bruker spectrometer, respectively.

Example 1

Synthesis of Nucleoside Phosphoramidites

The preparation of nucleoside phosphoramidites is performed following procedures that are illustrated herein and in the art such as but not limited to U.S. Pat. No. 6,426,220 and published PCT WO 02/36743.

Example 2

Synthesis of Oligomeric Compounds

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as alkylated derivatives and those having phosphorothioate linkages.

Oligomeric compounds: Unsubstituted and substituted phosphodiester (P=O) oligomeric compounds, including without limitation, oligonucleotides can be synthesized on an automated DNA synthesizer (Applied Biosystems model 394) using standard phosphoramidite chemistry with oxidation by iodine.

In certain embodiments, phosphorothioate internucleoside linkages (P=S) are synthesized similar to phosphodiester internucleoside linkages with the following exceptions: thiation is effected by utilizing a 10% w/v solution of 3,H-1,2-benzodithiole-3-one 1,1-dioxide in acetonitrile for the oxidation of the phosphite linkages. The thiation reaction step time is increased to 180 sec and preceded by the normal capping step. After cleavage from the CPG column and deblocking in concentrated ammonium hydroxide at 55° C. (12-16 hr), the oligomeric compounds are recovered by precipitating with greater than 3 volumes of ethanol from a 1 M NH$_4$OAc solution. Phosphinate internucleoside linkages can be prepared as described in U.S. Pat. No. 5,508,270.

Alkyl phosphonate internucleoside linkages can be prepared as described in U.S. Pat. No. 4,469,863.

3'-Deoxy-3'-methylene phosphonate internucleoside linkages can be prepared as described in U.S. Pat. No. 5,610,289 or 5,625,050.

Phosphoramidite internucleoside linkages can be prepared as described in U.S. Pat. No. 5,256,775 or U.S. Pat. No. 5,366,878.

Alkylphosphonothioate internucleoside linkages can be prepared as described in published PCT applications PCT/US94/00902 and PCT/US93/06976 (published as WO 94/17093 and WO 94/02499, respectively).

3'-Deoxy-3'-amino phosphoramidate internucleoside linkages can be prepared as described in U.S. Pat. No. 5,476,925.

Phosphotriester internucleoside linkages can be prepared as described in U.S. Pat. No. 5,023,243.

Borano phosphate internucleoside linkages can be prepared as described in U.S. Pat. Nos. 5,130,302 and 5,177,198.

Oligomeric compounds having one or more non-phosphorus containing internucleoside linkages including without limitation methylenemethylimino linked oligonucleosides, also identified as MMI linked oligonucleosides, methylenedimethylhydrazo linked oligonucleosides, also identified as MDH linked oligonucleosides, methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P=O or P=S linkages can be prepared as described in U.S. Pat. Nos. 5,378,825, 5,386,023, 5,489,677, 5,602,240 and 5,610,289.

Formacetal and thioformacetal internucleoside linkages can be prepared as described in U.S. Pat. Nos. 5,264,562 and 5,264,564.

Ethylene oxide internucleoside linkages can be prepared as described in U.S. Pat. No. 5,223,618.

Example 3

Isolation and Purification of Oligomeric Compounds

After cleavage from the controlled pore glass solid support or other support medium and deblocking in concentrated ammonium hydroxide at 55° C. for 12-16 hours, the oligomeric compounds, including without limitation oligonucleotides and oligonucleosides, are recovered by precipitation out of 1 M NH$_4$OAc with >3 volumes of ethanol. Synthesized oligomeric compounds are analyzed by electrospray mass spectroscopy (molecular weight determination) and by capillary gel electrophoresis. The relative amounts of phosphorothioate and phosphodiester linkages obtained in the synthesis is determined by the ratio of correct molecular weight relative to the −16 amu product (+/−32+/−48). For some studies oligomeric compounds are purified by HPLC, as described by Chiang et al., J. Biol. Chem. 1991, 266, 18162-18171. Results obtained with HPLC-purified material are generally similar to those obtained with non-HPLC purified material.

Example 4

Synthesis of Oligomeric Compounds using the 96 Well Plate Format

Oligomeric compounds, including without limitation oligonucleotides, can be synthesized via solid phase P(III) phosphoramidite chemistry on an automated synthesizer capable of assembling 96 sequences simultaneously in a 96-well format. Phosphodiester internucleoside linkages are afforded by oxidation with aqueous iodine. Phosphorothioate internucleoside linkages are generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites can be purchased from commercial vendors (e.g. PE-Applied Biosystems, Foster City, Calif., or Pharmacia, Piscataway, N.J.). Non-standard nucleosides are synthesized as per standard or patented methods and can be functionalized as base protected beta-cyanoethyldiisopropyl phosphoramidites.

Oligomeric compounds can be cleaved from support and deprotected with concentrated NH$_4$OH at elevated temperature (55-60° C.) for 12-16 hours and the released product then dried in vacuo. The dried product is then re-suspended in sterile water to afford a master plate from which all analytical and test plate samples are then diluted utilizing robotic pipettors.

Example 5

Analysis of Oligomeric Compounds Using the 96-Well Plate Format

The concentration of oligomeric compounds in each well can be assessed by dilution of samples and UV absorption spectroscopy. The full-length integrity of the individual products can be evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition is confirmed by mass analysis of the oligomeric compounds utilizing electrospray-mass spectroscopy. All assay test plates are diluted from the master plate using single and multi-channel robotic pipettors. Plates are judged to be acceptable if at least 85% of the oligomeric compounds on the plate are at least 85% full length.

Example 6

In Vitro Treatment of Cells with Oligomeric Compounds

The effect of oligomeric compounds on target nucleic acid expression is tested in any of a variety of cell types provided that the target nucleic acid is present at measurable levels. This can be routinely determined using, for example, PCR or Northern blot analysis. Cell lines derived from multiple tissues and species can be obtained from American Type Culture Collection (ATCC, Manassas, Va.).

The following cell type is provided for illustrative purposes, but other cell types can be routinely used, provided that the target is expressed in the cell type chosen. This can be readily determined by methods routine in the art, for example Northern blot analysis, ribonuclease protection assays or RT-PCR.

b.END cells: The mouse brain endothelial cell line b.END was obtained from Dr. Werner Risau at the Max Plank Institute (Bad Nauheim, Germany). b.END cells are routinely cultured in DMEM, high glucose (Invitrogen Life Technologies, Carlsbad, Calif.) supplemented with 10% fetal bovine serum (Invitrogen Life Technologies, Carlsbad, Calif.). Cells are routinely passaged by trypsinization and dilution when they reached approximately 90% confluence. Cells are seeded into 96-well plates (Falcon-Primaria #353872, BD Biosciences, Bedford, Mass.) at a density of approximately 3000 cells/well for uses including but not limited to oligomeric compound transfection experiments.

Experiments involving treatment of cells with oligomeric compounds:

When cells reach appropriate confluency, they are treated with oligomeric compounds using a transfection method as described.

LIPOFECTIN™

When cells reached 65-75% confluency, they are treated with one or more oligomeric compounds. The oligomeric compound is mixed with LiPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of the oligomeric compound(s) and a LIPOFECTIN™ concentration of 2.5 or 3 µg/mL per 100 nM oligomeric compound(s). This transfection mixture is incubated at room temperature for approximately 0.5 hours. For cells grown in 96-well plates, wells are washed once with 100 µL OPTI-MEM™-1 and then treated with 130 µL of the transfection mixture. Cells grown in 24-well plates or other standard tissue culture plates are treated similarly, using appropriate volumes of medium and oligomeric compound(s). Cells are treated and data are obtained in duplicate or triplicate. After approximately 4-7 hours of treatment at 37° C., the medium containing the transfection mixture is replaced with fresh culture medium. Cells are harvested 16-24 hours after treatment with oligomeric compound(s).

Other suitable transfection reagents known in the art include, but are not limited to, CYTOFECTIN™, LipOFECTAMINE™, OLIGOFECTAMINE™, and FUGENE™. Other suitable transfection methods known in the art include, but are not limited to, electroporation.

Example 7

Real-Time Quantitative PCR Analysis of Target mRNA Levels

Quantitation of target mRNA levels is accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

RT and PCR reagents are obtained from Invitrogen Life Technologies (Carlsbad, Calif.). RT, real-time PCR is carried out by adding 20 µL PCR cocktail (2.5×PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction is carried out by incubation for 30 minutes at 48° C. Following a 10 minute incubation at 95° C. to activate the PLATINUM® Taq, 40 cycles of a two-step PCR protocol are carried out: 95° C. for 15 seconds (denaturation) followed by 60° C. for 1.5 minutes (annealing/extension).

Gene target quantities obtained by RT, real-time PCR are normalized using either the expression level of GAPDH, a gene whose expression is constant, or by quantifying total RNA using RIBOGREEN™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RIBOGREEN™ are taught in Jones, L. J., et al, (Analytical Biochemistry, 1998, 265, 368-374).

In this assay, 170 µL of RIBOGREEN™ working reagent (RIBOGREEN™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Example 8

Analysis of Oligonucleotide Inhibition of Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR. Real-time quantitative PCR is presently desired. RNA analysis can be performed on total cellular RNA or poly(A)+ mRNA. One method of RNA analysis of the present disclosure is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Methods for preparation of polyclonal antisera are taught in, for example, Ausubel, F. M. et al., Current Protocols in Molecular Biology, Volume 2, pp. 11.12.1-11.12.9, John Wiley & Sons, Inc., 1997. Preparation of monoclonal antibodies is taught in, for example, Ausubel, F. M. et al., Current Protocols in Molecular Biology, Volume 2, pp. 11.4.1-11.11.5, John Wiley & Sons, Inc., 1997.

Immunoprecipitation methods are standard in the art and can be found at, for example, Ausubel, F. M. et al., Current Protocols in Molecular Biology, Volume 2, pp. 10.16.1-10.16.11, John Wiley & Sons, Inc., 1998. Western blot (immunoblot) analysis is standard in the art and can be found at, for example, Ausubel, F. M. et al., Current Protocols in Molecular Biology, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., Current Protocols in Molecular Biology, Volume 2, pp. 11.2.1-11.2.22, John Wiley & Sons, Inc., 1991.

Example 9

Design of Phenotypic Assays and In Vivo Studies for the Use of Target Inhibitors Phenotypic Assays Once target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the target inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

Example 10

RNA Isolation

Poly(A)+ mRNA Isolation

Poly(A)+ mRNA is isolated according to Miura et al., (Clin. Chem., 1996, 42, 1758-1764). Other methods for poly (A)+ mRNA isolation are routine in the art. Briefly, for cells grown on 96-well plates, growth medium is removed from the cells and each well is washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) is added to each well, the plate is gently agitated and then incubated at room temperature for five minutes. 55 µL of lysate is transferred to Oligo d(T) coated 96-well plates (AGCT Inc., Irvine Calif.). Plates are incubated for 60 minutes at room temperature, washed 3 times with 200 µL of wash buffer (10 mM Tris-HCl pH 7.6, 1 mM EDTA, 0.3 M NaCl). After the final wash, the plate is blotted on paper towels to remove excess wash buffer and then air-dried for 5 minutes. 60 µL of elution buffer (5 mM Tris-HCl pH 7.6), preheated to 70° C., is added to each well, the plate is incubated on a 90° C. hot plate for 5 minutes, and the eluate is then transferred to a fresh 96-well plate.

Cells grown on 100 mm or other standard plates may be treated similarly, using appropriate volumes of all solutions.

Total RNA Isolation

Total RNA is isolated using an RNEASY 96™ kit and buffers purchased from Qiagen Inc. (Valencia, Calif.) following the manufacturer's recommended procedures. Briefly, for cells gown on 96-well plates, growth medium is removed from the cells and each well is washed with 200 µL cold PBS. 150 µL Buffer RLT is added to each well and the plate vigorously agitated for 20 seconds. 150 µL of 70% ethanol is then added to each well and the contents mixed by pipetting three times up and down. The samples are then transferred to the RNEASY 96™ well plate attached to a QIAVAC™ manifold fitted with a waste collection tray and attached to a vacuum source. Vacuum is applied for 1 minute. 500 µL of Buffer RW1 is added to each well of the RNEASY 96™ plate and incubated for 15 minutes and the vacuum is again applied for 1 minute. An additional 500 µL of Buffer RW1 is added to each well of the RNEASY 96™ plate and the vacuum is applied for 2 minutes. 1 mL of Buffer RPE is then added to each well of the RNEASY 96™ plate and the vacuum applied for a period of 90 seconds. The Buffer RPE wash is then repeated and the vacuum is applied for an additional 3 minutes. The plate is then removed from the QIAVAC™ manifold and blotted dry on paper towels. The plate is then re-attached to the QIAVAC™ manifold fitted with a collection tube rack containing 1.2 mL collection tubes. RNA is then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 11

Target-Specific Primers and Probes

Probes and primers may be designed to hybridize to a target sequence, using published sequence information.

For example, for human PTEN, the following primer-probe set was designed using published sequence information (GENBANK™ accession number U92436.1, SEQ ID NO: 1).

```
Forward primer:
AATGGCTAAGTGAAGATGACAATCAT      (SEQ ID NO: 2)

Reverse primer:
TGCACATATCATTACACCAGTTCGT       (SEQ ID NO: 3)
```

And the PCR probe:
FAM-TTGCAGCAATTCACTGTAAAGCTG-GAAAGG-TAMRA (SEQ ID NO: 4), where FAM is the fluorescent dye and TAMRA is the quencher dye.

Example 12

Western Blot Analysis of Target Protein Levels

Western blot analysis (immunoblot analysis) is carried out using standard methods. Cells are harvested 16-20 h after oligonucleotide treatment, washed once with PBS, suspended in Laemmli buffer (100 µl/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

Example 13

Preparation of Compound 3

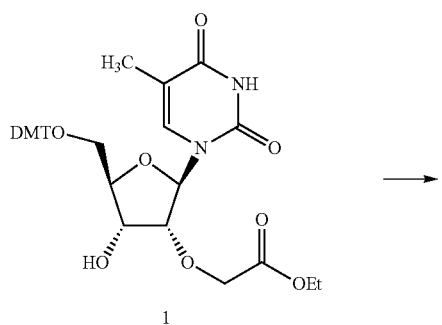

1

-continued

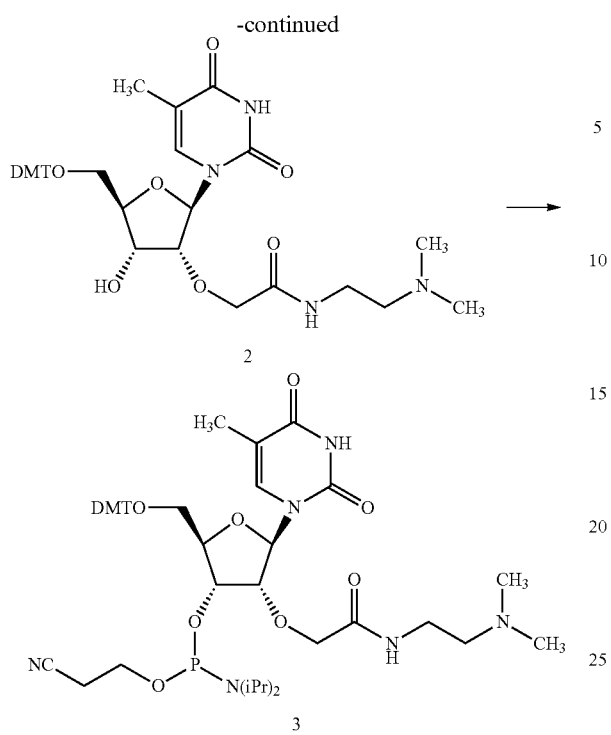

a) Preparation of Compound 2

Compound 1 was prepared according to published literature (Prakash et al., *Org. Let.* 2003, 5, 403-406) using ethyl-2-bromoacetate for alkylation. Compound 1 (5.378 g, 8.50 mmol) was dissolved in anhydrous THF (66 mL). To this was added N,N-dimethylethylenediamine (18.7 mL, 170 mmol) and the reaction mixture was stirred at ambient temperature. After 6 h, toluene (80 mL) was added and the solvent was evaporated in vacuo to give Compound 2 as a white foam (6.12 g, 95%). $^1$H NMR (CDCl$_3$): δ 7.64 (s, 3H), 7.41-6.79 (m, 13H), 5.94 (d, 1H, J$_{1',2'}$=2.4 Hz), 4.41 (m, 1H), 4.31 (q ab, 2H), 4.19 (m, 1H), 3.95 (m, 1H), 3.75 (s, 6H), 3.52 (m, 2H), 2.75 (m, 2H), 2.48 (m, 2H), 2.24 (s, 6H), 1.36 (s, 3H). $^{13}$C NMR (CDCl$_3$): δ 170.1, 164.7, 158.7, 151.0, 144.4, 135.5, 135.3, 134.9, 130.1, 129.0, 128.1, 127.7, 127.1, 113.3, 110.9, 88.5, 86.7, 84.8, 83.3, 70.7, 68.2, 61.8, 58.4, 45.4, 36.0, 12.0. HRMS (MALDI) calcd for C$_{37}$H$_{44}$N$_4$O$_9$+Na$^+$: 711.3006. Found: 711.3001. TLC: CH$_2$Cl$_2$-EtOAc-MeOH-NEt$_3$, 64:21:21:5, v/v/v/v; R$_f$ 0.4.

b) Preparation of Compound 3

Compound 2 (5.754 g, 8.35 mmol) was dried by coevaporation with anhydrous pyridine (2×75 mL) and then dissolved in CH$_2$Cl$_2$ (60 mL). To this solution, diisopropylamine tetrazolide (715 mg, 4.18 mmol) and 2-cyanoethyl-N,N,N',N'-tetraisopropylphosphordiamidite (3.18 mL, 10.02 mmol) were added. After 13 h, EtOAc (420 mL) was added and about 60 mL of solvent was evaporated in vacuo. The organic was washed with half-saturated NaHCO$_3$ (3×80 mL), then with brine (2×40 mL), dried over MgSO$_4$, filtered an evaporated in vacuo at 27° C. to give an oil. The resulting residue was coevaporated with toluene (2×300 mL) to give a foam which was then dissolved in CH$_2$Cl$_2$ (20 mL). Hexanes (1000 mL) were slowly added to the rapidly stirred solution via an addition funnel to yield a wax and the supernatant was decanted. The wax was washed with hexanes thrice and the washes were decanted. The precipitation was repeated one more time to give a white wax which was dried in vacuo at ambient temperature to give Compound 3 as a foam (6.60 g, 89%). LRMS (ES): m/z 889 (M+H$^+$), 911 (M+Na$^+$). $^{31}$P NMR (CDCl$_3$): δ 151.5, 151.0.

Compound 3 was incorporated into oligonucleotides according to standard solid phase synthesis procedures. Phosphorylation at the 5' end of oligonucleotides was achieved during synthesis by using Glen Research (Sterling, Va.) chemical phosphorylation reagent.

Example 14

Preparation of Compound 4

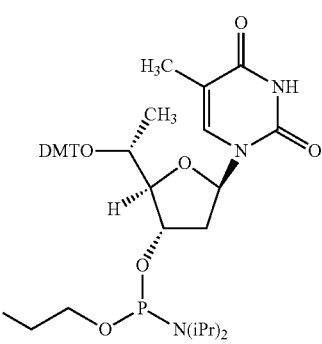

Compound 4 was prepared according to the procedures described in published patent application WO 94/22890. Compound 4 was incorporated into oligonucleotides according to standard solid phase synthesis procedures. Phosphorylation at the 5' end of oligonucleotides was achieved during synthesis by using Glen Research (Sterling, Va.) chemical phosphorylation reagent.

Example 15

Preparation of Compound 13

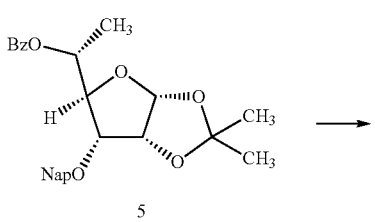

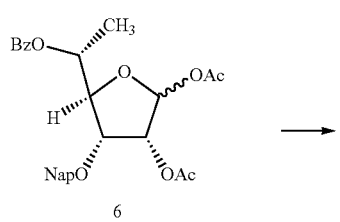

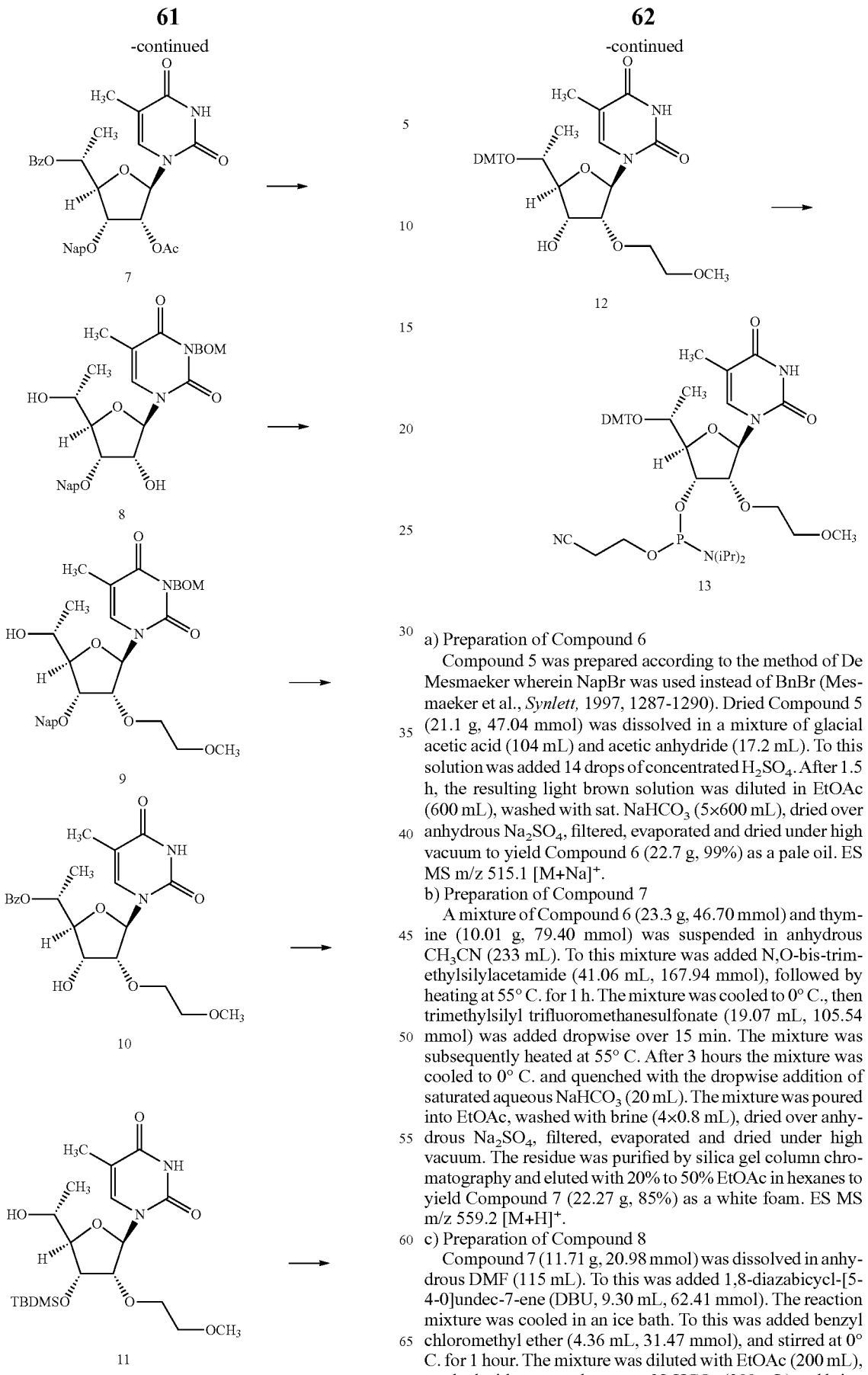

a) Preparation of Compound 6

Compound 5 was prepared according to the method of De Mesmaeker wherein NapBr was used instead of BnBr (Mesmaeker et al., *Synlett,* 1997, 1287-1290). Dried Compound 5 (21.1 g, 47.04 mmol) was dissolved in a mixture of glacial acetic acid (104 mL) and acetic anhydride (17.2 mL). To this solution was added 14 drops of concentrated $H_2SO_4$. After 1.5 h, the resulting light brown solution was diluted in EtOAc (600 mL), washed with sat. $NaHCO_3$ (5×600 mL), dried over anhydrous $Na_2SO_4$, filtered, evaporated and dried under high vacuum to yield Compound 6 (22.7 g, 99%) as a pale oil. ES MS m/z 515.1 $[M+Na]^+$.

b) Preparation of Compound 7

A mixture of Compound 6 (23.3 g, 46.70 mmol) and thymine (10.01 g, 79.40 mmol) was suspended in anhydrous $CH_3CN$ (233 mL). To this mixture was added N,O-bis-trimethylsilylacetamide (41.06 mL, 167.94 mmol), followed by heating at 55° C. for 1 h. The mixture was cooled to 0° C., then trimethylsilyl trifluoromethanesulfonate (19.07 mL, 105.54 mmol) was added dropwise over 15 min. The mixture was subsequently heated at 55° C. After 3 hours the mixture was cooled to 0° C. and quenched with the dropwise addition of saturated aqueous $NaHCO_3$ (20 mL). The mixture was poured into EtOAc, washed with brine (4×0.8 mL), dried over anhydrous $Na_2SO_4$, filtered, evaporated and dried under high vacuum. The residue was purified by silica gel column chromatography and eluted with 20% to 50% EtOAc in hexanes to yield Compound 7 (22.27 g, 85%) as a white foam. ES MS m/z 559.2 $[M+H]^+$.

c) Preparation of Compound 8

Compound 7 (11.71 g, 20.98 mmol) was dissolved in anhydrous DMF (115 mL). To this was added 1,8-diazabicycl-[5-4-0]undec-7-ene (DBU, 9.30 mL, 62.41 mmol). The reaction mixture was cooled in an ice bath. To this was added benzyl chloromethyl ether (4.36 mL, 31.47 mmol), and stirred at 0° C. for 1 hour. The mixture was diluted with EtOAc (200 mL), washed with saturated aqueous $NaHCO_3$ (200 mL) and brine (200 mL) then dried (Na$_2$SO$_4$), filtered and evaporated. The residue obtained was dissolved in methanol (89 mL) and K$_2$CO$_3$ (8.76 g, 63.40 mmol). The reaction mixture was stirred at room temperature for 1 h. The mixture was poured into EtOAc (200 mL), washed with water (200 mL) and brine (200 mL), dried over anhydrous Na$_2$SO$_4$, filtered and evaporated. The residue was purified by silica gel column chromatography and eluted with 5% methanol in CH$_2$Cl$_2$ to yield Compound 8 (8.93 g, 80%) as a white foam. ES MS m/z 533.2 [M+H]$^+$.

d) Preparation of Compound 9

Compound 8 (4.30 g, 8.07 mmol) was dried over P$_2$O$_5$ under reduced pressure and dissolved in anhydrous DMF (24 mL). The mixture was cooled to −20° C. To this was added NaH (0.48 g, 12.11 mmol, 60% dispersion in mineral oil) with stirring for 30 minutes followed by addition of 1-methoxy-2-iodoethane (2.25 g, 12.11 mmol). The reaction mixture was warmed up to 0° C. After stirring for 1.5 h at 0° C. the reaction mixture was cooled to −20° C. and additional NaH (0.48 g, 12.11 mmol, 60% dispersion in mineral oil) was added. Stirring was continued at −20° C. for 30 minutes and 1-methoxy-2-iodoethane (2.25 g, 12.11 mmol) was added. The reaction mixture was warmed to 0° C. and with stirring for an additional 1.5 h. The reaction was quenched with methanol (5 mL), diluted with EtOAc (100 mL), washed with water (100 mL) and brine (100 mL), dried over Na$_2$SO$_4$, filtered and evaporated under reduced pressure. The residue was purified by silica gel column chromatography and eluted with 5% methanol in CH$_2$Cl$_2$ to yield Compound 9 (2.95 g, 62%). ES MS m/z 591.2 [M+H]$^+$.

e) Preparation of Compound 10

Compound 9 (2.2 g, 3.73 mmol) was dissolved in anhydrous pyridine (7 mL) and cooled in an ice bath. To this benzoyl chloride (0.88 mL, 7.61 mmol) was added and once the addition was over, reaction mixture was allowed to come to room temperature. The reaction mixture was stirred at room temperature for 4 h under an argon atmosphere and subsequently cooled the reaction mixture in an ice bath and quenched by adding saturated aqueous NaHCO$_3$ (5 mL). Diluted the reaction mixture with EtOAc (50 mL) and washed with saturated aqueous NaHCO$_3$ (2×50 mL), brine (50 mL), dried over Na$_2$SO$_4$, filtered and concentrated. The residue obtained was dissolved in CH$_2$Cl$_2$ (40 mL) and added 2,4-dichloro-5,6-dicyano-1,4-benzoquinone (DDQ, 1.93 g, 8.5 mmol) and H$_2$O (0.15 mL, 8.5 mmol) and stirred at room temperature. After 18 h, diluted the reaction mixture with EtOAc (60 mL), washed with saturated aqueous NaHCO$_3$ (2×80 mL), brine (50 mL), dried over Na$_2$SO$_4$, filtered and evaporated under reduced pressure. The residue was dissolved in MeOH (30 mL) and palladium hydroxide (1.1 g, 20 wt % Pd on carbon dry base) and stirred under H$_2$ atmosphere for 6 h. To this acetic acid (0.56 mL) was added and stirred for 5 min. The reaction mixture was filtered through a pad of celite 545, and washed the celite with copious amount of MeOH. The combined filtrate and washing were concentrated under reduced pressure and the residue was purified by silica gel column chromatography and eluted with 5% methanol in CH$_2$Cl$_2$ to yield Compound 10 (1.43 g, 88%). ES MS m/z 435.1 [M+H]$^+$.

f) Preparation of Compound 11

A mixture of Compound 10 (1.33 g, 3.06 mmol) and imidazole (2.09, 30.70 mmol) was dissolved in anhydrous DMF (11.4 mL). To this solution tert-butyldimethylsilyl chloride (2.31 g, 15.33 mmol) was added with stirring at room temperature for 16 h under an atmosphere of argon. The reaction mixture was diluted with EtOAc (75 mL) and washed with saturated aqueous NaHCO$_3$ (2×60 mL) and brine (50 mL), dried over Na$_2$SO$_4$, filtered and concentrated. The residue obtained was dissolved in methanolic ammonia (20 mL, 7M) and stirred for 24 h at 55° C. The solvent was removed under reduced pressure and the residue was purified by silica gel column chromatography and eluted with 50% EtOAc in hexanes to yield Compound 11 (1.21 g, 89%). ES MS m/z 455.2 [M+H]$^+$.

g) Preparation of Compound 12

Compound 11 (0.42 g, 0.96 mmol) was mixed with 4,4'-dimethoxytrityl chloride (0.82 g, 2.41 mmol) and dried over P$_2$O$_5$ under reduced pressure. The mixture was dissolved in anhydrous pyridine (3 mL) and stirred at 45° C. for 18 h under an atmosphere of argon. The reaction mixture was cooled to room temperature and diluted with EtOAc (40 mL) and washed with saturated aqueous NaHCO$_3$ (60 mL) and brine (40 mL), dried over Na$_2$SO$_4$, filtered and concentrated. The residue obtained was purified by silica gel column chromatography and eluted first with 50% EtOAc in hexanes and then with 5% methanol in CH$_2$Cl$_2$. The product obtained was dissolved in a mixture of triethylamine trihydrofluoride (1.38 mL, 8.44 mmol) and triethylamine (0.58 mL, 4.22 mmol) in THF (8.4 mL). After 72 h the mixture was diluted with EtOAc (60 mL), washed with water (40 mL), saturated aqueous NaHCO$_3$ (40 mL) and brine (40 mL) then dried over Na$_2$SO$_4$, filtered and evaporated. The residue obtained was purified by silica gel column chromatography and eluted with 70% EtOAc in hexanes to yield Compound 12 (0.44 g, 73%). ES MS m/z 631.2 [M+H]$^+$.

h) Preparation of Compound 13

Compound 12 (0.35 g, 0.55 mmol) was dried over P$_2$O$_5$ under reduced pressure then dissolved in anhydrous DMF (1.8 mL). To this 1-H-tetrazole (0.033 mg, 0.48 mmol), N-methylimidazole (0.012 mL, 0.15 mmol) and 2-cyanoethyl-N,N,N',N'-tetraisopropylphosphordiamidite (0.27 mL, 0.86 mmol) were added. After 3 h, EtOAc (40 mL) was added and the mixture was washed with saturated NaHCO$_3$ (30 mL) and brine (40 mL), dried over anhydrous Na$_2$SO$_4$, filtered and evaporated in vacuo to give an oil. The oily residue was purified by silica gel column chromatography by eluting with EtOAc/hexane (1:1) to yield Compound 13 (0.38 g, 83%) as a white foam. MS (ES): m/z 831 [M+H]$^+$; $^{31}$P NMR (121 MHz, CDCl$_3$): δ 150.2, 149.

Example 16

Preparation of Compound 22

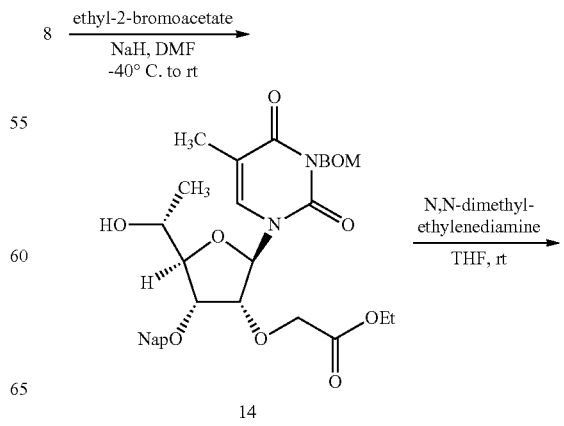

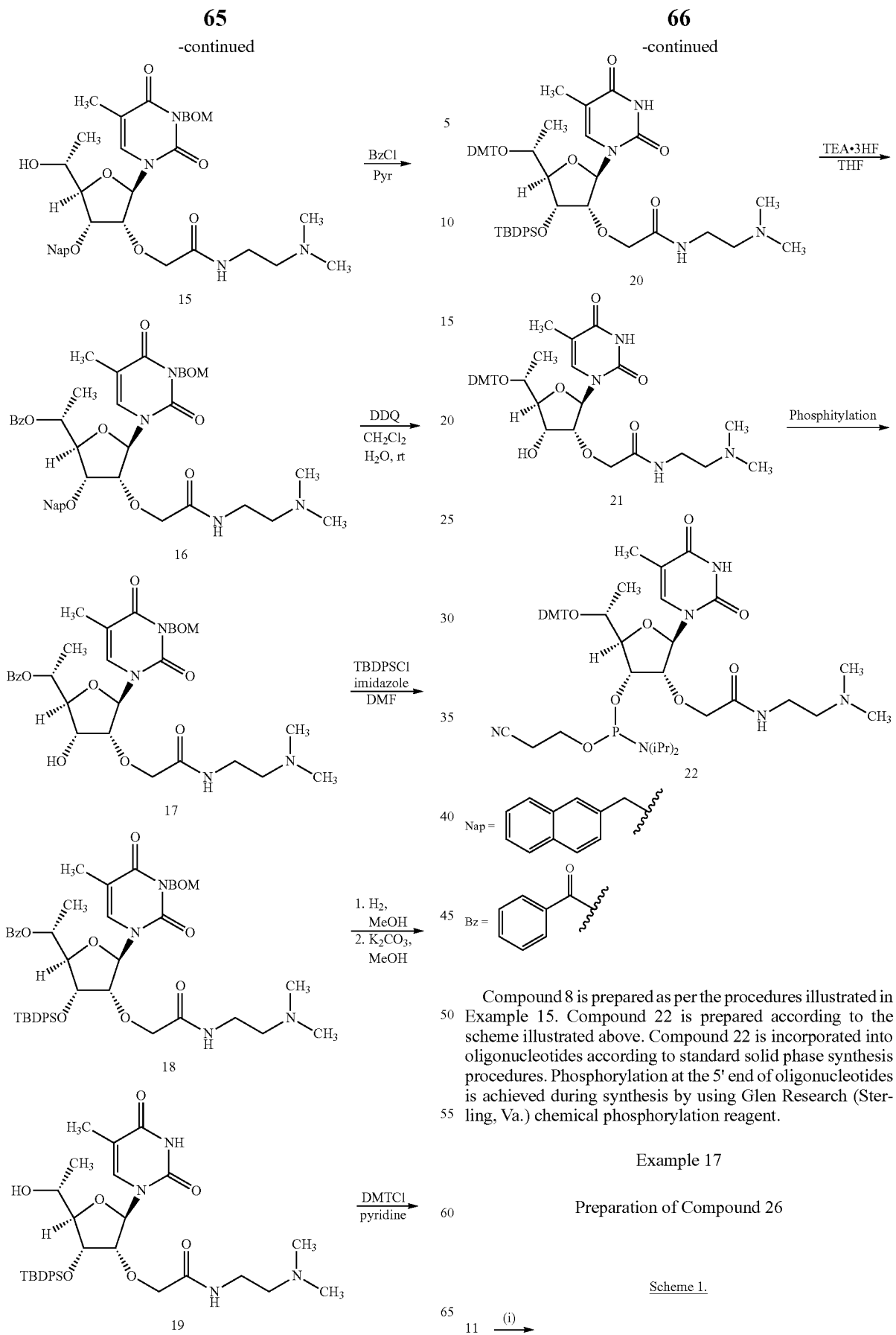

Compound 8 is prepared as per the procedures illustrated in Example 15. Compound 22 is prepared according to the scheme illustrated above. Compound 22 is incorporated into oligonucleotides according to standard solid phase synthesis procedures. Phosphorylation at the 5' end of oligonucleotides is achieved during synthesis by using Glen Research (Sterling, Va.) chemical phosphorylation reagent.

Example 17

Preparation of Compound 26

Scheme 1.

11 (i)→

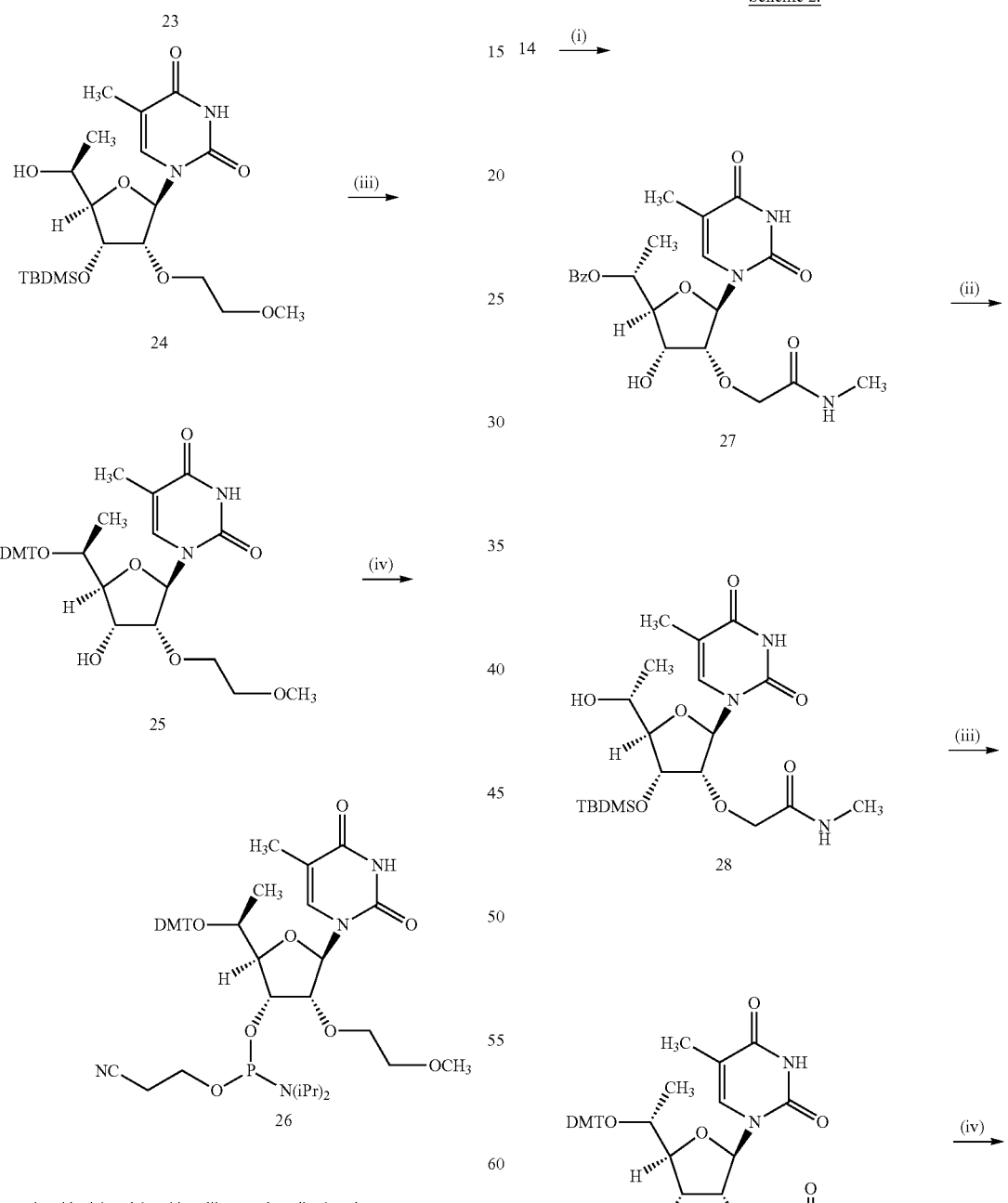
Compound 11 is prepared as per the procedures illustrated in Example 15.
Example 18
Preparation of Compound 30
Scheme 2.
(i) 4-nitrobenzoic acid, triphenylphosphine, diisopropyl azodicarboxylate, rt; (ii) NH₃, MeOH, 55° C.; (iii) a. DMTCl, pyridine, 45° C., b. THF•3HF, TEA, THF; (iv) 2-cyanoethyl-N,N,N′N′-tetraisopropylphosphordiamidite, 1-H-tetrazole, N-methyl-imidazole, DMF.

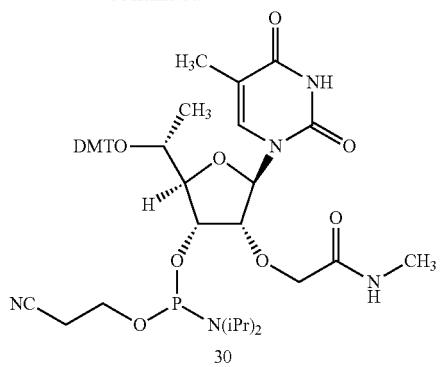

Nap: 2-methylnaphthalene; Bz: benzoyl; TBDMS: tert-butyldimethylsilyl; (i) DMF, 2-bromoethyl acetate, NaH; (ii) a. aqueous CH₃NH₂, THF, b. BzCl, pyridine, rt, c. DDQ, CH₂Cl₂, H₂O, rt, c. Pd(OH)₂, MeOH, H₂, AcOH; (iii) a. TBDMSCl, Im, DMF, rt, b. NH₃, MeOH, 55° C.; (iv) a. DMTCl, Py, 45° C., b. TEA•3HF, TEA, THF; (v) 2-cyanoethyl-N,N,N′N′-tetraisopropyl-phosphordiamidite, 1-H-tetrazole, N-methylimidazole, DMF.

Compound 14 is prepared as per the procedures illustrated in Example 16.

Example 19

Preparation of Compound 34

Scheme 3.

28 $\xrightarrow{(i)}$

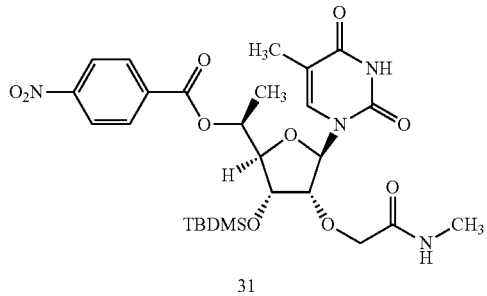

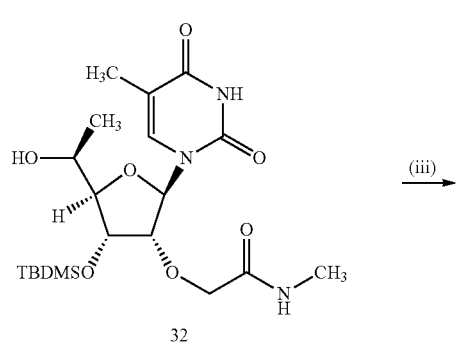

(i) 4-nitrobenzoic acid, triphenylphosphine, diisopropyl azodicarboxylate, rt;
(ii) NH₃, MeOH, 55° C.; (iii) a. DMTCl, pyridine, 45° C., b. TEA•3HF, TEA, THF; (iv) 2-cyanoethyl-N,N,N′N′-tetraisopropylphosphordiamidite, 1-H-tetrazole, N-methylimidazole, DMF.

Compound 28 is prepared as per the procedures illustrated in Example 18.

Example 20

Preparation of Compound 37

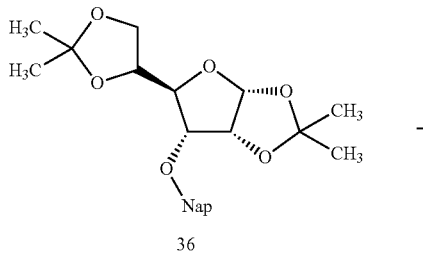

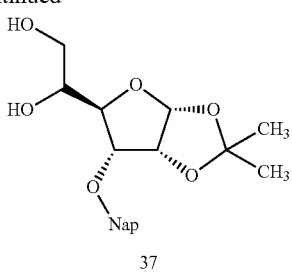

37 a) Preparation of Compound 36

Commercially available 1,2;5,6-di-O-isopropylidene-α-D-allofuranose, Compound 35, (135 g, 519.0 mmol) and 2-(bromomethyl)-naphthalene (126 g, 570.0 mmol) were dissolved in DMF (500 mL) in a three-necked flask (500 mL) and the reaction was cooled in an ice bath. Sodium hydride (60% w/w, 29 g, 727.0 mmol) was carefully added (6 g portions every 10 minutes) to the reaction and the stirring was continued for another 60 minutes after the addition was complete. At this time TLC analysis showed no more sugar (Compound 35). The reaction was carefully poured onto crushed ice (ca. 500 g) and the resulting slurry was stirred vigorously until all the ice melted. The resulting off-white solid was collected by filtration and suspended in water. The suspension was stirred vigorously using a mechanical stirrer for 30 minutes after which the solid was collected by filtration and suspended in hexanes. The suspension was stirred vigorously for 30 minutes after which the solid was collected by filtration and air dried for 4-6 hours and then dried under high vacuum over $P_2O_5$ for 16 hours to provide Compound 36 (206.0 g, 99%) as an off-white solid. $^1$H NMR (300 MHz, CDCl$_3$) δ: 7.85 (m, 4H), 7.48 (m, 3H), 5.74 (s, 1H), 4.92 (d, 1H, J=11.7), 4.75 (d, 1H, J=11.6), 4.58 (m, 1H), 4.36 (m, 1H), 4.15 (m, 1H), 4.03-3.86 (m, 3H), 1.61 (s, 3H), 1.36 (s, 9H).

b) Preparation of Compound 37

Compound 36 (200.0 g, 0.5 moles) was added in small portions to a solution of acetic acid (2.2 L) and water (740 mL). The reaction was stirred at room temperature for 16 h after which, TLC analysis (30% EtOAc/hexanes) indicated complete consumption of Compound 36. The reaction was then concentrated under reduced pressure until most of the acetic acid was removed. The remaining solution was poured into a stirred mixture of EtOAc (1 L) and water (1 L). Solid KOH was then added to the above mixture until the aqueous layer was strongly basic (pH>12). The organic layer was then separated, washed with saturated sodium bicarbonate solution and brine then dried (Na$_2$SO$_4$), filtered and concentrated under reduced pressure to provide Compound 37 as a yellow foam, which was used without any further purification.

Example 21

Preparation of Compound 45

37 →(TBDPSCl, pyr, rt, 63%)

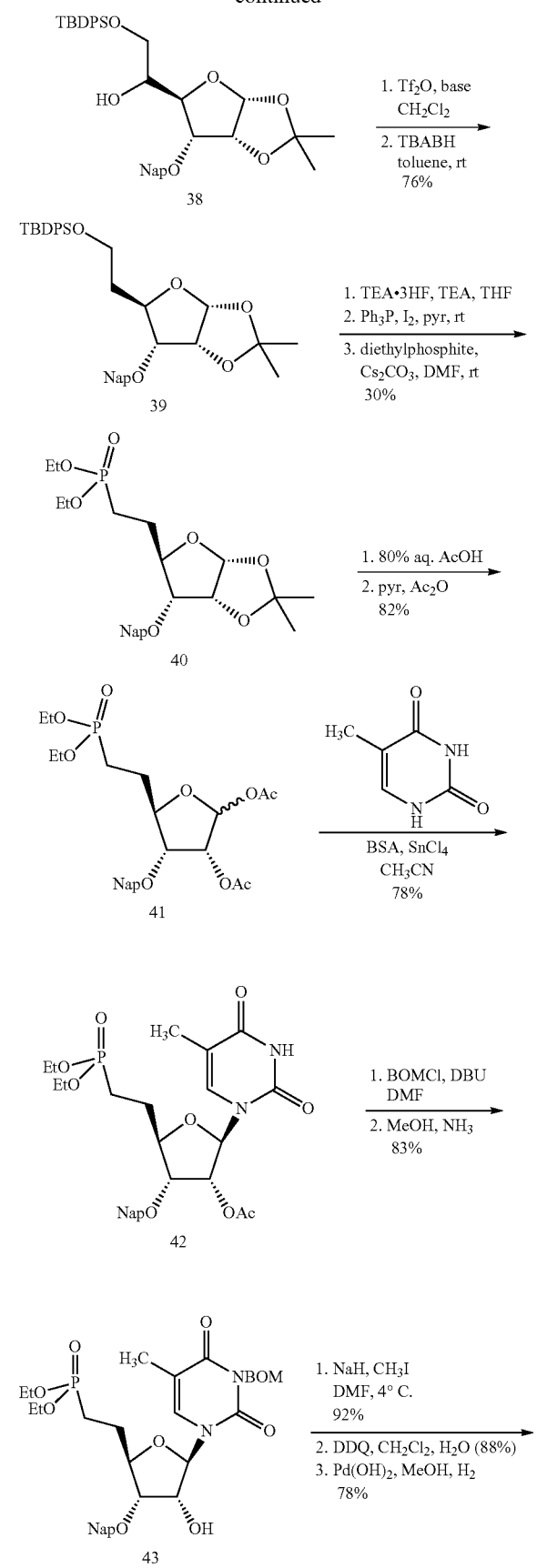

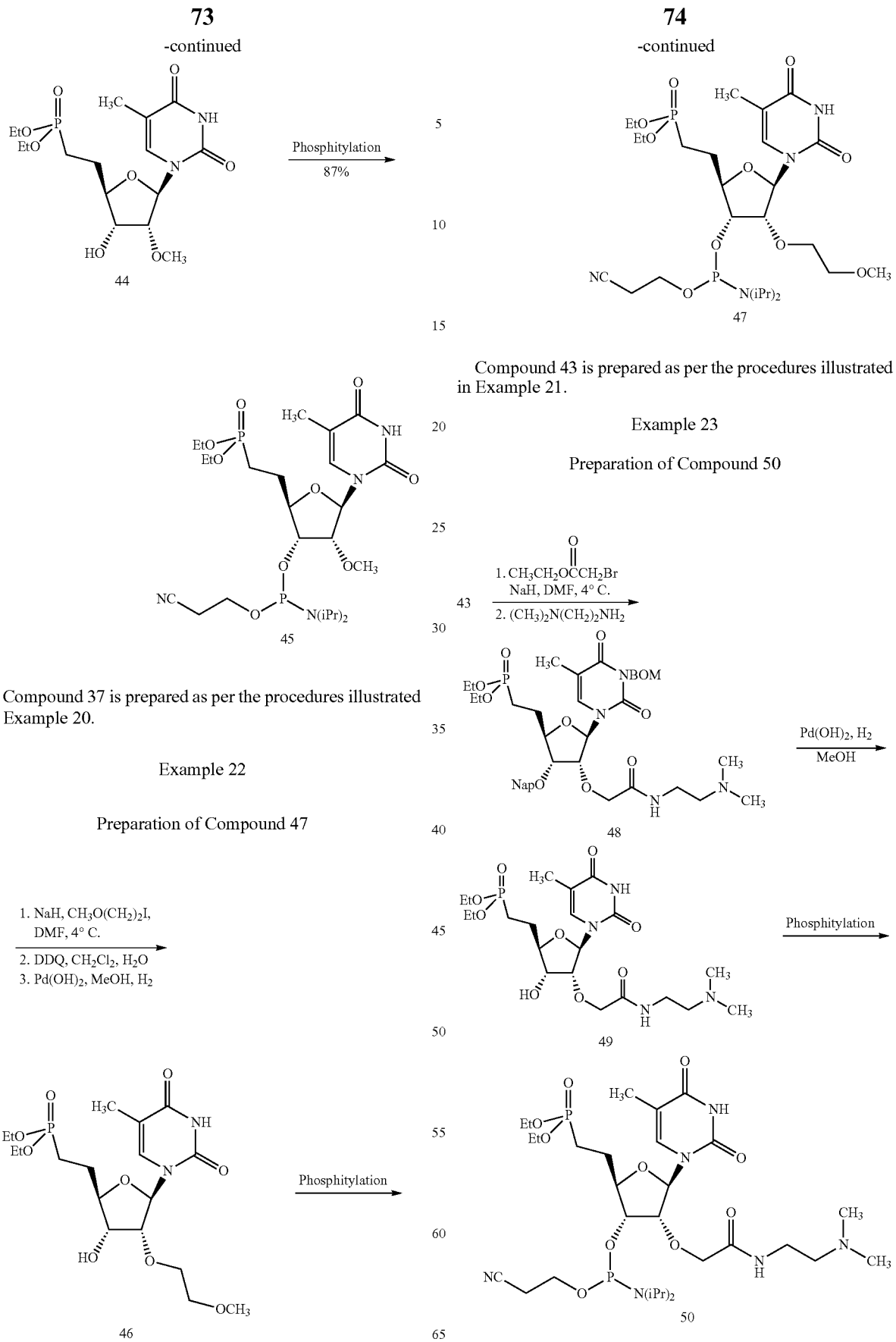

Example 24
Preparation of Compound 53
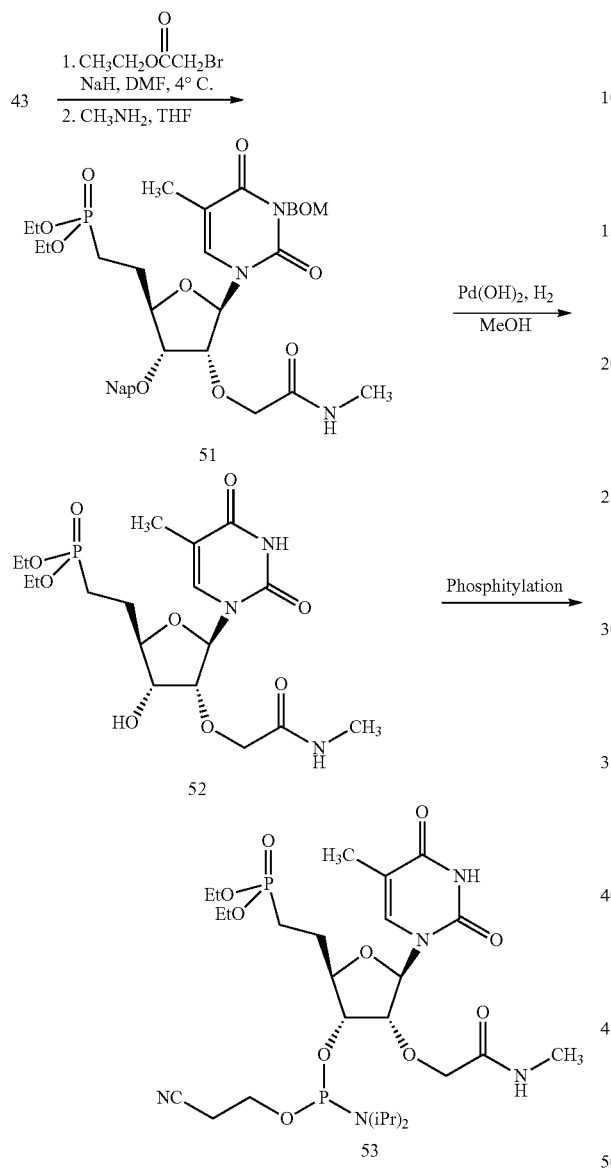
Compound 43 is prepared as per the procedures illustrated in Example 21.
Example 25
Preparation of Compound 57
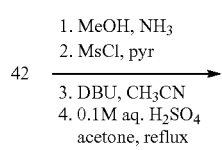
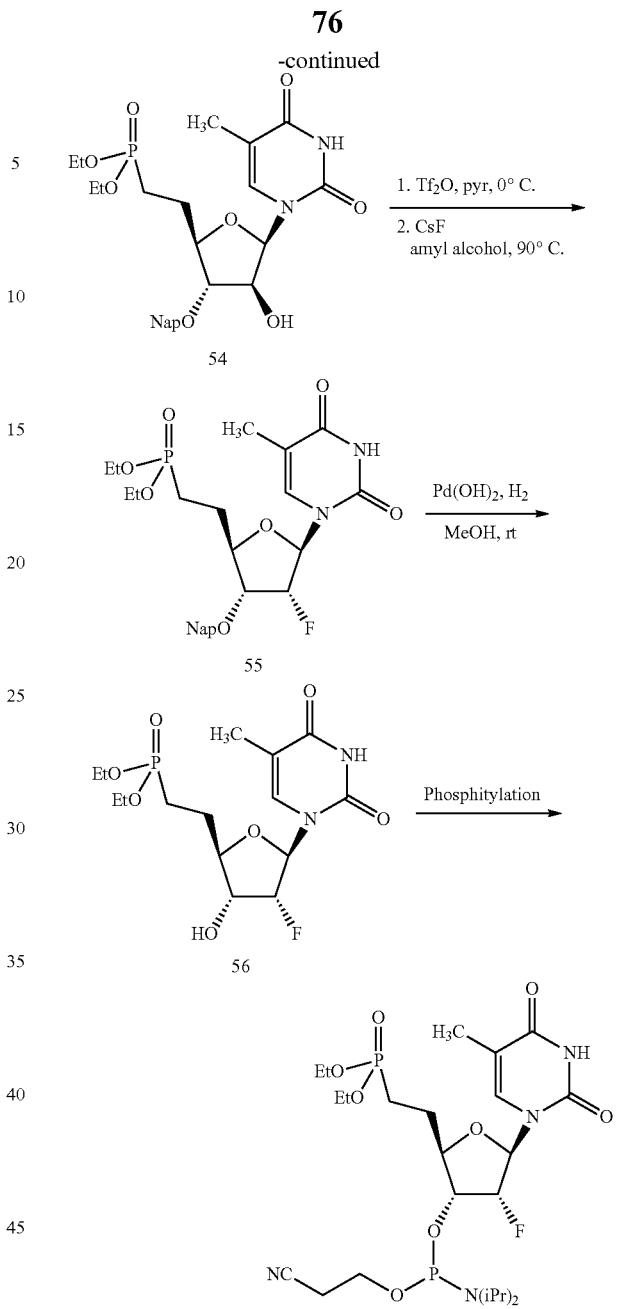
Compound 42 is prepared as per the procedures illustrated in Example 21.
Example 26
Preparation of Compound 58
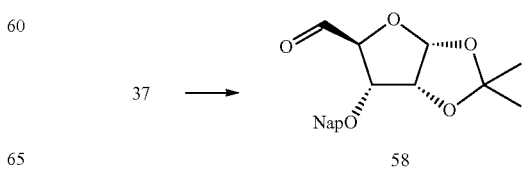

Compound 37 was prepared as per the procedures illustrated in Example 20. A solution of NaIO₄ (107.0 g) in water (3 L) was added over 40 minutes to a stirred (mechanical stirrer) solution of Compound 37 (crude from above) in dioxane (1.5 L). After 60 minutes the reaction mixture was poured into EtOAc (1.5 L) and the organic layer was separated, washed with water (1 L) and brine (1 L) then dried (Na₂SO₄) and concentrated to provide Compound 58 as a yellow oil, which was used without any further purification.

Example 27

Preparation of Compound 67

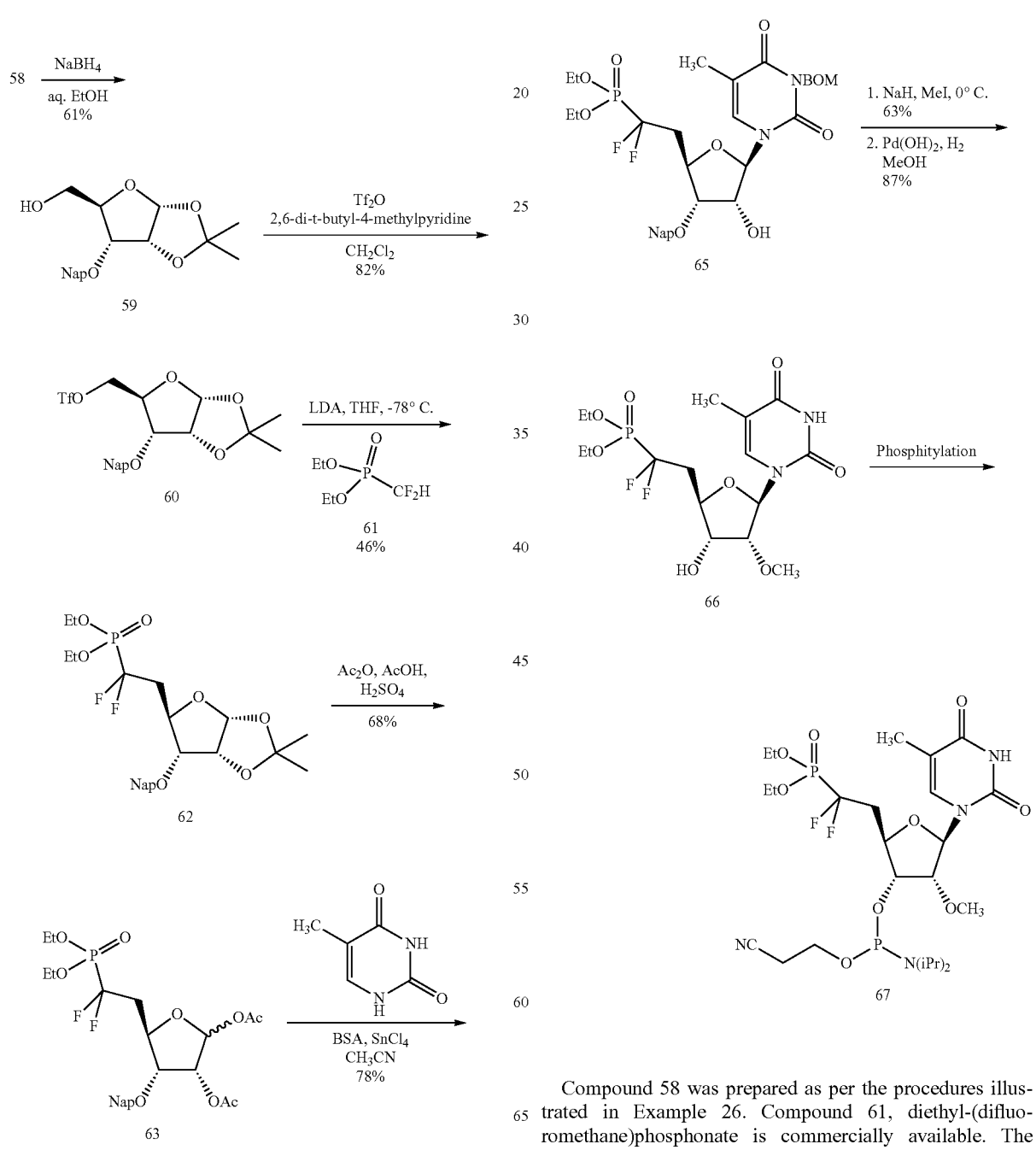

Compound 58 was prepared as per the procedures illustrated in Example 26. Compound 61, diethyl-(difluoromethane)phosphonate is commercially available. The preparation of Compound 67 was achieved as per the procedures illustrated in Example 27 and confirmed by spectral analysis, ¹HNMR and mass spectroscopy.

Example 28

Preparation of Compound 69

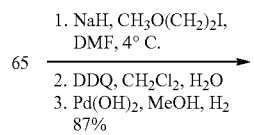

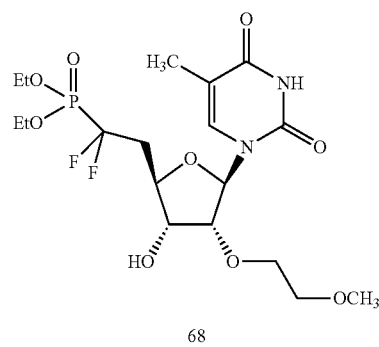

Compound 65 was prepared as per the procedures illustrated in Example 27. The preparation of Compound 69 was achieved as per illustrated in Example 28 and confirmed by spectral analysis, ¹HNMR and mass spectroscopy.

Example 29

Preparation of Compound 72

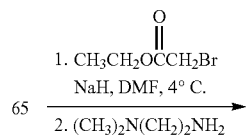

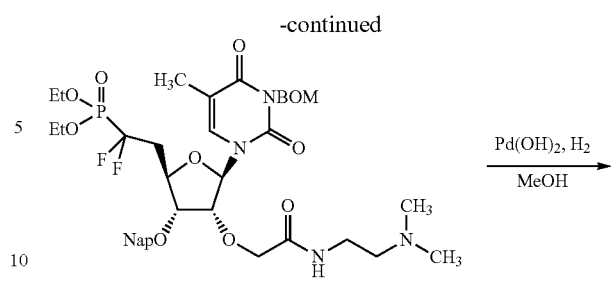

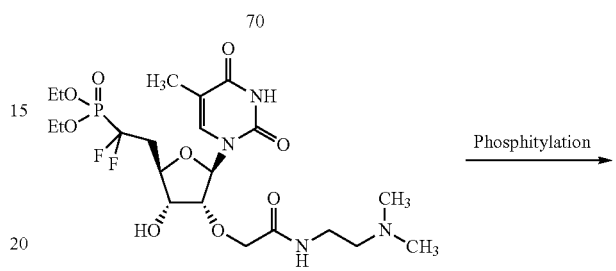

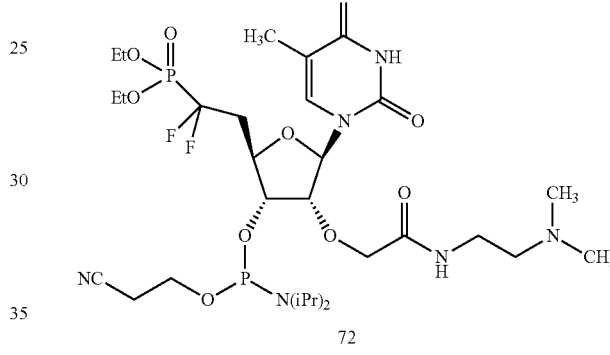

Compound 65 is prepared as per the procedures illustrated in Example 27.

Example 30

Preparation of Compound 75

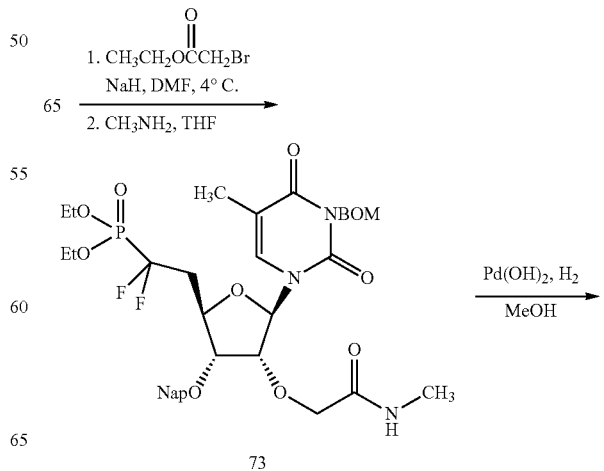

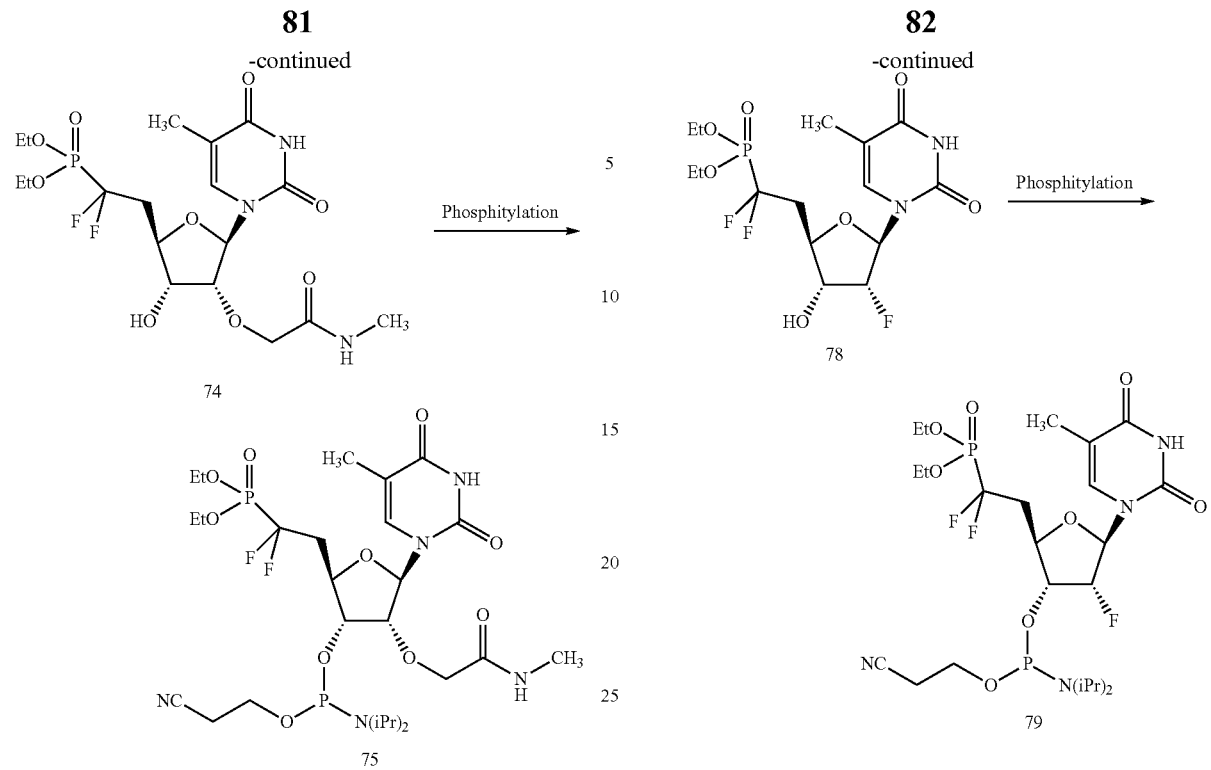
Compound 65 is prepared as per the procedures illustrated in Example 27.
Compound 64 is prepared as per the procedures illustrated in Example 27.
Example 31
Preparation of Compound 79
Example 32
Preparation of Compound 86
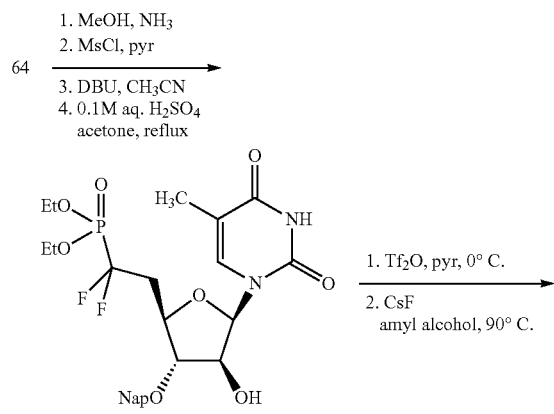
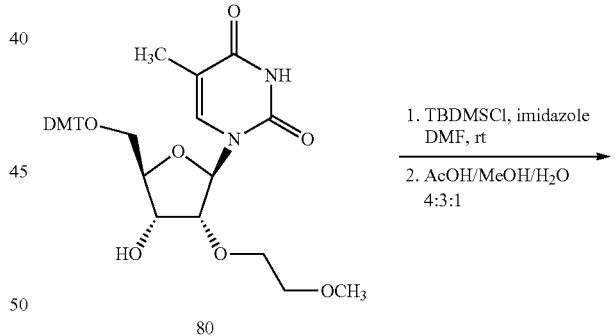
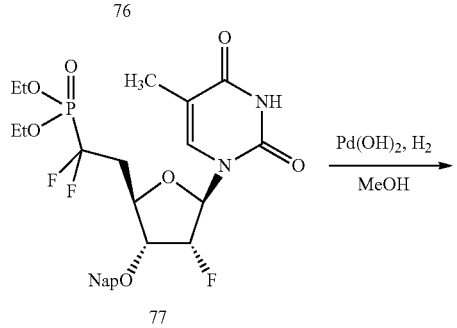
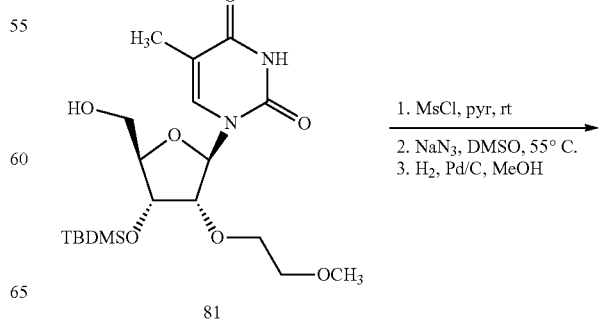

Example 33

Preparation of Compound 89

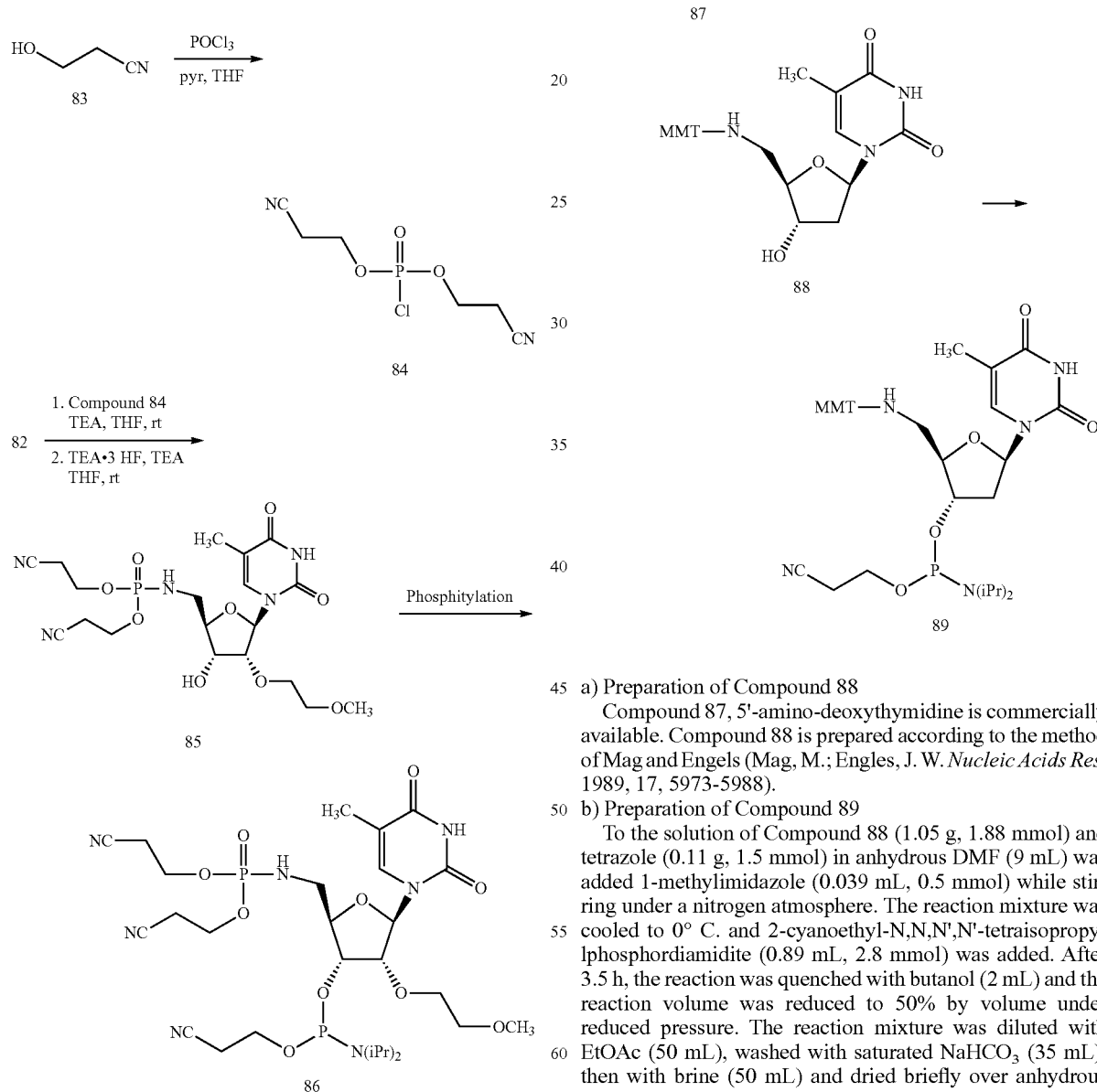

a) Preparation of Compound 88

Compound 87, 5'-amino-deoxythymidine is commercially available. Compound 88 is prepared according to the method of Mag and Engels (Mag, M.; Engles, J. W. *Nucleic Acids Res.* 1989, 17, 5973-5988).

b) Preparation of Compound 89

To the solution of Compound 88 (1.05 g, 1.88 mmol) and tetrazole (0.11 g, 1.5 mmol) in anhydrous DMF (9 mL) was added 1-methylimidazole (0.039 mL, 0.5 mmol) while stirring under a nitrogen atmosphere. The reaction mixture was cooled to 0° C. and 2-cyanoethyl-N,N,N',N'-tetraisopropylphosphordiamidite (0.89 mL, 2.8 mmol) was added. After 3.5 h, the reaction was quenched with butanol (2 mL) and the reaction volume was reduced to 50% by volume under reduced pressure. The reaction mixture was diluted with EtOAc (50 mL), washed with saturated $NaHCO_3$ (35 mL), then with brine (50 mL) and dried briefly over anhydrous $Na_2SO_4$. The organic phase was filtered and concentrated under reduced pressure. The resulting residue was dissolved in diethyl ether:$CH_2Cl_2$ (1:1, 2.25 mL) and was added dropwise into an ice cold pentane (300 mL) solution. The resulting solid was filtered to afford Compound 89 (1.24 g, 86.7%). $^{31}P$ NMR (121 MHz, $CD_3CN$): δ 148.31 and 148.08.

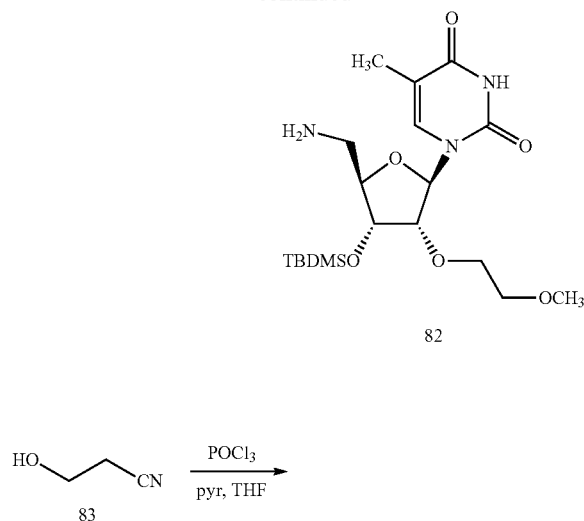

Compound 80 is prepared according to the procedures illustrated in published U.S. Pat. No. 5,969,116.

85
Example 34
Preparation of Compound 92
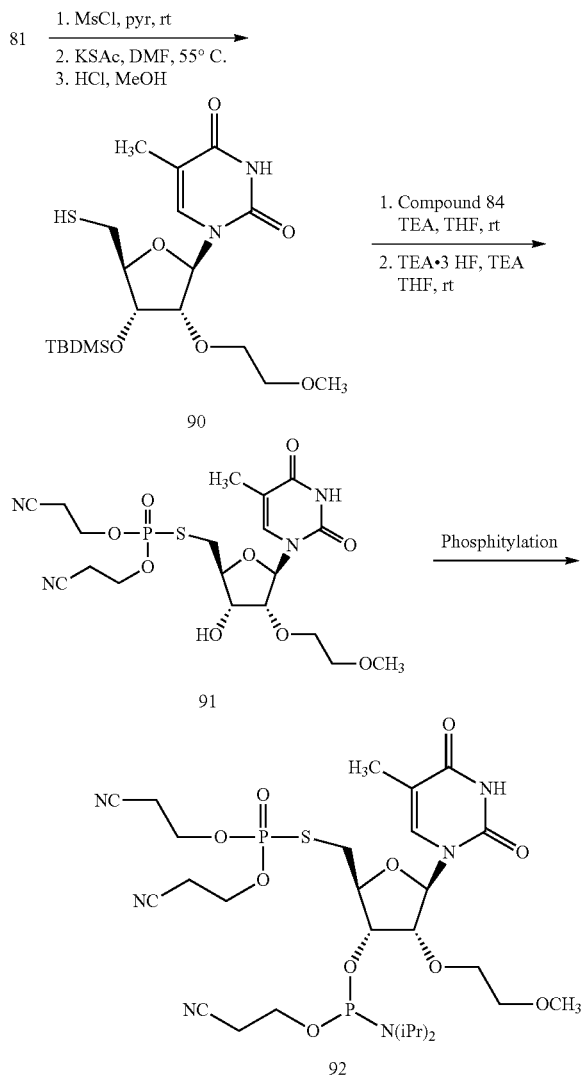
Compounds 81 and 84 are prepared as per the procedures illustrated in Example 32.
Example 35
Preparation of Compound 93
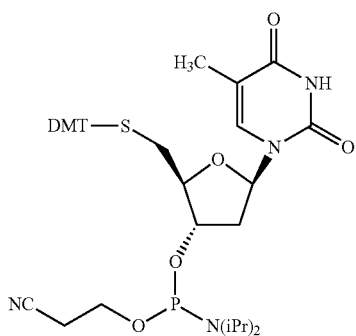
86
Compound 93 is prepared according to the method of Jahn-Hofmann and Engels (Jahn-Hofmann, K.; Engles, J. W. *Helvetica Chimica Acta* 2004, 87, 2812-2828).
Example 36
Preparation of Compound 102
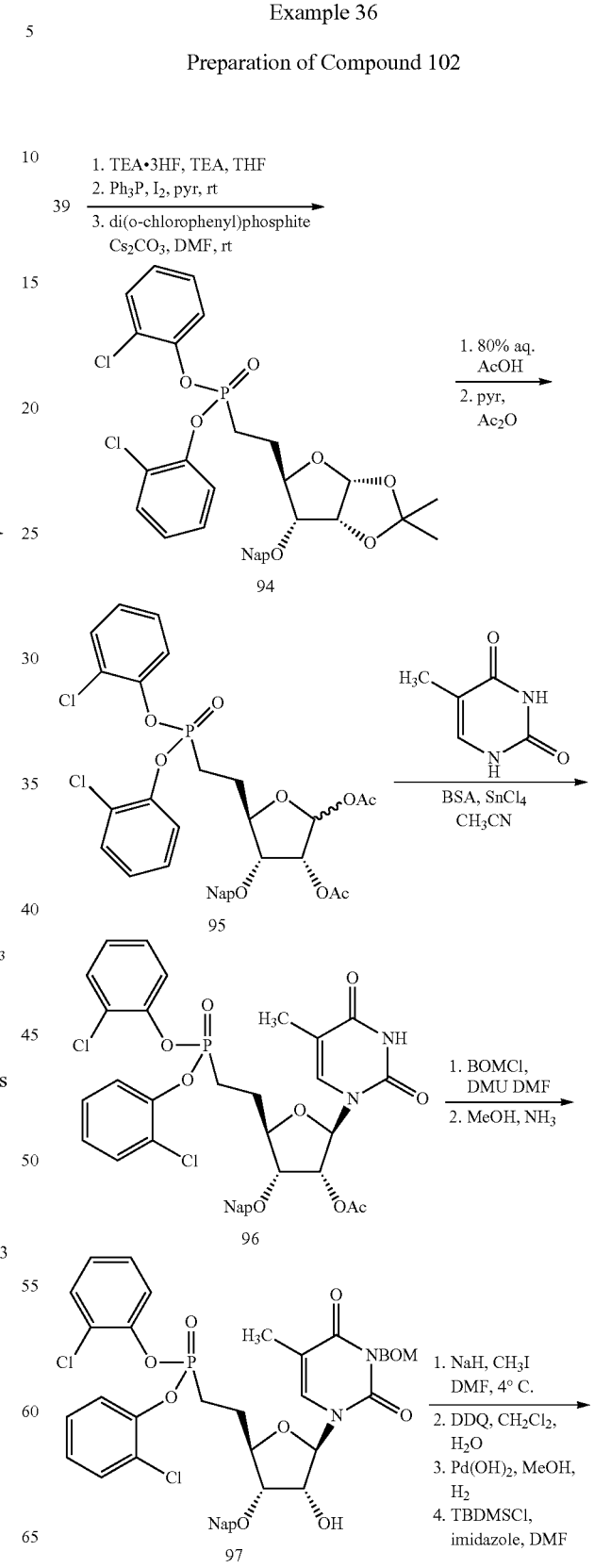

87
-continued
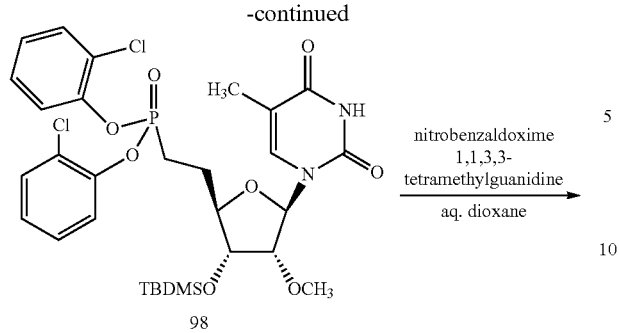
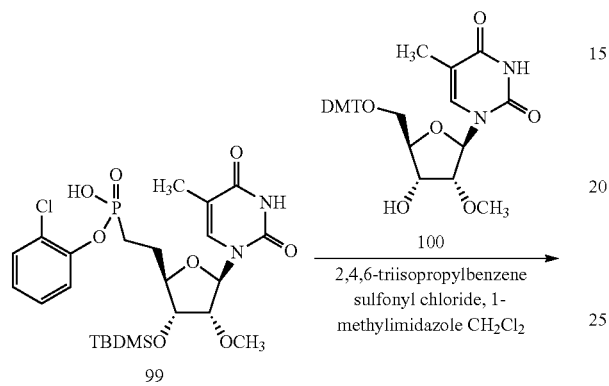
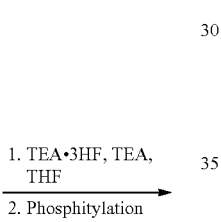
101
88
-continued
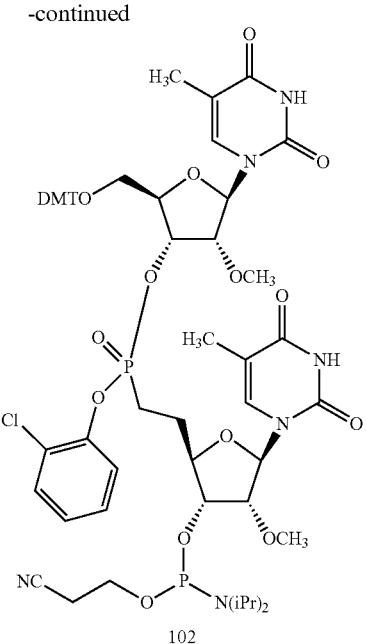
Compound 39 is prepared as per the procedures illustrated in Example 21. Compound 100 is prepared according to the method published by Inoue, H. et al. *Nucleic Acids Research* 1987, 15, 6131-6148.
Example 37
Preparation of Compound 106
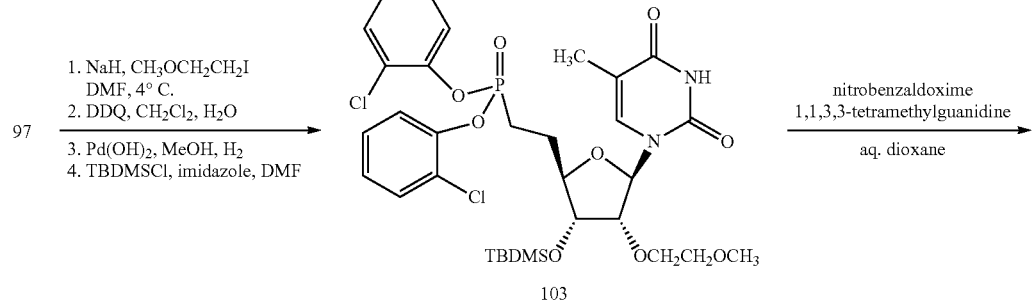

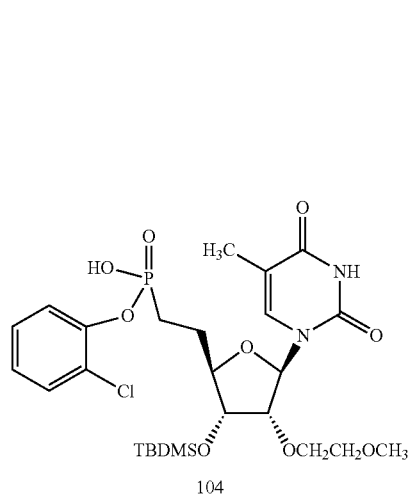
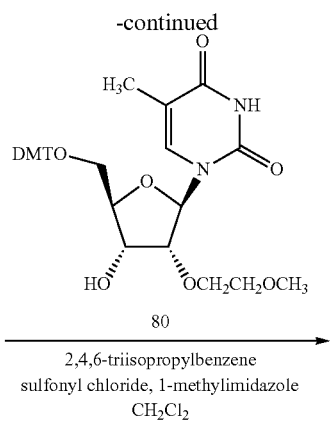
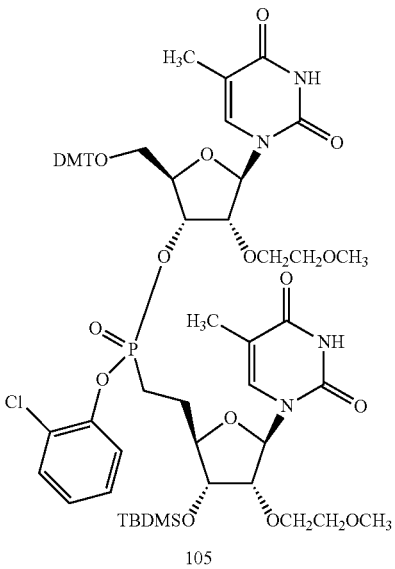
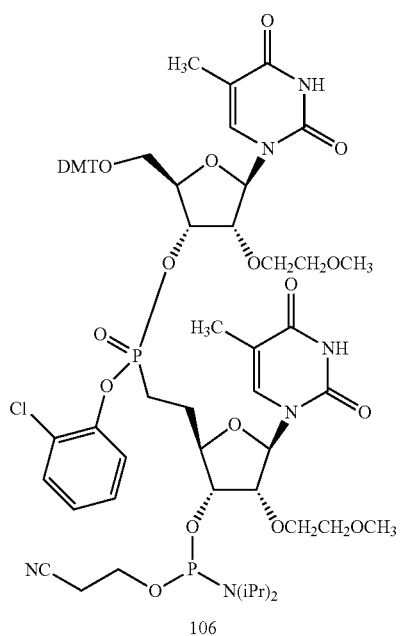
Compound 97 is prepared as per the procedures illustrated in Example 36. Compound 80 is prepared according to the procedures published in U.S. Pat. No. 5,969,116.
Example 38
Preparation of Compound 109
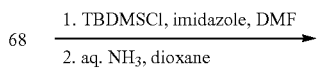

91
92
-continued
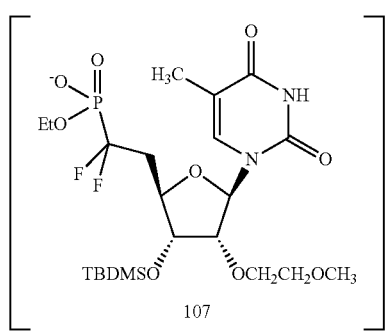
107
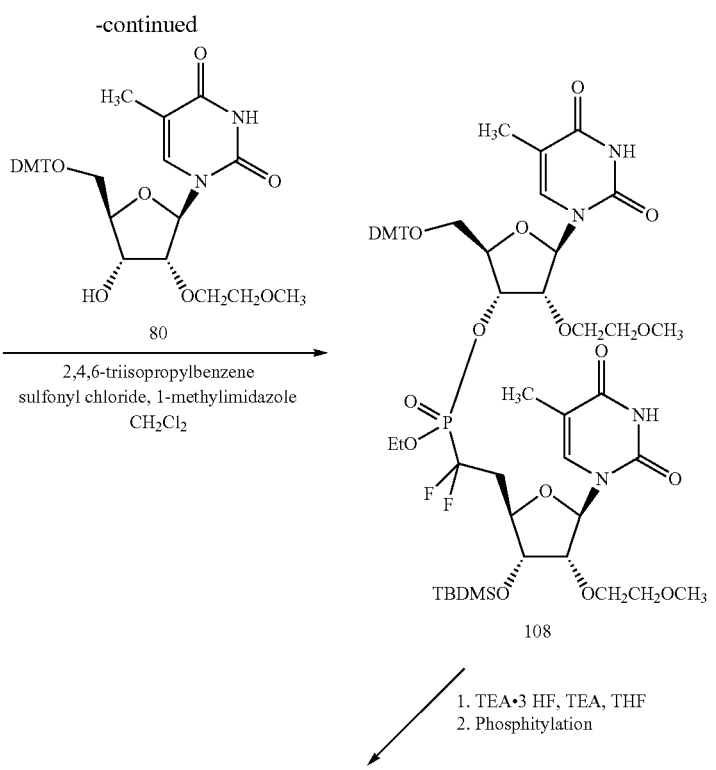
80
2,4,6-triisopropylbenzene sulfonyl chloride, 1-methylimidazole
CH$_2$Cl$_2$
108
1. TEA·3 HF, TEA, THF
2. Phosphitylation
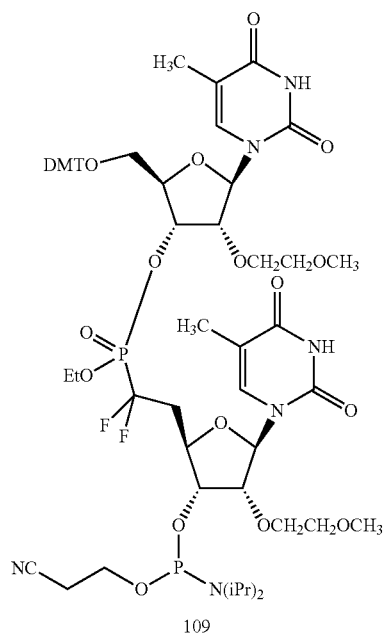
109

Compound 68 is prepared as per the procedures illustrated in Example 28. Compound 80 is prepared according to the procedures published in U.S. Pat. No. 5,969,116.
Example 39
Preparation of Compound 112
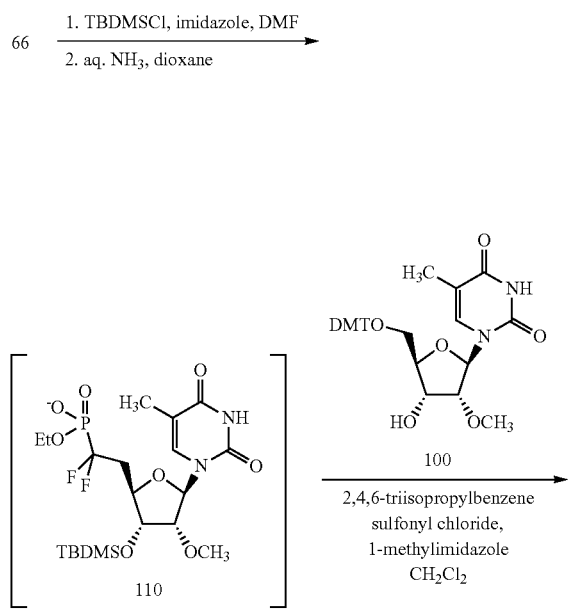
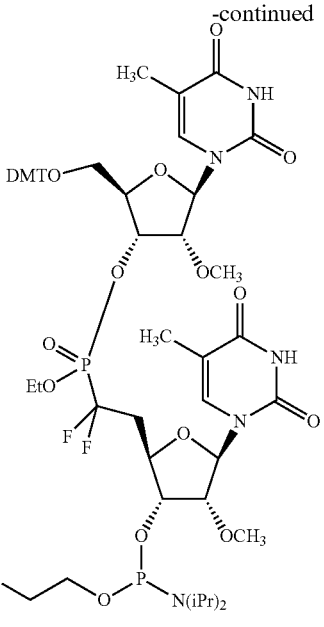
Compound 66 is prepared per illustrated in Example 27. Compound 100 is prepared according to the method published by Inoue, H. et al. *Nucleic Acids Research* 1987, 15, 6131-6148.
Example 40
Preparation of Compound 116
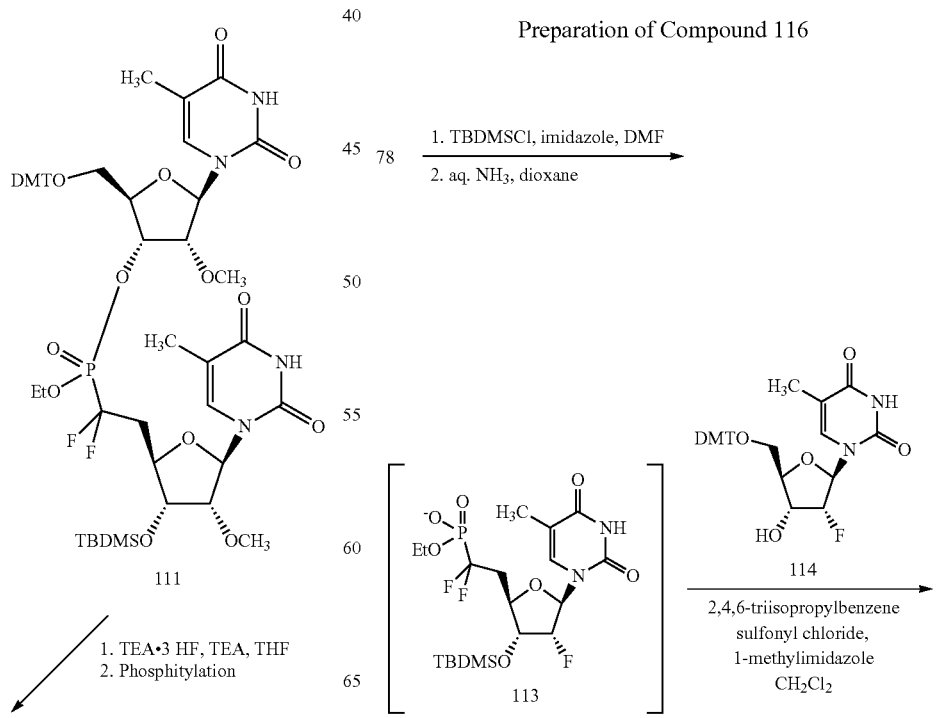

95
-continued
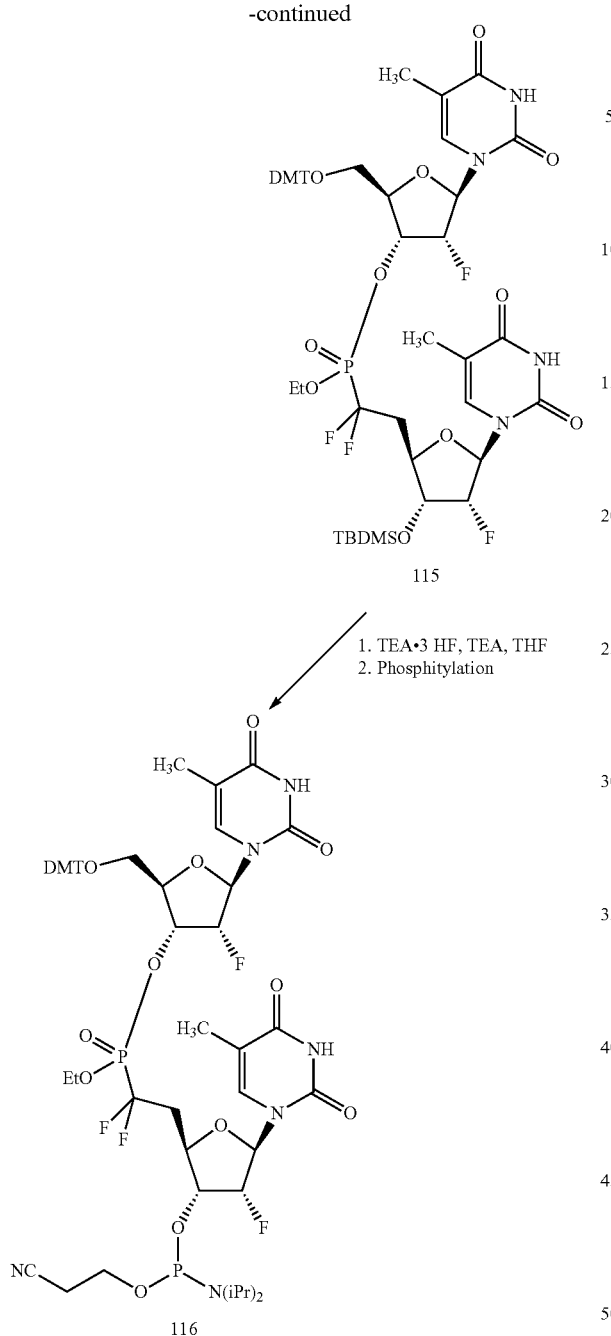
Compound 78 is prepared as per the procedures illustrated in Example 31. Compound 114 is prepared according to procedures published by Ikeda, H. et al. *Nucleic Acids Research* 1998, 26, 2237-2244.
Example 41
Preparation of Compounds 119, 120 and 121
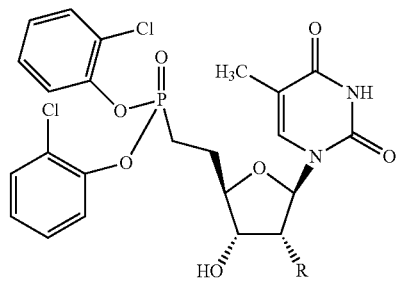
96
-continued
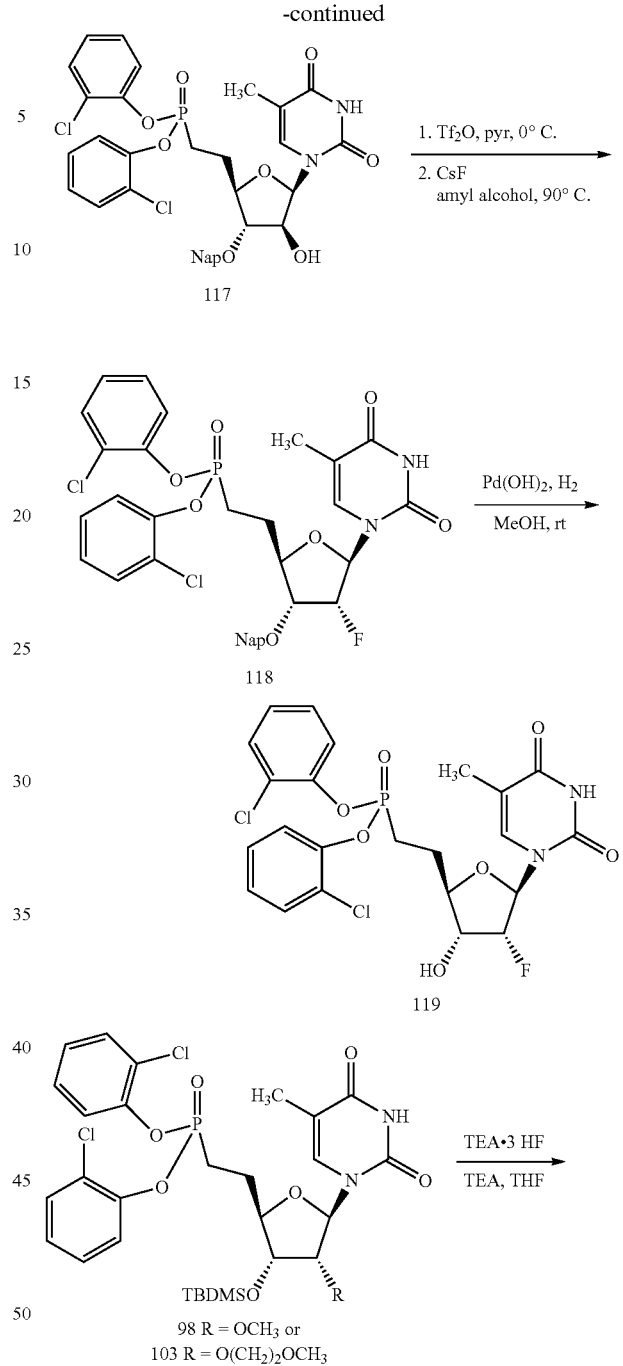

Compounds 96 and 98 are prepared as per the procedures illustrated in Example 36. Compound 103 is prepared as per the procedures illustrated in Example 37.
Example 42
Preparation of Compound 125
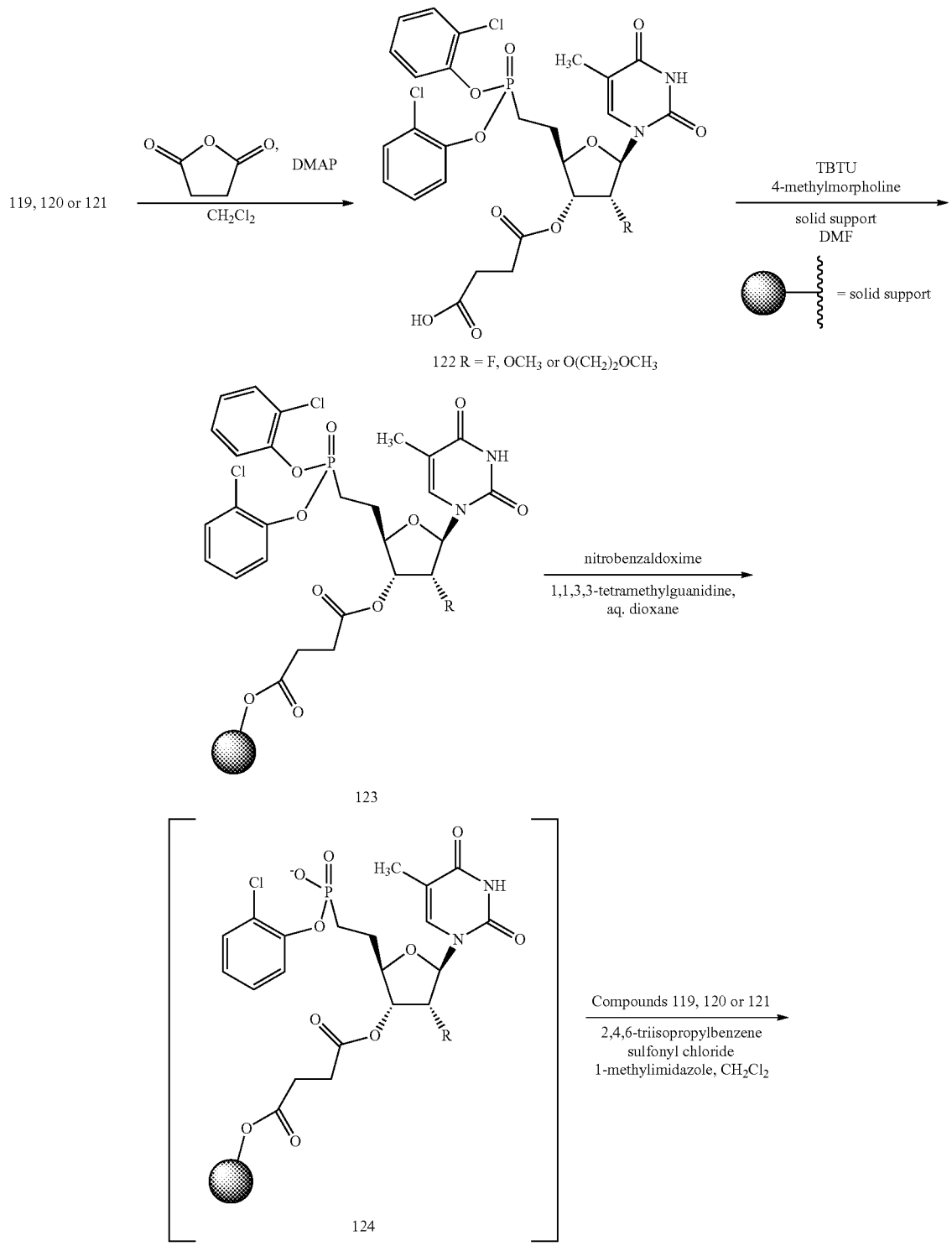

-continued
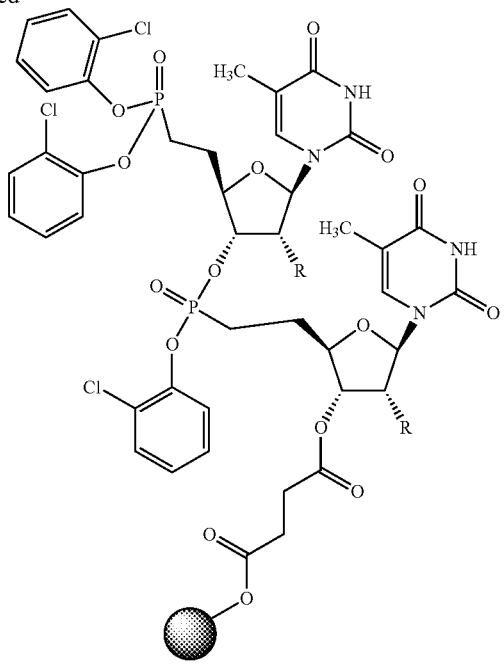
125
Compounds 119, 120 and 121 are prepared as per the procedures illustrated in Example 41.
Example 43
Preparation of Compounds 126 and 127
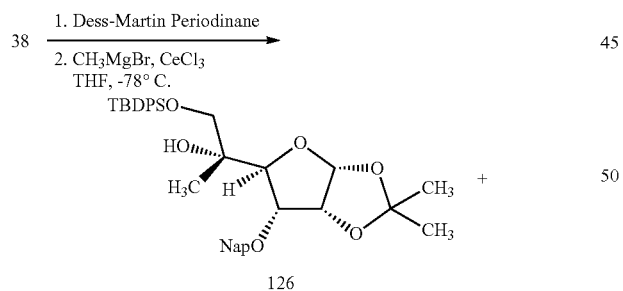
-continued
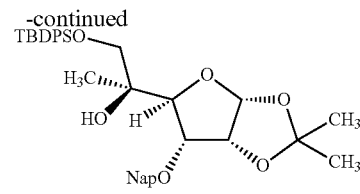
Compound 38 is prepared as per the procedures illustrated in Example 21.
Example 44
Preparation of Compounds 134 and 136
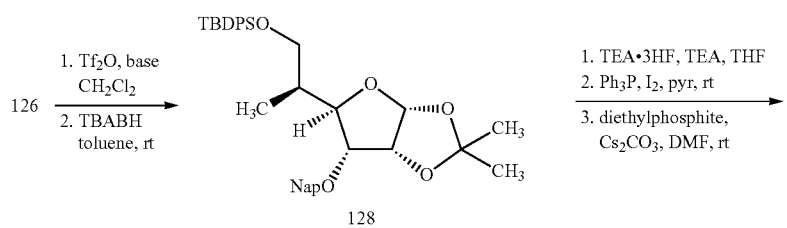

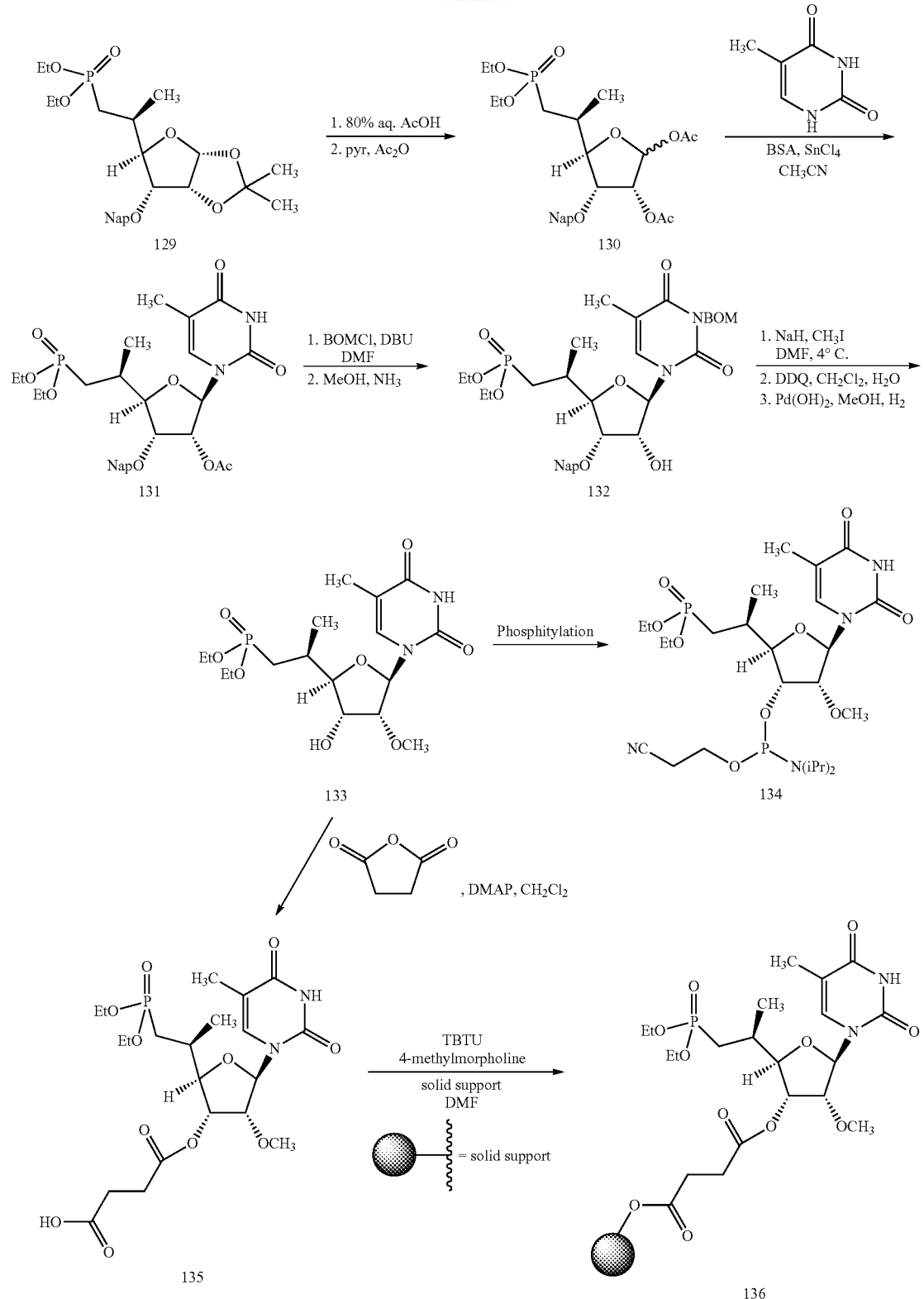
Compound 126 is prepared as per the procedures illustrated in Example 43.

Example 45
Preparation of Compounds 143 and 145
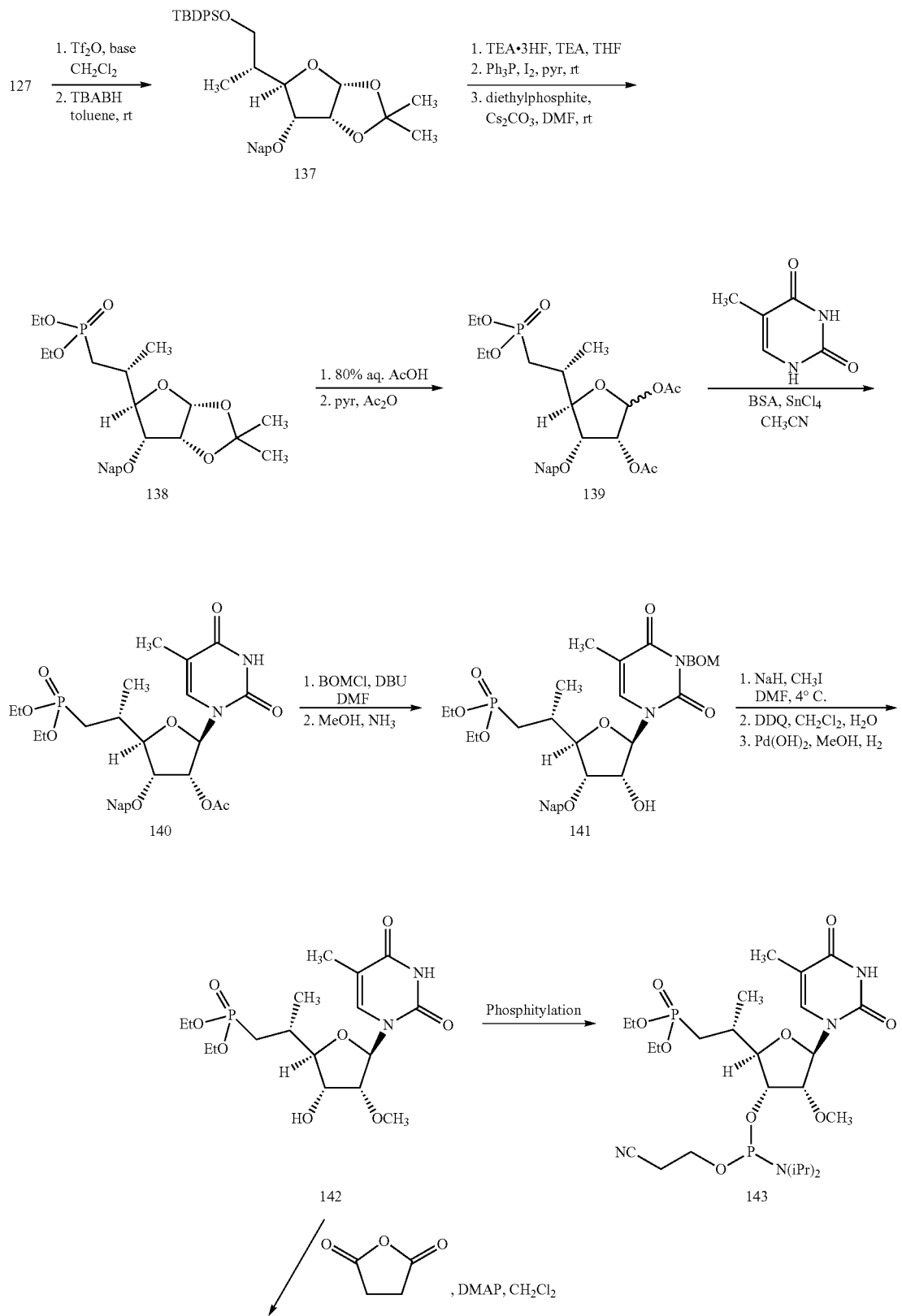

-continued
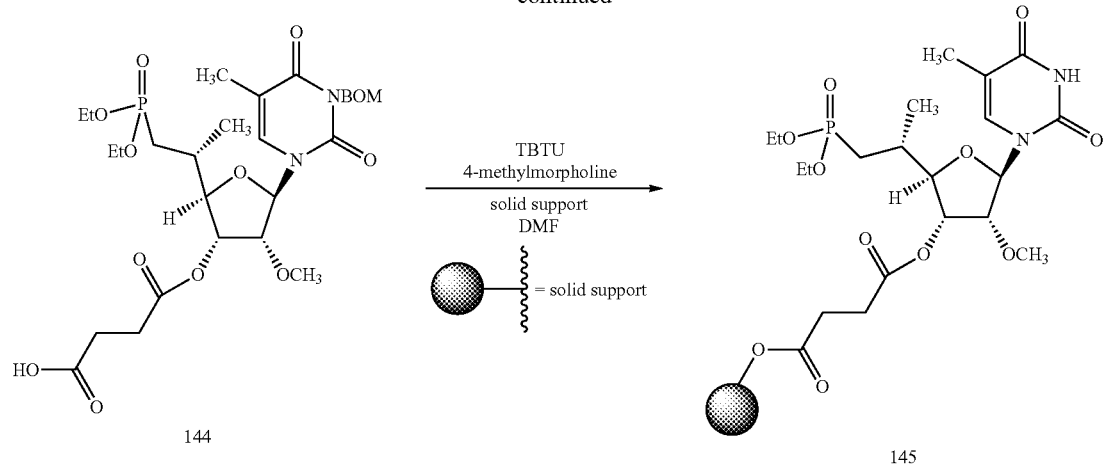
Compound 127 is prepared as per the procedures illustrated in Example 43.
Example 46
Preparation of Compounds 147 and 149
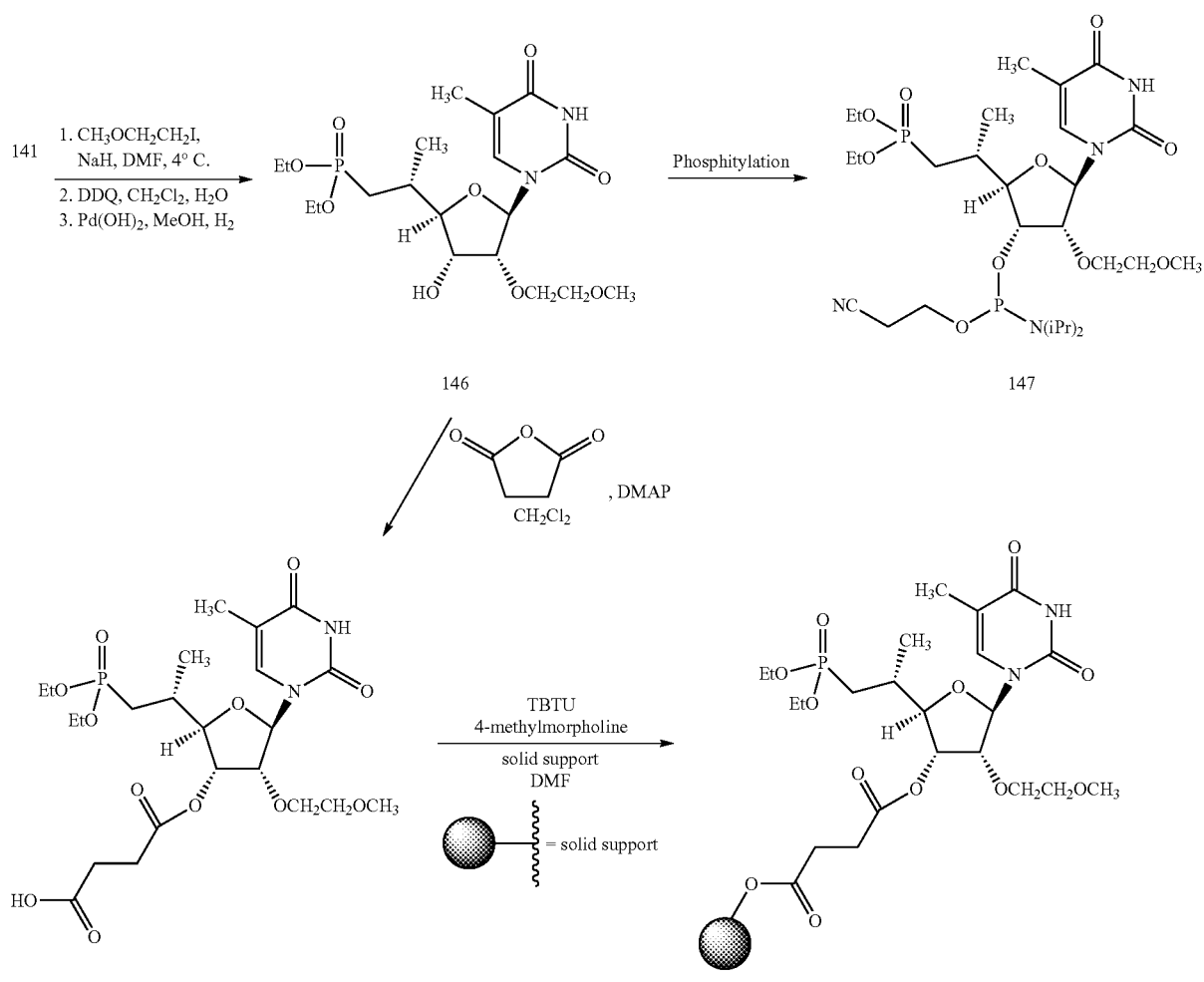
Compound 141 is prepared as per the procedures illustrated in Example 45.

Example 47
Preparation of Compounds 151 and 153
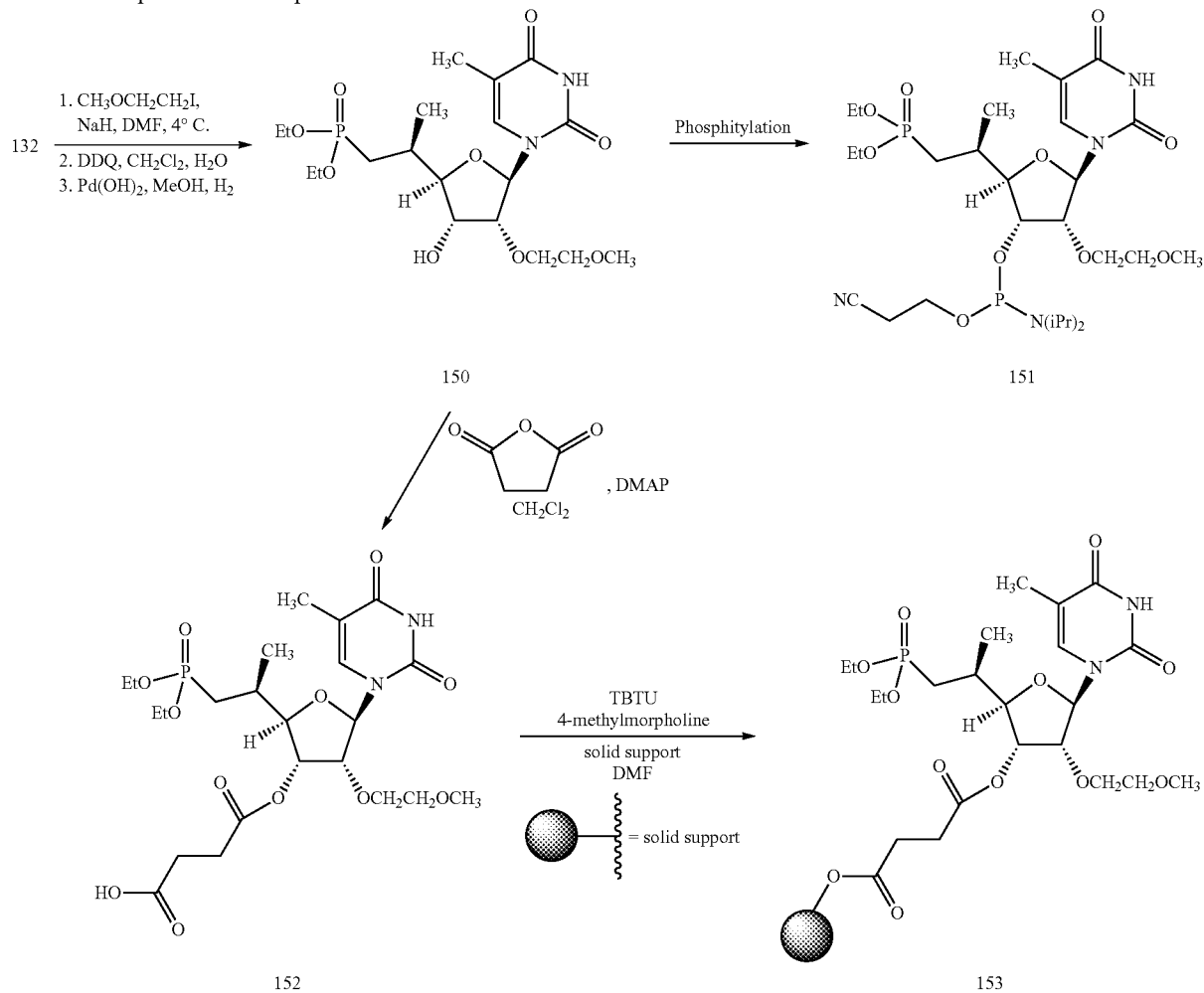
Compound 132 is prepared as per the procedures illustrated in Example 44.
Example 48
Preparation of Compounds 155 and 157
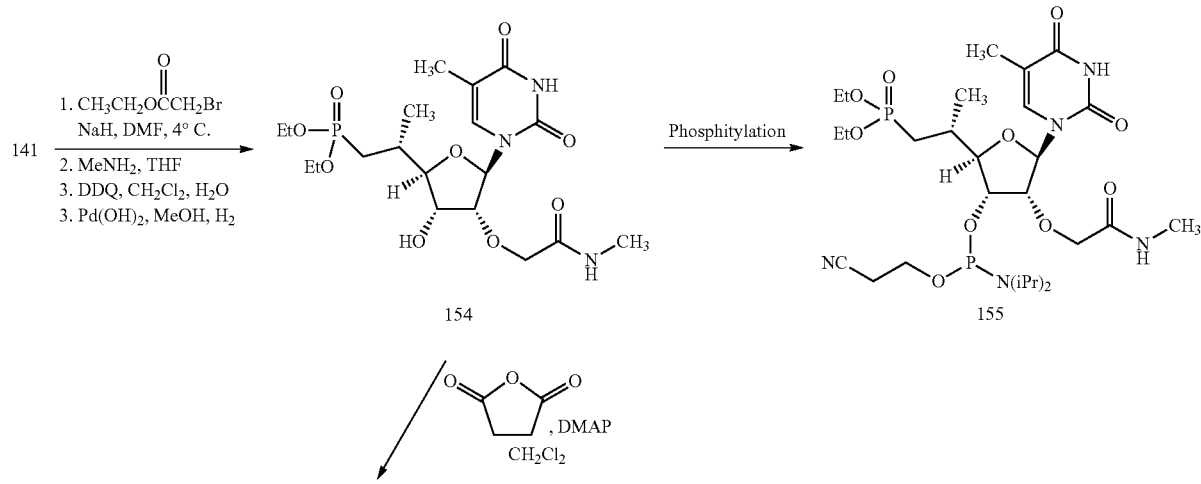

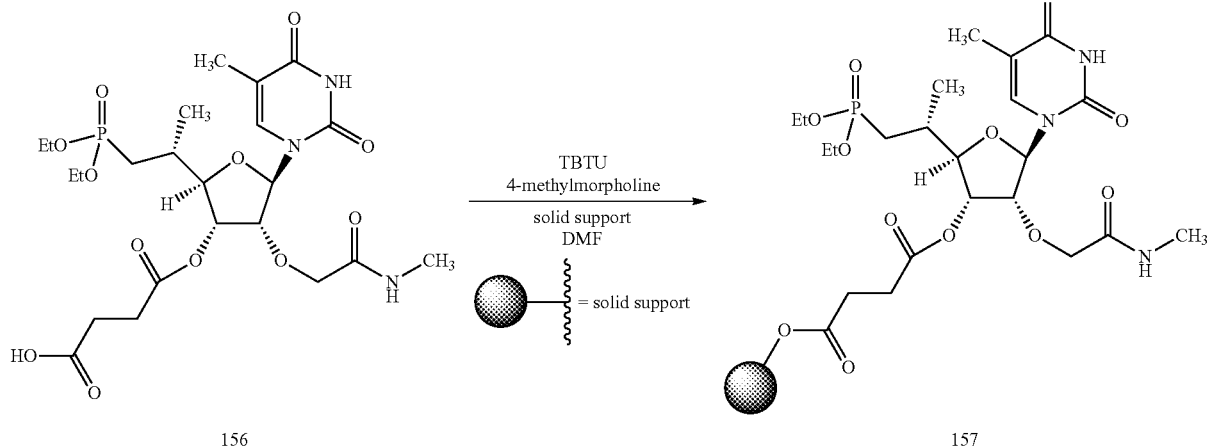
Compound 141 is prepared as per the procedures illustrated in Example 45.
Example 49
Preparation of Compounds 159 and 161
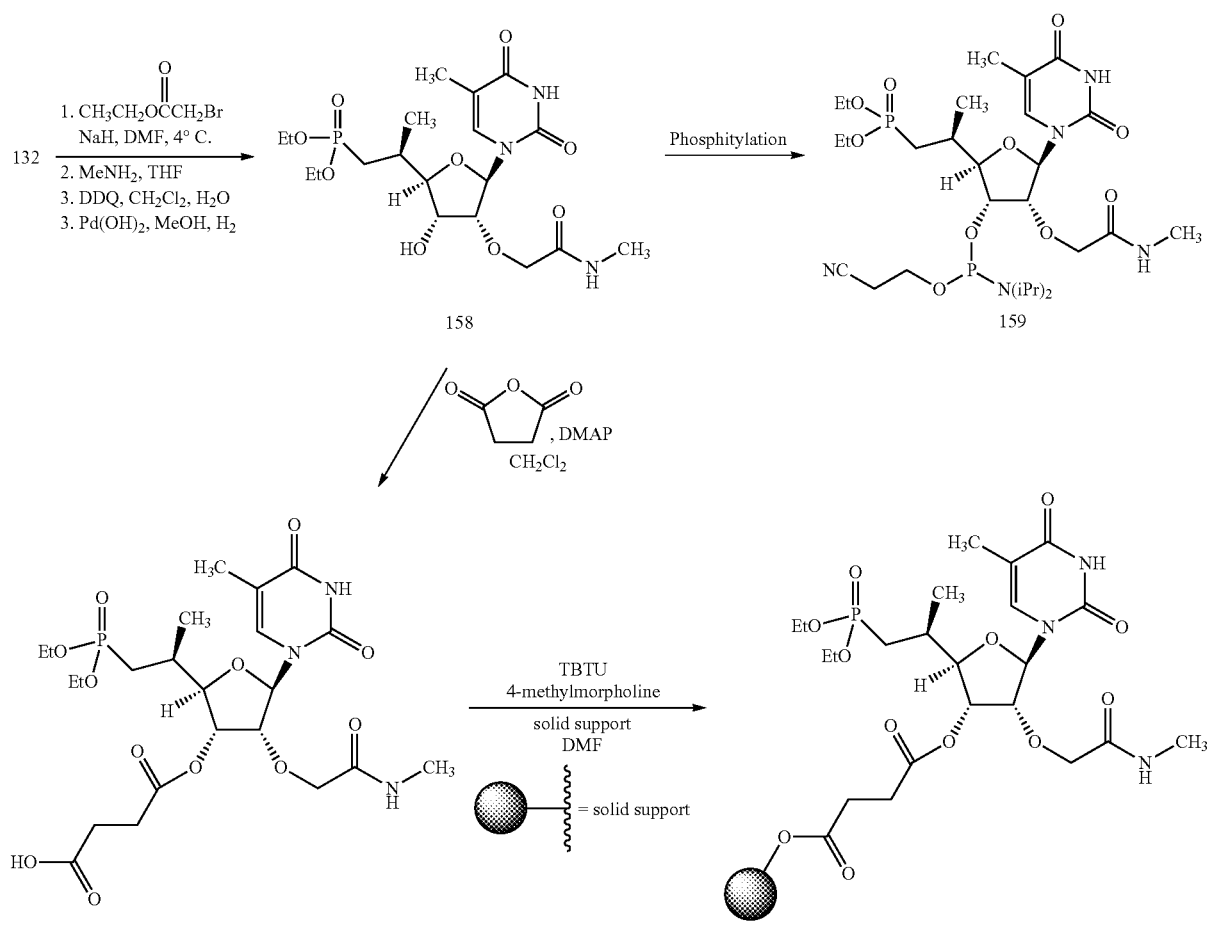
Compound 132 is prepared as per the procedures illustrated in Example 44.

Example 50
Preparation of Compounds 163 and 165
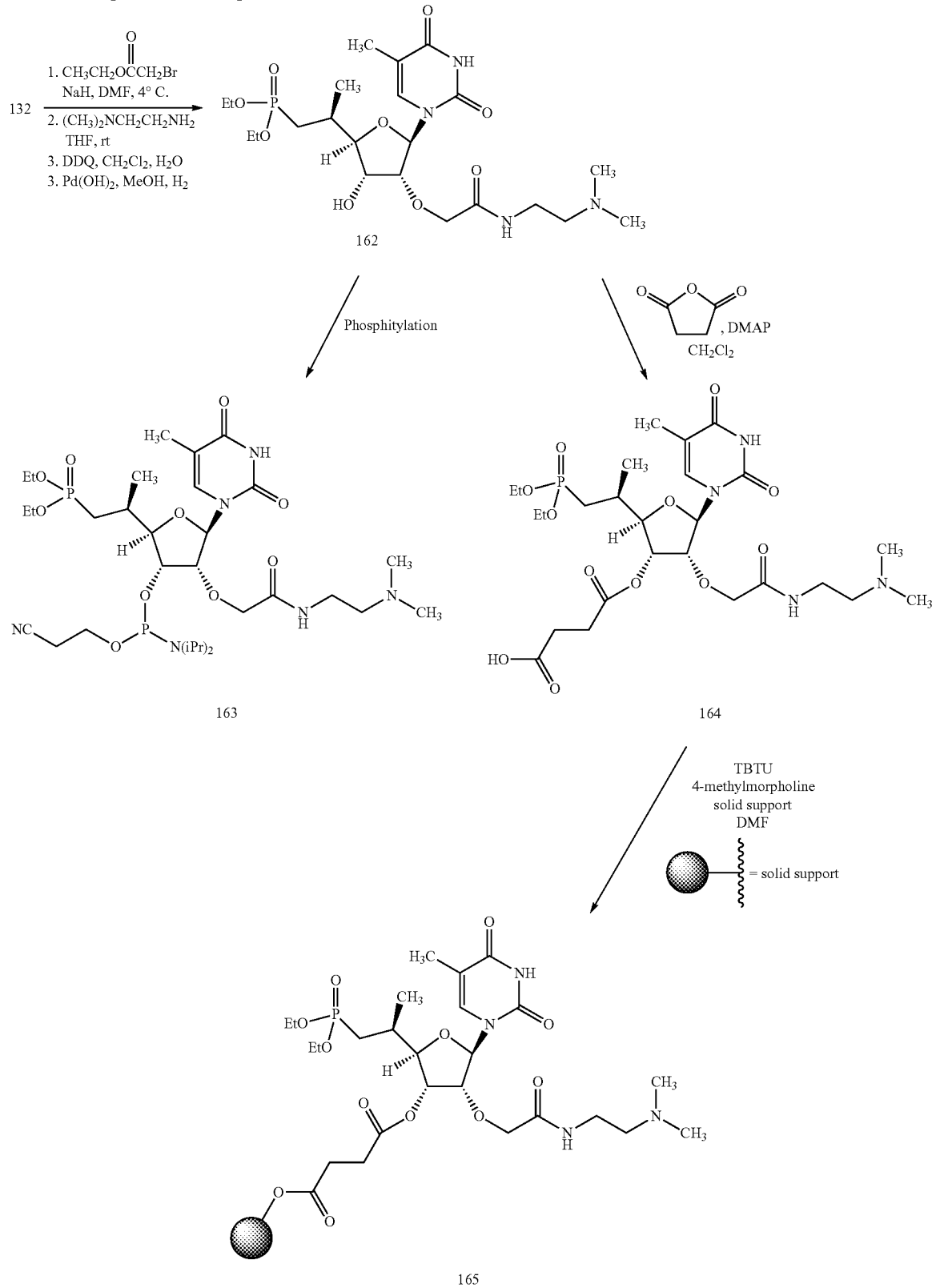
Compound 132 is prepared as per the procedures illustrated in Example 44.

Example 51
Preparation of Compounds 167 and 169
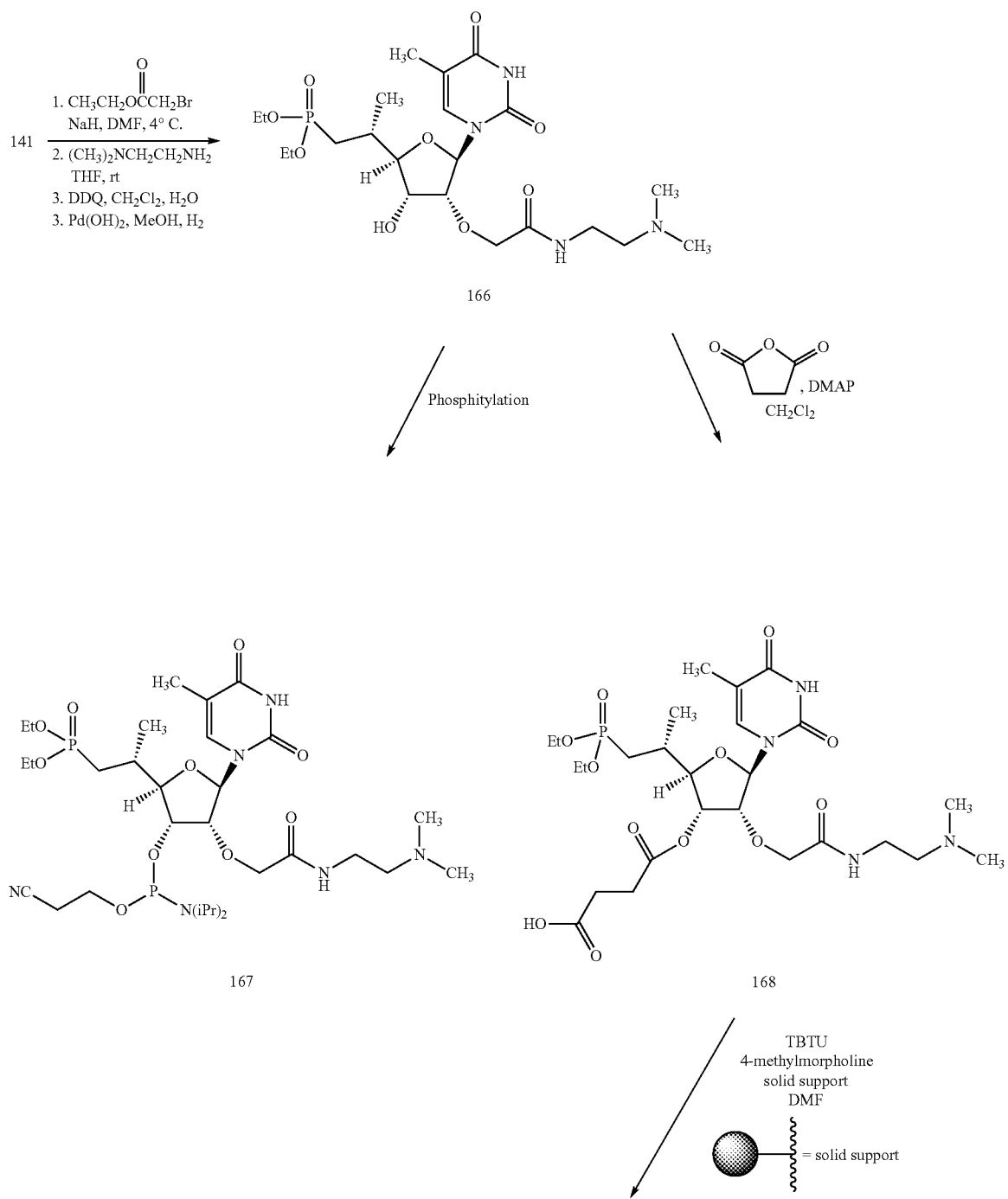

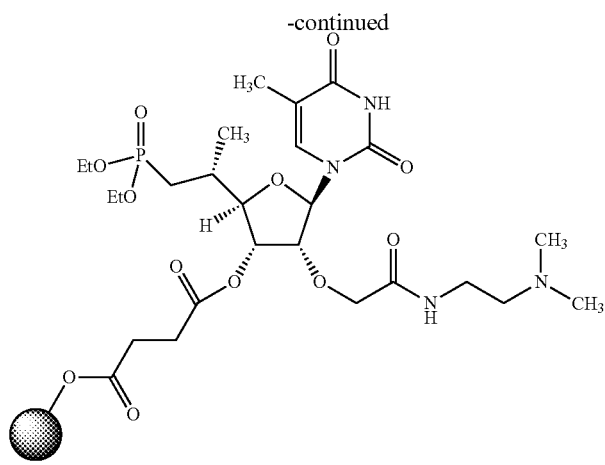
169
Compound 141 is prepared as per the procedures illustrated in Example 45.
Example 52
Preparation of Compounds 172 and 174
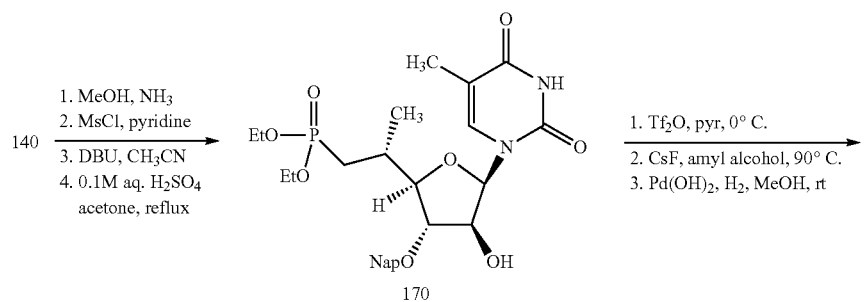
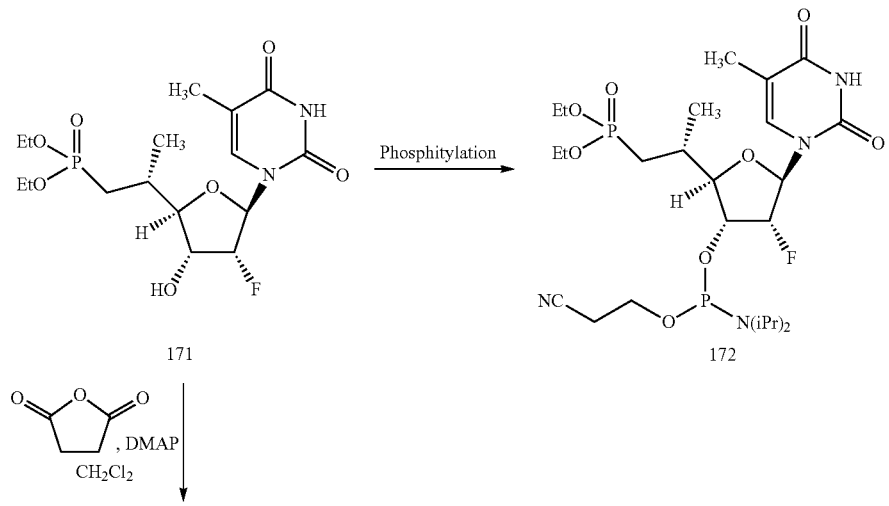

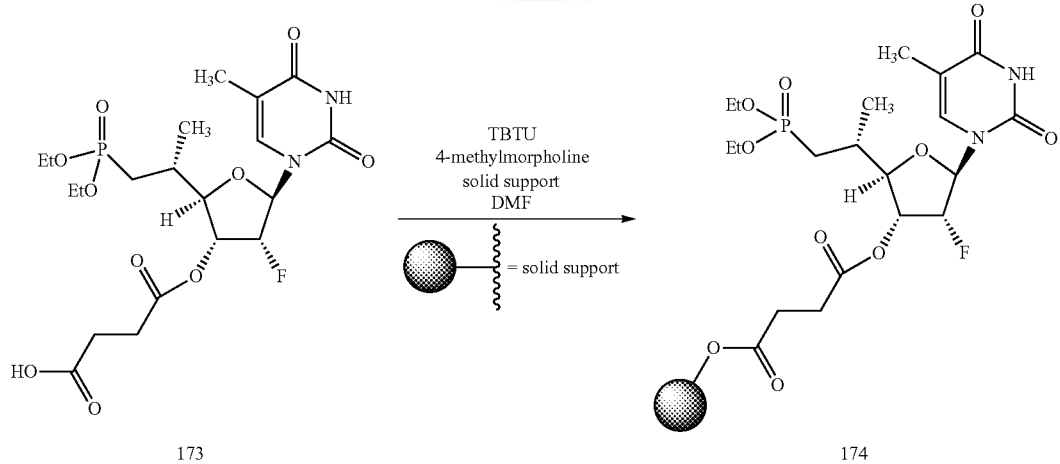
Compound 140 is prepared as per the procedures illustrated in Example 45.
Example 53
Preparation of Compounds 177 and 179
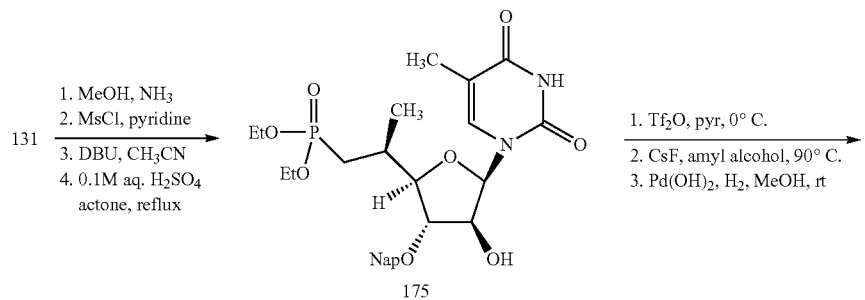
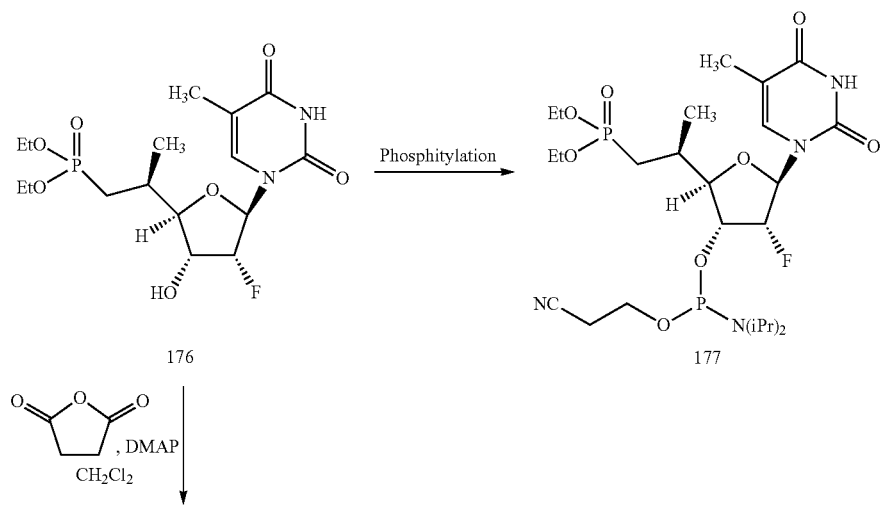

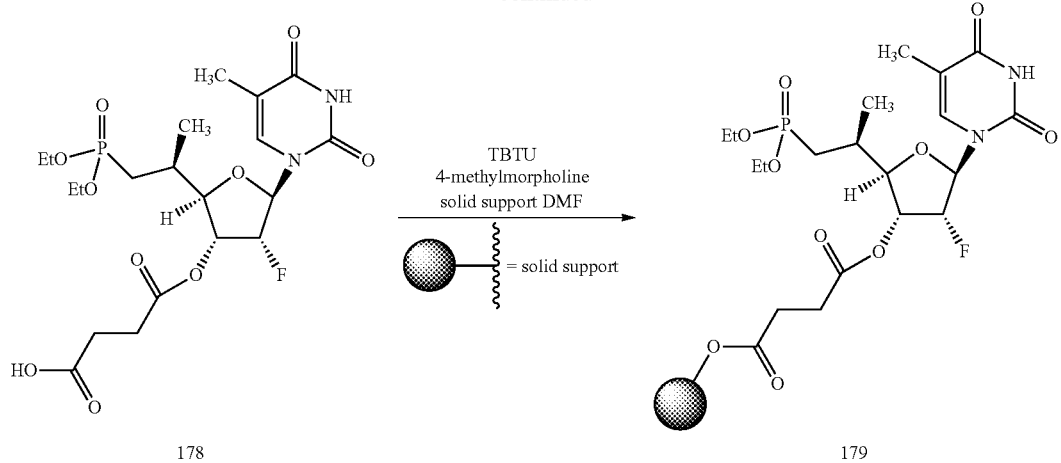
Compound 131 is prepared as per the procedures illustrated in Example 44.
Example 54
General Procedure for the Preparation of Compounds of Formula IIa and IIb
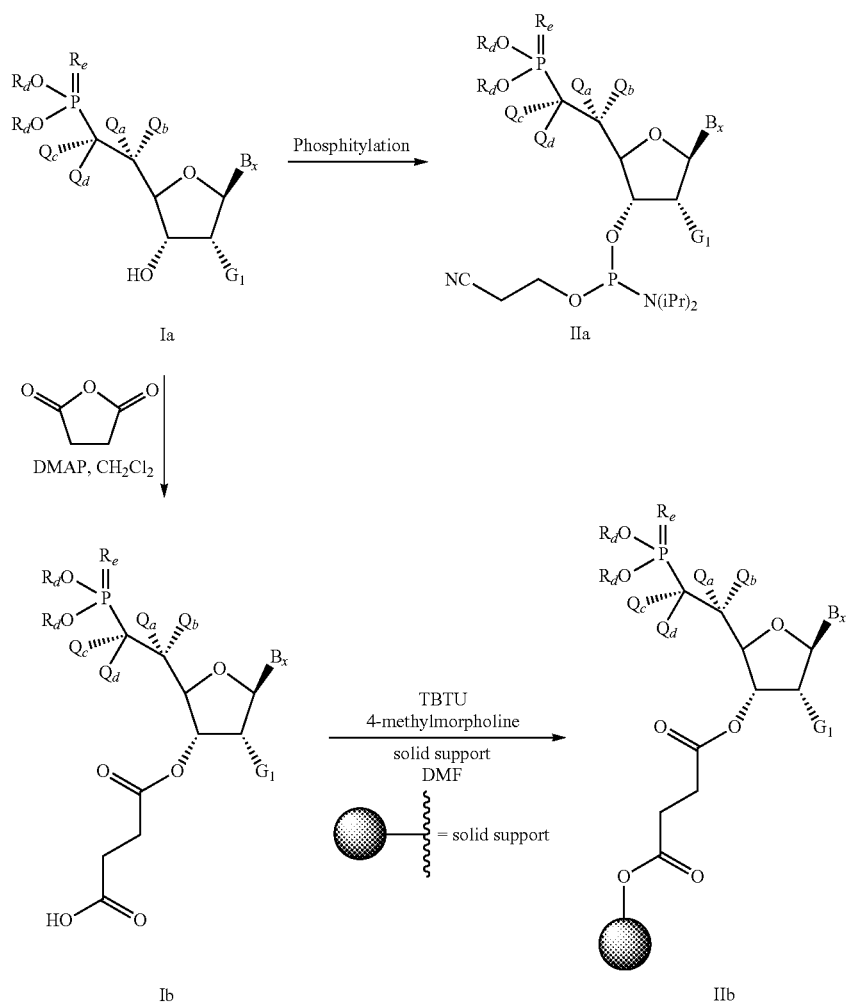

$B_x$ is a heterocyclic base moiety;

$Q_a$, $Q_b$, $Q_c$ and $Q_d$ are each independently H or a substituent group;

each $R_d$ is, independently, H, $C_1$-$C_6$ alkyl, substituted $C_1$-$C_6$ alkyl, aryl, substituted aryl or an internucleoside linkage to an oligomeric compound;

$R_e$ is O or S; and $G_1$ is a sugar substituent group.

The preparation of compounds of Formula Ia, Ib, IIa and IIb are illustrated in Examples 21-25, 27-35 and 44-53.

Example 55

General Procedure for the Preparation of Compounds of Formula IIIa

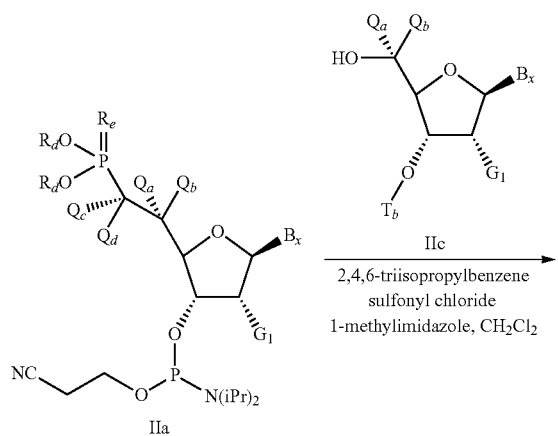

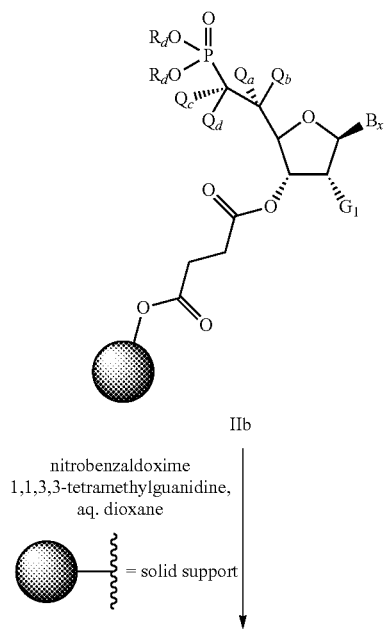

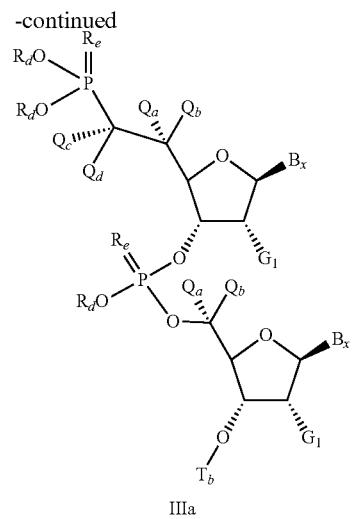

IIIa $B_x$ is a heterocyclic base moiety;

$Q_a$, $Q_b$, $Q_c$ and $Q_d$ are each independently H or a substituent group;

each $R_d$ is, independently, H, $C_1$-$C_6$ alkyl, substituted $C_1$-$C_6$ alkyl, aryl, substituted aryl or a linkage to an oligomeric compound;

$T_b$ is a protecting group, a 3'-terminal group or a linkage to an oligomeric compound $R_e$ is O or S; and $G_1$ is a sugar substituent group.

The preparation of compounds of Formula IIa, IIc, and IIIa are illustrated in Examples 13, 15-19, 21-25 and 27-53.

Example 56

General Procedure for the Preparation of Compounds of Formula IIIb and IIIc

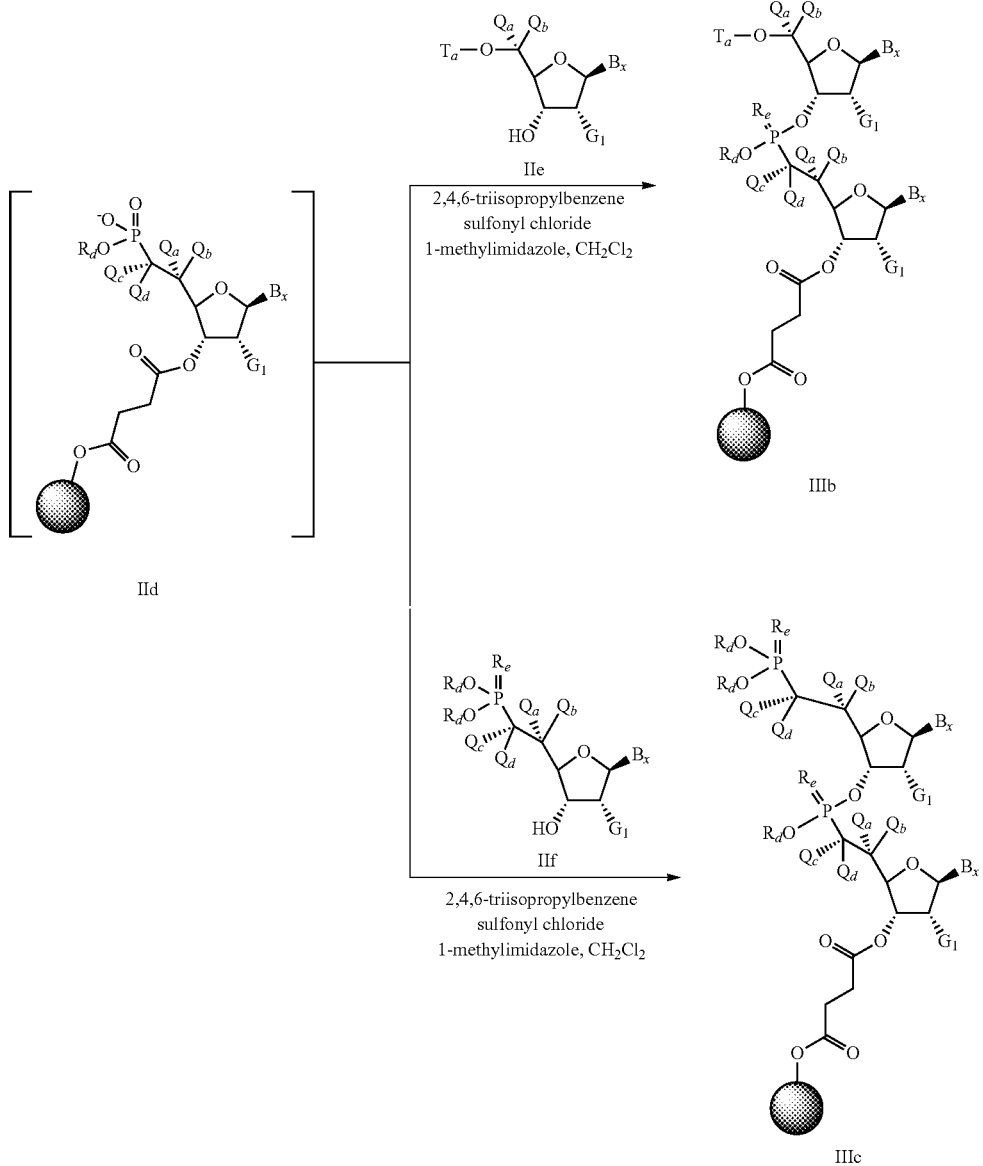

$B_x$ is a heterocyclic base moiety;
$Q_a$, $Q_b$, $Q_c$ and $Q_d$ are each independently H or a substituent group;
each $R_d$ is, independently, H, $C_1$-$C_6$ alkyl, substituted $C_1$-$C_6$ alkyl, aryl, substituted aryl or a linkage to an oligomeric compound;
$T_a$ is H, a protecting group or a 5'-terminal group;
$R_e$ is O or S; and
$G_1$ is a sugar substituent group.

The preparation of compounds of Formula IIb, IId, IIe, IIf, IIIb and IIIc are illustrated in Examples 13, 15-19, 21-25 and 27-53.

Example 57

Chemically Modified ssRNAs Targeting PTEN—In Vivo Study

The antisense activity of oligomeric compounds can be tested in vivo. Five- to six-week old Balb/c mice (Jackson Laboratory, Bar Harbor, Me.) are injected with modified ssRNA targeted to PTEN at doses of 80 mg/kg daily, 60 mg/kg daily, or 40 mg/kg twice daily for several days. The mice are sacrificed 72 hours following the last administration. Liver tissues are homogenized and mRNA levels are quantitated using real-time PCR using procedures illustrated herein for comparison to untreated control levels (% UTC). Other modifications and motifs as disclosed herein are also amenable to in vivo testing. Liver transaminase levels, alanine aminotranferease (ALT) and aspartate aminotransferase (AST), in serum are also measured relative to saline injected mice. At the end of the study, liver and spleen tissues are harvested from animals treated with the modified ssRNAs, the tissues are weighed to assess gross organ alterations.

| SEQ ID NO. | Composition (5' to 3') |
|---|---|
| 05/xxxxx | P-$U_xU_fG_mU_fC_mU_fC_mU_fG_mG_fU_mC_fC_mU_fU_mA_fC_mU_f$ $U_m\overline{A_e}A_e$ |

| SEQ ID NO. | Composition (5' to 3') |
|---|---|
| 05/xxxxx | P-U$_x$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 05/xxxxx | P-U$_{Sd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 05/xxxxx | P-U$_{Sd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 05/xxxxx | P-U$_{Sd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 05/xxxxx | P-U$_{Sd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 05/xxxxx | P-U$_{Sd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 05/xxxxx | P-U$_{Sd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 05/xxxxx | P-U$_{Sd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 05/xxxxx | P-U$_{Sd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 05/xxxxx | P-U$_{Rd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 05/xxxxx | P-U$_{Rd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 05/xxxxx | P-U$_{Rd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 05/xxxxx | P-U$_{Rd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 05/xxxxx | P-U$_{Rd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 05/xxxxx | P-U$_{Rd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 05/xxxxx | P-U$_{Rd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-T$_{Rd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-T$_{Rd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-T$_{Rd}$U$_f$G$_m$U$_f$C$_m$U$_f$C$_m$U$_f$G$_m$G$_f$U$_m$C$_f$C$_m$U$_f$U$_f$A$_f$C$_f$U$_f$U$_f$A$_e$A$_e$ |
| 06/xxxxx | P-T$_{Rd}$U$_f$G$_m$U$_f$C$_m$U$_f$C$_m$U$_f$G$_m$G$_f$U$_m$C$_f$C$_f$U$_f$U$_f$A$_f$C$_f$U$_f$U$_f$A$_e$A$_e$ |
| 06/xxxxx | P-T$_{Rd}$U$_f$G$_m$U$_f$C$_m$U$_f$C$_m$U$_f$G$_m$G$_f$U$_m$C$_f$C$_f$U$_f$U$_f$A$_f$C$_f$U$_f$U$_f$A$_e$A$_e$ |
| 06/xxxxx | P-T$_{Rd}$U$_f$G$_m$U$_f$C$_m$U$_f$C$_m$U$_f$G$_m$G$_f$U$_f$C$_f$C$_f$U$_f$U$_f$A$_f$C$_f$U$_f$U$_f$A$_e$A$_e$ |
| 06/xxxxx | P-T$_{Sd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-T$_{Sd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-T$_{Sd}$U$_f$G$_m$U$_f$C$_m$U$_f$C$_m$U$_f$G$_m$G$_f$U$_m$C$_f$C$_m$U$_f$U$_f$A$_f$C$_f$U$_f$U$_f$A$_e$A$_e$ |
| 06/xxxxx | P-T$_{Sd}$U$_f$G$_m$U$_f$C$_m$U$_f$C$_m$U$_f$G$_m$G$_f$U$_m$C$_f$C$_f$U$_f$U$_f$A$_f$C$_f$U$_f$U$_f$A$_e$A$_e$ |
| 06/xxxxx | P-T$_{Sd}$U$_f$G$_m$U$_f$C$_m$U$_f$C$_m$U$_f$G$_m$G$_f$U$_f$C$_f$C$_f$U$_f$U$_f$A$_f$C$_f$U$_f$U$_f$A$_e$A$_e$ |

Each nucleoside is connected to the following nucleoside by a phosphodiester internucleoside linkage except underlined nucleosides which are connected to the following nucleoside by a phosphorothioate internucleoside linkage (going 5' to 3'). A "P" at the 5'-end indicates a 5'-phosphate group. Nucleosides followed by a subscript x, f, m or e are sugar modified nucleosides. A subscript "f" indicates a 2'-fluoro modified nucleoside, a subscript "m" indicates 2'-O-methyl modified nucleoside, a subscript "e" indicates a 2'-O(CH$_2$)$_2$OCH$_3$ (MOE) modified nucleoside and a subscript Rd or Sd or x indicates one of the 2',5'-bis modified nucleosides listed below (Rd, Sd, Rb, Sb, Rc or Sc). In general, each modified nucleoside having an x after it will have the same sugar modification.

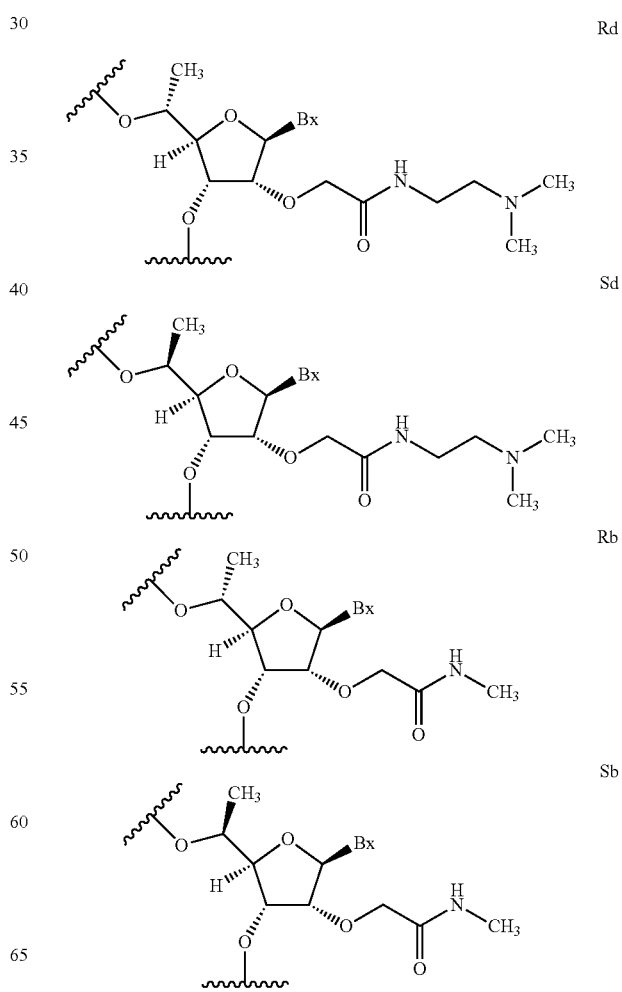

-continued

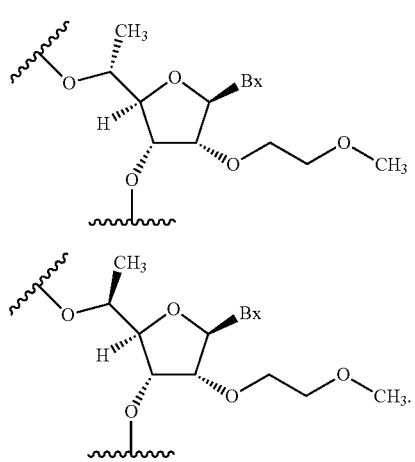

Example 58

Gapped Oligomeric Compounds Targeted to PTEN: In Vivo Study

In accordance with the present disclosure, oligomeric compounds are synthesized and tested for their ability to reduce PTEN expression in vivo at doses of 20 and 60 mg/kg. Six week old male Balb/c mice (Jackson Laboratory, Bar Harbor, Me.) are administered a single intraperitoneal (i.p) injection at either 20 or 60 mg/kg of a 2-10-2 gapped oligomer. A 5-10-5 gapped oligomer having 2'-O-MOE modified nucleosides or other modified nucleosides as provided herein in the wings is also included for comparison. Other motifs as disclosed herein are also amenable to in vivo testing.

Each dose group will include four animals. The mice are sacrificed 48 hours following the final administration to determine the PTEN mRNA levels in liver using real-time PCR and RIBOGREEN® RNA quantification reagent (Molecular Probes, Inc. Eugene, Oreg.) according to standard protocols. PTEN mRNA levels are determined relative to total RNA (using Ribogreen), prior to normalization to saline-treated control. The average % inhibition of mRNA expression for each treatment group, normalized to saline-injected control is determined.

Liver transaminase levels, alanine aminotranferease (ALT) and aspartate aminotransferase (AST), in serum are measured relative to saline injected mice.

| SEQ ID NO | Composition (5' to 3') |
|---|---|
| 07 | $^{me}C_xT_xG_x{}^{me}C_xT_xAG^{me}C^{me}CT^{me}CTGGAT_xT_xT_xG_xA_x$ |
| 08 | $C_xT_xTAGCACTGGCC_xT_x$ |
| 08 | $P-C_xT_xTAGCACTGGCC_xT_x$ |
| 08 | $^{me}C_xT_xTAGCACTGGC^{me}C_xT_x$ |

Each unmodified nucleoside is a β-D-2'-deoxyribonucleoside. Each internucleoside linkage is a phosphorothioate internucleoside linkage. A "P" at the 5'-end indicates a 5'-phosphate group. $^{me}C$ indicates a 5'-methyl cytosine nucleoside. Each nucleoside having a subscript x is selected from the list at the end of Example 57, e.g., Rb, Sb, Rc, Sc, Rd and Sd.

In general, each modified nucleoside having an x after it will have the same sugar modification but can have different bases.

Example 59

Oligomeric Compounds Targeted to PTEN: In Vitro Study

In accordance with the present disclosure, oligomeric compounds were synthesized and tested for their ability to reduce PTEN expression over a range of doses. Human HeLa cells were treated with either ISIS 447581 or ISIS 404320. A dose comparison was evaluated with dose concentrations of 0.20, 0.62, 1.9, 5.5, 16.7 and 50 nM using methods described herein. Expression levels of PTEN were determined using real-time PCR and normalized to RIBOGREEN™ using methods described herein. The percent inhibition of PTEN mRNA was determined. Resulting dose-response curves were used to determine the $EC_{50}$. Tm's were assessed in 100 mM phosphate buffer, 0.1 mM EDTA, pH 7, at 260 nm using 4 µM modified oligomers and 4 µM complementary RNA. The $EC_{50}$s are listed below.

| SEQ ID NO./ ISIS NO. | Composition (5' to 3') | EC50 (nM) |
|---|---|---|
| 06/447581 | $P-T_{Rc}U_fG_mU_fC_mU_fC_mU_fG_mG_fU_mC_fC_m-\underline{U_fU_m}A_fC_m\underline{U_fU_m}A_eA_e$ | 0.87 |
| 05/404320 | $P-U_fU_fG_fU_fC_fU_fC_fU_fG_fG_fU_fC_fC_fU_fU_f-\underline{A_fC_fU_fU_f}A_eA_e$ | 13.2 |

Each nucleoside is connected to the following nucleoside by a phosphodiester internucleoside linkage except underlined nucleosides which are connected to the following nucleoside by a phosphorothioate internucleoside linkage (going 5' to 3'). A "P" at the 5'-end indicates a 5'-phosphate group. Nucleosides followed by a subscript f, m or e are sugar modified nucleosides. A subscript "f" indicates a 2'-fluoro modified nucleoside, a subscript "m" indicates 2'-O-methyl modified nucleoside, a subscript "e" indicates a 2'-O(CH$_2$)$_2$OCH$_3$ (MOE) modified nucleoside and a subscript Re indicates the 2',5'-bis modified nucleoside listed in Example 57.

Example 60

Modified ssRNA 5'-Phosphate Serum Stability Assay

A serum stability assay is useful for evaluating the stability of oligomeric compounds in the presences of nucleases and other enzymes found in serum. For example, the stability of a 5'-terminal phosphate group of an oligomeric compound can be evaluated by assessing the ability of the 5'-terminal phosphate group to remain attached to the oligomeric compound in the presence of serum. Accordingly, a serum stability assay was employed to evaluate the stability of modified ssRNAs having a 5'-terminal phosphate group.

Various modified ssRNAs, shown below, having a 5'-terminal phosphate group (10 µM) were dissolved in 95% of fresh mouse serum and incubated at 37° C. Aliquots of serum (100 µL) were removed after 0, 1, 3, 6 or 24 hours of incubation times. The serum samples were immediately quenched and snap frozen. The samples were extracted by the strong anion exchange (SAX) and octadecylsilyl (C-18) columns. For each incubation time, the amount of full length modified ssRNA having a 5'-terminal phosphate group was determined by LC/MS, and the half-life of the full length modified ssRNA having a 5' terminal phosphate group was calculated. The results are expressed as half-time ($T_{1/2}$) in the table below. These data demonstrate that modifications to oligomeric compounds can improve the stability of the 5'-terminal phosphate group.

| SEQ ID NO./ ISIS NO. | Composition (5' to 3') | $T_{1/2}$ (h) |
|---|---|---|
| 05/404320 | P-U$_f$U$_f$G$_f$U$_f$C$_f$U$_f$C$_f$U$_f$G$_f$G$_f$U$_f$C$_f$C$_f$U$_f$U$_f$A$_f$C$_f$U$_f$U$_f$A$_e$A$_e$ | 4 |
| 09/398701 | P-U$_S$U$_f$G$_f$U$_f$C$_f$U$_f$C$_f$U$_f$G$_f$G$_f$U$_f$C$_f$C$_f$U$_f$U$_f$A$_f$C$_f$U$_f$U$_f$ | 18.2 |
| 06/432356 | P-T$_R$U$_f$G$_f$U$_f$C$_f$U$_f$C$_f$U$_f$G$_f$G$_f$U$_f$C$_f$C$_f$U$_f$U$_f$A$_f$C$_f$U$_f$U$_f$A$_e$A$_e$ | 8.7 |
| 06/422391 | P-T$_d$U$_f$G$_f$U$_f$C$_f$U$_f$C$_f$U$_f$G$_f$G$_f$U$_f$C$_f$C$_f$U$_f$U$_f$A$_f$C$_f$U$_f$U$_f$A$_e$A$_e$ | 6.5 |

Each nucleoside is connected to the following nucleoside by a phosphodiester internucleoside linkage except underlined nucleosides which are connected to the following nucleoside by a phosphorothioate internucleoside linkage (going 5' to 3'). A "P" at the 5'-end indicates a 5'-phosphate group. Nucleosides followed by a subscript d, e, f, R or Sf are sugar modified nucleosides. A subscript "d" indicates a 2'-O-dimethylaminoethyl acetamide (DMAEAc) modified nucleoside, a subscript "e" indicates a 2'-O(CH$_2$)$_2$OCH$_3$ (MOE) modified nucleoside, a subscript "f" indicates a 2'-fluoro modified nucleoside, a subscript "R" indicates (R)-5'-methyl-2'-deoxyribonucleoside and a subscript Sf indicates the 2',5'-bis modified nucleoside listed below.

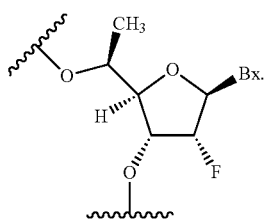

Sf

Example 61

Design and Screening of Duplexed Antisense Compounds

In accordance with the present invention, a series of nucleic acid duplexes comprising the compounds of the present invention and their complements can be designed. The nucleobase sequence of the antisense strand of the duplex comprises at least a portion of an antisense oligonucleotide targeted to a target sequence as described herein. The ends of the strands may be modified by the addition of one or more natural or modified nucleosides to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG (SEQ ID NO: 10) and having a two-nucleobase overhang of deoxythymidine(dT) would have the following structure:

```
cgagaggcggacgggaccgdTdT   Antisense  SEQ ID NO: 11
|||||||||||||||||||       Strand
dTdTgctctccgcctgccctggc   Complement SEQ ID NO: 12
                          Strand
```

In another embodiment, a duplex comprising an antisense strand having the same sequence CGAGAGGCGGACGGGACCG (SEQ ID NO: 10) may be prepared with blunt ends (no single stranded overhang) as shown:

```
cgagaggcggacgggaccg    Antisense    SEQ ID NO: 10
|||||||||||||||||||    Strand
gctctccgcctgccctggc    Complement   SEQ ID NO: 13
                       Strand
```

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 µM. Once diluted, 30 µL of each strand is combined with 15 µL of a 5× solution of annealing buffer. The final concentration of the buffer is 100 mM potassium acetate, 30 mM HEPES-KOH pH 7.4, and 2 mM magnesium acetate. The final volume is 75 µL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 µM.

Once prepared, the duplexed compounds are evaluated for their ability to modulate target mRNA levels. When cells reach 80% confluency, they are treated with duplexed compounds of the invention. For cells grown in 96-well plates, wells are washed once with 200 µL OPTI-MEM-1™ reduced-serum medium (Gibco BRL) and then treated with 130 µL of OPTI-MEM-1™ containing 5 µg/mL LIPOFECTAMINE 2000™ (Invitrogen Life Technologies, Carlsbad, Calif.) and the duplex antisense compound at the desired final concentration. After about 4 hours of treatment, the medium is replaced with fresh medium. Cells are harvested 16 hours after treatment, at which time RNA is isolated and target reduction measured by quantitative real-time PCR as described herein.

Example 62

5' and 2' Bis-Substituted Modified Oligomeric Compounds Targeting PTEN—In Vitro Study (ssRNAs vs siRNAs)

A series of 5' and 2' bis-substituted modified oligomeric compounds were prepared as single strand RNAs (ssRNAs). The antisense (AS) strands listed below were designed to target human PTEN, and each was also assayed as part of a duplex with the same sense strand (ISIS 341401, shown below) for their ability to reduce PTEN expression levels. HeLa cells were treated with the single stranded or double stranded oligomeric compounds created with the antisense compounds shown below using methods described herein. The IC$_{50}$'s were calculated using the linear regression equation generated by plotting the normalized mRNA levels to the log of the concentrations used.

| SEQ ID NO./ ISIS NO. | | Composition (5' to 3') | EC$_{50}$ (nM) ssRNA/siRNA |
|---|---|---|---|
| 14/341401 | (S) | P-AAGUAAGGACCAGAGACAA | —/— |
| 05/418046 | (AS) | P-U$_m$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ | 2.0/0.2 |
| 06/447581 | (AS) | P-T$_{Rc}$U$_m$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ | 1.0/0.4 |
| 06/467074 | (AS) | P-T$_{Sc}$U$_m$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ | 2.5/0.1 |
| 05/467076 | (AS) | Py-$^{me}$U$_m$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ | 6.0/.05 |
| 05/462606 | (AS) | Pz-$^{me}$U$_m$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ | 50/0.4 |
| 05/462607 | (AS) | Pz-$^{me}$U$_m$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ | 50/1.0 |
| 05/460646 | (AS) | Pz-$^{me}$U$_h$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ | 50/0.8 |
| 09/359455 | (AS) | P-UUGUCUCUGGUCCUUACUU | 50/0.3 |
| 09/386187 | (AS) | P-U$_f$U$_f$G$_f$U$_f$C$_f$U$_f$C$_f$U$_f$G$_f$G$_f$U$_f$C$_f$C$_f$U$_f$U$_f$A$_f$C$_f$U$_f$U$_f$ | 15/0.3 |
| 05/404320 | (AS) | P-U$_f$U$_f$G$_f$U$_f$C$_f$U$_f$C$_f$U$_f$G$_f$G$_f$U$_f$C$_f$C$_f$U$_f$U$_f$A$_f$C$_f$U$_f$U$_f$A$_e$A$_e$ | 5/0.5 |
| 06/422391 | (AS) | P-T$_d$U$_f$G$_f$U$_f$C$_f$U$_f$C$_f$U$_f$G$_f$G$_f$U$_f$C$_f$C$_f$U$_f$U$_f$A$_f$C$_f$U$_f$U$_f$A$_e$A$_e$ | 5/0.5 |
| 06/432356 | (AS) | P-T$_R$U$_f$G$_f$U$_f$C$_f$U$_f$C$_f$U$_f$G$_f$G$_f$U$_f$C$_f$C$_f$U$_f$U$_f$A$_f$C$_f$U$_f$U$_f$A$_e$A$_e$ | 3/0.7 |
| 06/435397 | (AS) | P-T$_d$U$_m$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ | 2/0.4 |

Each internucleoside linkage is a phosphodiester except that underlined nucleosides are linked to the following nucleoside by a phosphorothioate (going 5' to 3'). Each nucleoside not followed by a subscript is a ribonucleoside. A "P" at the 5'-end indicates a 5'-phosphate group. A "Py" at the 5'-end indicates a 5'-methylenephosphonate group, $(PO(OH)_2CH_2—)$. A "Pz" at the 5'-end indicates a 5'-difluoromethylenephosphonate group, $(PO(OH)_2CF_2—)$. Nucleosides followed by a subscript indicate modification as follows: subscript "d" indicates a 2'-O-dimethylaminoethyl acetamide (DMAEAc) modified nucleoside; subscript "e" indicates a 2'-O(CH$_2$)$_2$OCH$_3$ (MOE) modified nucleoside, subscript "f" indicates a 2'-fluoro modified nucleoside; subscript "m" indicates 2'-O-methyl modified nucleoside; and subscript "R" indicates a (R)-5'-methyl-2'-deoxyribonucleoside. Superscript "me" indicates a 5-methyl group on the pyrimidine base of the nucleoside. Nucleosides with subscripts "Rc" or "Sc" are shown below.

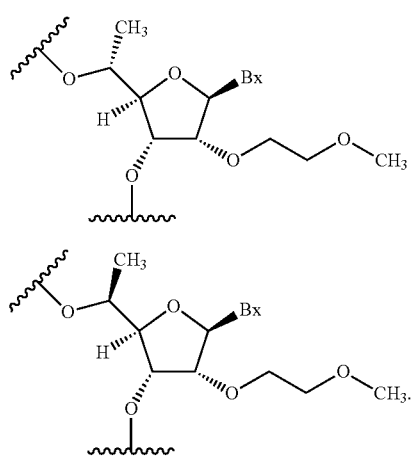

Rc

Sc

Example 63

Modified Oligomeric Compounds Targeting PTEN: In Vitro Study

In accordance with the present disclosure, oligomeric compounds were synthesized and tested for their ability to reduce PTEN expression over a range of doses. Human HeLa cells were treated with either ISIS 447581, 467074, 418046 or 467076. A dose comparison was evaluated with dose concentrations of 0.067, 0.2, 0.62, 1.9, 5.5, 16.7 and 50 nM using methods described herein. Expression levels of PTEN were determined using real-time PCR and normalized to RIBOGREEN™ using methods described herein. The percent inhibition of PTEN mRNA was determined and the resulting dose-response curves were used to determine the EC$_{50}$. The EC$_{50}$s are listed below.

| SEQ ID NO./ ISIS NO. | | Composition (5' to 3') | EC$_{50}$ (nM) |
|---|---|---|---|
| 06/447581 | | P-T$_{Rc}$U$_m$G$_m$U$_f$C$_m$U$_f$C$_m$U$_f$G$_m$G$_f$U$_m$C$_f$C$_m$U$_f$U$_m$A$_f$ C$_m$U$_f$U$_m$A$_e$A$_e$ | 0.6 |
| 06/467074 | | P-T$_{Sc}$U$_m$G$_m$U$_f$C$_m$U$_f$C$_m$U$_f$G$_m$G$_f$U$_m$C$_f$C$_m$U$_f$U$_m$A$_f$ C$_m$U$_f$U$_m$A$_e$A$_e$ | 2.5 |
| 05/418046 | | P-U$_m$U$_f$G$_m$U$_f$C$_m$U$_f$C$_m$U$_f$G$_m$G$_f$U$_m$C$_f$C$_m$U$_f$U$_m$A$_f$ C$_m$U$_f$U$_m$A$_e$A$_e$ | 0.83 |
| 05/467076 | | Py-$^{me}$U$_m$U$_f$G$_m$U$_f$C$_m$U$_f$C$_m$U$_f$G$_m$G$_f$U$_m$C$_f$C$_m$U$_f$U$_m$ A$_f$C$_m$U$_f$U$_m$A$_e$A$_e$ | 6.0 |

Each internucleoside linkage is a phosphodiester except that underlined nucleosides are linked to the following nucleoside by a phosphorothioate (going 5' to 3'). A "P" at the 5'-end indicates a 5'-phosphate group. A "Py" at the 5'-end indicates a 5'-methylenephosphonate group, $(PO(OH)_2CH_2—)$. Nucleosides followed by a subscript e, form indicate modification as follows: subscript "e" indicates a 2'-O(CH$_2$)$_2$OCH$_3$ (MOE) modified nucleoside, subscript "f" indicates a 2'-fluoro modified nucleoside; subscript "m" indicates 2'-O-methyl modified nucleoside. Superscript "me" indicates a 5-methyl group on the pyrimidine base of the nucleoside. Nucleosides with subscripts "Rc" or "Sc" are shown below.

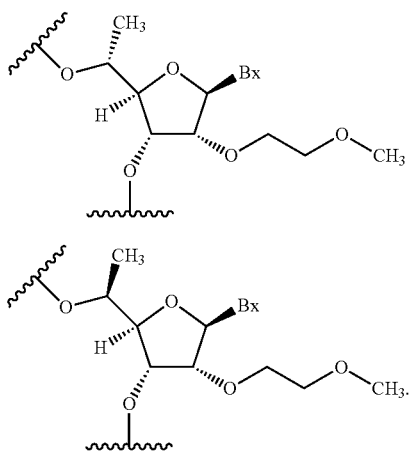

Example 64 ssRNAs Stability in Hepatocyte Cell Homogenate Assay—In Vivo Study

The stability of oligomeric compounds can be evaluated in a cell homogenate assay. Hepatocytes were harvested from balk mice in ice-cold hepatocyte wash media (William E Media) with fetal bovine serum, sedimented by centrifugation at 1000 g for 8 minutes and then washed with hepatocyte wash media. Hepatocytes were homogenized with RIPA buffer (50 mM Tris pH 7.5, 10 mM $MgCl_2$, 150 mM NaCl, 0.5% NP-40 alternative, one tablet of Roche protease inhibitor #11836170001), and centrifuged at 14000 g for 15 minutes at 4° C. and the supernatant was removed and stored in ice. Protein concentration (BSA mg/mL) was determined with Bradford assay and adjusted to a final protein concentration of 2 mg/mL by addition of Ripa buffer volume or cell homogenate volume.

Phenol/Choroform Extraction ssRNA (1 mL, 20 µL) were homogenized in a homogenation buffer (20 mM Tris, pH 8, 20 mM EDTA and 0.1 M NaCl in 0.5% NP-40) at time points 0, 5, 10, 20, 30, 40 and 60 minutes (Exception: 06/408877 at time points 0, 15, 30, 60, 120 and 240 mins, 06/409044, at time points 0, 0.5, 1, 2, 4, 8, and 18 hours). An internal standard (18/355868, a 27-mer, 2'-O-methoxyethyl-modified phosphorothioate oligonucleotide, or 19/116847, a 5-10-5 gapmer, 2'-O-methoxyethyl-modified phosphorothioate oligonucleotide) with concentration at 20 µg/g was added prior to extraction. Tissue samples were extracted with 70 µL of $NH_4OH$ and 240 µL of phenol/chloroform/isoamyl alcohol (25:24:1). The supernatant was removed after centrifugation at 14000 rpm for 2 mM. The remaining extractant was vortexed with an additional 500 µL of water and the aqueous layer was removed and combined with the supernatant after centrifugation at 14000 rpm for 2 minutes.

Solid Phase Extraction

Triethylammonium acetate solution at 1M (500 µL) was added to the supernatant. The aqueous layer of the mixture was loaded onto the pre-conditioned Biotage™ Phenyl Solid Phase Extraction Plate (SPE plate) after centrifugation at 9000 rpm for 20 minutes. The SPE plate was washed several times with water. The sample was then eluted with 1.5 mL of 1% TEA in 90% MeOH and filtered through the Protein Precipitation Plate (Phenomenex™). The elutent was evaporated to dryness and diluted to 200 µL with 50% quenching buffer (8 M urea, 50 mM EDTA) and water before sample injection.

LC-MS

An Agilent 1100 Series LC/MSD system was connected in-line to a mass spectrometry. Mass spectrometer was operated in the electrospray negative ionization mode. The nebulizer nitrogen gas was set at 325 psi and the drying nitrogen gas was set at 12 L/min. The drying temperature was 325° C. Samples (25 µL/well) were introduced via an auto sampler and reversed-phase chromatography was carried out with an)(Bridge OST C18 2.5 µm 2.1 mm×50 mm HPLC column using a flow rate of 300 µL/min at 55° C. The ion pair buffers consisted of A: 5 mM tributylammonium acetate (TBAA) in 20% acetonitrile and B: 5 nM TBAA in 90% acetonitrile and the loading buffer was 25 mM TBAA in 25% Acetonitrile. Separation was performed on a 30% to 70% B in 9 min and then 80% B in 11 min gradient.

Quantitative analysis of oligonucleotide and internal standard by extracted ion chromatograms of the most abundant ions was performed using MSD ChemStation software.

Example 65

5'-Modified Oligomeric Compounds Targeting PTEN: In Vivo Study

In accordance with the present disclosure, oligomeric compounds were synthesized and tested for their ability to reduce PTEN expression in vivo at dose of 75 mg/kg. Six week old male Balb/c mice (Jackson Laboratory, Bar Harbor, Me.) were administered a single intraperitoneal (i.p) injection at 75 mg/kg of ISIS 467074 having a 5'-phosphate group and 467074 having a 5'-methylenephosphonate group, $(PO(OH)_2CH_2\text{—})$. A 5-10-5 gapped oligomer, ISIS 116847 having 2'-O-MOE modified nucleosides in wings with a 5'-phosphorothioate group was included for comparison.

Each dose group consisted of four animals. The mice were sacrificed 48 hours following the final administration to determine the PTEN mRNA levels in liver using real-time PCR and RIBOGREEN® RNA quantification reagent (Molecular Probes, Inc. Eugene, Oreg.) according to standard protocols. PTEN mRNA levels were determined relative to total RNA (using Ribogreen), prior to normalization to saline-treated control. Results are listed below as the average % inhibition of PTEN mRNA expression for each treatment group, normalized to saline-injected control.

| SEQ ID NO./ ISIS NO. | Composition (5' to 3') |
|---|---|
| 06/467074 | P-$T_{Sc}U_fG_mU_fC_mU_fC_mU_fG_mG_fU_mC_fC_mU_fU_mA_fC_mU_f$ $\underline{U_m}\underline{A_e}\underline{A_e}$ |
| 05/467076 | Py-$^{me}U_mU_fG_mU_fC_mU_fC_mU_fG_mG_fU_mC_fC_mU_fU_mA_fC_m$ $\underline{U_f}\underline{U_m}\underline{A_e}\underline{A_e}$ |
| 07/116847 | $^{me}C_eT_eG_e{}^{me}C_eT_eAG^{me}C^{me}CT^{me}CTGGAT_eT_eT_eG_eA_e$ |

Each internucleoside linkage is a phosphodiester except that underlined nucleosides are linked to the following nucleoside by a phosphorothioate (going 5' to 3'). A "P" at the 5'-end indicates a 5'-phosphate group. A "Py" at the 5'-end indicates a 5'-methylenephosphonate group, (PO(OH)$_2$CH$_2$—). Each unmodified nucleoside is a β-D-2'-deoxyribonucleosides. Nucleosides followed by a subscript e, f or m indicate modification as follows: subscript "e" indicates a 2'-O(CH$_2$)$_2$OCH$_3$ (MOE) modified nucleoside, subscript "f" indicates a 2'-fluoro modified nucleoside; subscript "m" indicates 2'-O-methyl modified nucleoside. Superscript "me" indicates a 5-methyl group on the pyrimidine base of the nucleoside. Nucleoside with subscript "Sc" is shown below.

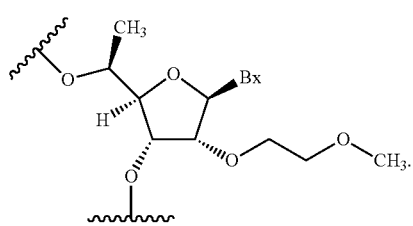

| | SEQ ID NO./ISIS NO | | | |
|---|---|---|---|---|
| | 06/467074 | 05/467076 | 07/116847 | Saline (Control) |
| Dose | 75 mg/kg | 75 mg/kg | 75 mg/kg | 0 mg/kg |
| Time (h) | 48 | 48 | 48 | 48 |
| % inhibition | 11 | 16 | 76 | 0% |

Example 66

Stability of 5'-Modified Oligomeric Compounds Targeting PTEN: In Vivo Study

The in vivo stability of the three oligomeric compounds in Example 65 was evaluated. The tissue samples were obtained from the animals in which PTEN was assessed. Tissue samples were collected and prepared using the same technique described in Example 64. Quantitative analysis of the oligonucleotides standard were performed by extracted ion chromatograms in the most abundant charge state (−4) using Chemstation software. The tissue level (μg/g) of intact compound of ISIS 116847, 467074 and 467076 was measured and are provided below.

| SEQ ID NO./ ISIS NO. | Dose @ 75 mg/kg (48 h time point) Tissue Level of intact compound (μg/g) |
|---|---|
| 06/467074 | none detected |
| 05/467076 | 22.5 |
| 07/116847 | 131.1 |

The 5-10-5 MOE gapmer compound was present at high levels and was a potent inhibitor of PTEN. Intact 467076 was present at a lower concentration and resulted in smaller inhibition of PTEN. Intact 467074 was not detected and resulted in the lowest amount of PTEN reduction. Some 467074 lacking the 5'-phosphate was detected.

What is claimed is:

1. An oligomeric compound comprising one monomer of Formula IV:

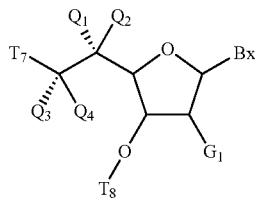

wherein:
Bx is a heterocyclic base moiety;
T₇ is a phosphorus moiety having the formula:

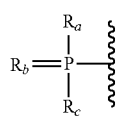

wherein:
$R_a$ and $R_c$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino; and
$R_b$ is O or S;
$T_8$ is an internucleoside linking group linking the monomer of Formula IV to the oligomeric compound;
$Q_1$, $Q_2$, $Q_3$ and $Q_4$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
$G_1$ is O—[C($R_2$)($R_3$)]$_n$—[(C=O)$_m$—X]$_j$—Z or halogen;
each $R_2$ and $R_3$ is, independently, H or halogen;
X is O, S or N($E_1$);
Z is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or N($E_2$)($E_3$);
$E_1$, $E_2$ and $E_3$ are each, independently, H, $C_1$-$C_6$ alkyl or substituted $C_1$-$C_6$ alkyl;
n is from 1 to about 6;
m is 0 or 1;
j is 0 or 1;
each substituted group comprises one or more optionally protected substituent groups independently selected from halogen, $OJ_1$, $N(J_1)(J_2)$, =$NJ_1$, $SJ_1$, $N_3$, CN, OC(=L)$J_1$, OC(=L)N($J_1$)($J_2$) and C(=L)N($J_1$)($J_2$);
L is O, S or $NJ_3$;
each $J_1$, $J_2$ and $J_3$ is, independently, H or $C_1$-$C_6$ alkyl;
provided that when j is 1 then Z is other than N($E_2$)($E_3$);
provided that when $Q_1$, $Q_2$, $Q_3$ and $Q_4$ are each H then $G_1$ is other than H or OH; and
wherein said oligomeric compound comprises from 8 to 40 monomeric subunits and is complementary to at least a portion of a nucleic acid target.

2. The oligomeric compound of claim 1 wherein Bx is uracilyl, thyminyl, cytosinyl, 5-methylcytosinyl, adeninyl, or guaninyl.

3. The oligomeric compound of claim 1 wherein $G_1$ is $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—CH=$CH_2$, $O(CH_2)_2$—$OCH_3$, $O(CH_2)_2$—$SCH_3$, $O(CH_2)_2$—$OCF_3$, $O(CH_2)_3$—$N(R_4)(R_5)$, $O(CH_2)_2$—$ON(R_4)(R_5)$, $O(CH_2)_2$—$O(CH_2)_2$—$N(R_4)(R_5)$, $OCH_2C(=O)$—$N(R_4)(R_5)$, $OCH_2C(=O)$—$N(R_6)$—$(CH_2)_2$—$N(R_4)(R_5)$ or $O(CH_2)_2$—$N(R_6)$—$C(=NR_7)$[$N(R_4)(R_5)$] wherein $R_4$, $R_5$, $R_6$ and $R_7$ are each, independently, H or $C_1$-$C_6$ alkyl.

4. The oligomeric compound of claim 1 wherein $G_1$ is F, $OCH_3$, $O(CH_2)_2$—$OCH_3$, $OCH_2C(=O)$—$N(H)CH_3$ or $OCH_2C(=O)$—$N(H)$—$(CH_2)_2$—$N(CH_3)_2$.

5. The oligomeric compound of claim 1 wherein $Q_1$, $Q_2$, $Q_3$ and $Q_4$ are each H.

6. The oligomeric compound of claim 1 wherein one of $Q_1$, $Q_2$, $Q_3$ and $Q_4$ is F or $C_1$-$C_6$ alkyl and the other three of $Q_1$, $Q_2$, $Q_3$ and $Q_4$ are each H.

7. The oligomeric compound of claim 1 wherein two of $Q_1$, $Q_2$, $Q_3$ and $Q_4$ are F.

8. The oligomeric compound of claim 7 wherein $Q_3$ and $Q_4$ are each F and $Q_1$ and $Q_2$ are each H.

9. The oligomeric compound of claim 1 wherein $Q_1$ is $CH_3$ and $Q_2$, $Q_3$ and $Q_4$ are each H or $Q_2$ is $CH_3$ and $Q_1$, $Q_3$ and $Q_4$ are each H.

10. The oligomeric compound of claim 1 wherein each monomer of Formula IV has the configuration:

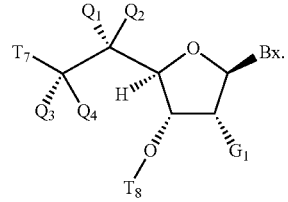

11. The oligomeric compound of claim 1 wherein each internucleoside linking group is, independently, a phosphodiester internucleoside linking group or a phosphorothioate internucleoside linking group.

12. The oligomeric compound of claim 1 wherein essentially each internucleoside linking group is a phosphorothioate internucleoside linking group.

13. A double stranded composition comprising:
a first oligomeric compound and a second oligomeric compound wherein the first oligomeric compound is complementary to the second oligomeric compound and the second oligomeric compound is complementary to a nucleic acid target;

at least one of the first and second oligomeric compounds is an oligomeric compound according to claim 1; and wherein said composition optionally comprises one or more 5' or 3' terminal groups.

14. A pharmaceutical composition comprising a pharmaceutically acceptable carrier and an oligomeric compound comprising one monomer of Formula IV:

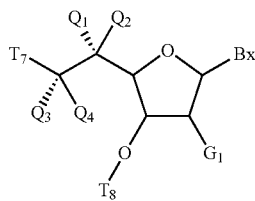

IV wherein:

Bx is a heterocyclic base moiety;

$T_7$ is a phosphorus moiety having the formula:

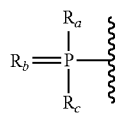

wherein:

$R_a$ and $R_c$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino; and $R_b$ is O or S;

$T_8$ is an internucleoside linking group linking the monomer of Formula IV to the oligomeric compound;

$Q_1$, $Q_2$, $Q_3$ and $Q_4$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$G_1$ is O—$[C(R_2)(R_3)]_n$—$[(C{=}O)_m$—$X]_j$—Z or halogen;

each $R_2$ and $R_3$ is, independently, H or halogen;

X is O, S or $N(E_1)$;

Z is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $={N}J_1$, $SJ_1$, $N_3$, CN, $OC({=}L)J_1$, $OC({=}L)N(J_1)(J_2)$ and $C({=}L)N(J_1)(J_2)$;

L is O, S or $NJ_3$;

each $J_1$, $J_2$ and $J_3$ is, independently, H or $C_1$-$C_6$ alkyl;

provided that when j is 1 then Z is other than $N(E_2)(E_3)$;

provided that when $Q_1$, $Q_2$, $Q_3$ and $Q_4$ are each H then $G_1$ is other than H or OH; and wherein said oligomeric compound comprises from 8 to 40 monomeric subunits and is complementary to at least a portion of a nucleic acid target.

15. The pharmaceutical composition of claim 14 wherein Bx is uracilyl, thyminyl, cytosinyl, 5-methylcytosinyl, adeninyl, or guaninyl.

16. The pharmaceutical composition of claim 14 wherein $G_1$ is $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—CH=$CH_2$, $O(CH_2)_2$—$OCH_3$, $O(CH_2)_2$—$SCH_3$, $O(CH_2)_2$—$OCF_3$, $O(CH_2)_3$—$N(R_4)(R_5)$, $O(CH_2)_2$—$ON(R_4)(R_5)$, $O(CH_2)_2$—$O(CH_2)_2$—$N(R_4)(R_5)$, $OCH_2C({=}O)$—$N(R_4)(R_5)$, $OCH_2C({=}O)$—$N(R_6)$—$(CH_2)_2$—$N(R_4)(R_5)$ or $O(CH_2)_2$—$N(R_6)$—$C({=}NR_7)[N(R_4)(R_5)]$ wherein $R_4$, $R_5$, $R_6$ and $R_7$ are each, independently, H or $C_1$-$C_6$ alkyl.

17. The pharmaceutical composition of claim 14 wherein $G_1$ is F, $OCH_3$, $O(CH_2)_2$—$OCH_3$, $OCH_2C({=}O)$—$N(H)CH_3$ or $OCH_2C({=}O)$—$N(H)$—$(CH_2)_2$—$N(CH_3)_2$.

18. The pharmaceutical composition of claim 14 wherein: a) $Q_1$, $Q_2$, $Q_3$ and $Q_4$ are each H, b) wherein one of $Q_1$, $Q_2$, $Q_3$ and $Q_4$ is F or $C_1$-$C_6$ alkyl and the other three of $Q_1$, $Q_2$, $Q_3$ and $Q_4$ are each H, or c) wherein two of $Q_1$, $Q_2$, $Q_3$ and $Q_4$ are F.

19. The pharmaceutical composition of claim 14 wherein $Q_3$ and $Q_4$ are each F and $Q_1$ and $Q_2$ are each H.

20. The pharmaceutical composition of claim 14 wherein $Q_1$ is $CH_3$ and $Q_2$, $Q_3$ and $Q_4$ are each H or $Q_2$ is $CH_3$ and $Q_1$, $Q_3$ and $Q_4$ are each H.

21. The pharmaceutical composition of claim 14 wherein each monomer of Formula IV has the configuration:

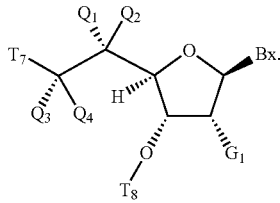

22. The pharmaceutical composition of claim 14 wherein each internucleoside linking group is, independently, a phosphodiester internucleoside linking group or a phosphorothioate internucleoside linking group.

23. The pharmaceutical composition of claim 14 wherein essentially each internucleoside linking group is a phosphorothioate internucleoside linking group.

* * * * *

SEQUENCE LISTING

```
<160> NUMBER OF SEQ ID NOS: 14

<210> SEQ ID NO 1
<211> LENGTH: 3160
<212> TYPE: DNA
<213> ORGANISM: H. sapiens

<400> SEQUENCE: 1
cctcccctcg cccggcgcgg tcccgtccgc ctctcgctcg cctcccgcct cccctcggtc      60
ttccgaggcg cccgggctcc cggcgcggcg gcggaggggg cgggcaggcc ggcgggcggt     120
gatgtggcag gactctttat gcgctgcggc aggatacgcg ctcggcgctg ggacgcgact     180
gcgctcagtt ctctcctctc ggaagctgca gccatgatgg aagtttgaga gttgagccgc     240
tgtgaggcga ggccgggctc aggcgaggga gatgagagac ggcggcggcc gcggcccgga     300
gcccctctca gcgcctgtga gcagccgcgg gggcagcgcc ctcggggagc cggccggcct     360
gcggcggcgg cagcggcggc gtttctcgcc tcctcttcgt cttttctaac cgtgcagcct     420
cttcctcggc ttctcctgaa agggaaggtg gaagccgtgg gctcggggcgg gagccggctg     480 aggcgcggcg gcggcggcgg cggcacctcc cgctcctgga gcggggggga gaagcggcgg     540
cggcggcggc cgcggcggct gcagctccag ggaggggtc tgagtcgcct gtcaccattt     600
ccagggctgg gaacgccgga gagttggtct ctccccttct actgcctcca acacggcggc     660
ggcggcggcg gcacatccag ggacccgggc cggtttaaa cctcccgtcc gccgccgccg     720 cacccccgt ggcccgggct ccggaggccg ccggcggagg cagccgttcg gaggattatt     780
cgtcttctcc ccattccgct gccgccgctg ccaggcctct ggctgctgag gagaagcagg     840
```

```
cccagtcgct gcaaccatcc agcagccgcc gcagcagcca ttacccggct gcggtccaga    900
gccaagcggc ggcagagcga ggggcatcag ctaccgccaa gtccagagcc atttccatcc    960
tgcagaagaa gccccgccac cagcagcttc tgccatctct ctcctccttt ttcttcagcc   1020
acaggctccc agacatgaca gccatcatca aagagatcgt tagcagaaac aaaaggagat   1080
atcaagagga tggattcgac ttagacttga cctatattta tccaaacatt attgctatgg   1140
gatttcctgc agaaagactt gaaggcgtat acaggaacaa tattgatgat gtagtaaggt   1200
ttttggattc aaagcataaa accattaca agatatacaa tctttgtgct gaaagacatt   1260
atgacaccgc caaatttaat tgcagagttg cacaatatcc ttttgaagac cataacccac   1320
cacagctaga acttatcaaa ccctttttgtg aagatcttga ccaatggcta agtgaagatg   1380
acaatcatgt tgcagcaatt cactgtaaag ctggaaaggg acgaactggt gtaatgatat   1440
gtgcatattt attacatcgg ggcaaatttt taaaggcaca agaggcccta gatttctatg   1500
gggaagtaag gaccagagac aaaaagggag taactattcc cagtcagagg cgctatgtgt   1560
attattatag ctacctgtta aagaatcatc tggattatag accagtggca ctgttgtttc   1620
acaagatgat gtttgaaact attccaatgt tcagtggcgg aacttgcaat cctcagtttg   1680
tggtctgcca gctaaaggtg aagatatatt cctccaattc aggacccaca cgacgggaag   1740
acaagttcat gtactttgag ttccctcagc cgttacctgt gtgtggtgat atcaaagtag   1800
agttcttcca caaacagaac aagatgctaa aaaaggacaa aatgtttcac ttttgggtaa   1860
atacattctt cataccagga ccagaggaaa cctcagaaaa agtagaaaat ggaagtctat   1920
gtgatcaaga aatcgatagc atttgcagta tagagcgtgc agataatgac aaggaatatc   1980
tagtacttac tttaacaaaa aatgatcttg acaaagcaaa taaagacaaa gccaaccgat   2040
acttttctcc aaattttaag gtgaagctgt acttcacaaa aacagtagag gagccgtcaa   2100
atccagaggc tagcagttca acttctgtaa caccagatgt tagtgacaat gaacctgatc   2160
attatagata ttctgacacc actgactctg atccagagaa tgaaccttttt gatgaagatc   2220 agcatacaca aattacaaaa gtctgaattt tttttttatca agagggataa acaccatga   2280 aaataaactt gaataaactg aaaatggacc ttttttttttt taatggcaat aggacattgt   2340
gtcagattac cagttatagg aacaattctc ttttcctgac caatcttgtt ttaccctata   2400
catccacagg gttttgacac ttgttgtcca gttgaaaaaa ggttgtgtag ctgtgtcatg   2460
tatatacctt tttgtgtcaa aaggacattt aaaattcaat taggattaat aaagatggca   2520
ctttcccgtt ttattccagt tttataaaaa gtggagacag actgatgtgt atacgtagga   2580 atttttttcct tttgtgttct gtcaccaact gaagtggcta aagagctttg tgatatactg   2640
gttcacatcc tacccctttg cacttgtggc aacagataag tttgcagttg gctaagagag   2700
gtttccgaaa ggttttgcta ccattctaat gcatgtattc gggttagggc aatggagggg   2760
aatgctcaga aaggaaataa ttttatgctg gactctggac catataccat ctccagctat   2820
ttacacacac ctttctttag catgctacag ttattaatct ggacattcga ggaattggcc   2880
gctgtcactg cttgttgttt gcgcattttt tttaaagca tattggtgct agaaaaggca   2940
gctaaaggaa gtgaatctgt attggggtac aggaatgaac cttctgcaac atcttaagat   3000
ccacaaatga agggatataa aaataatgtc ataggtaaga aacacagcaa caatgactta   3060
accatataaa tgtggaggct atcaacaaag aatgggcttg aaacattata aaaattgaca   3120
atgatttatt aaatatgttt tctcaattgt aaaaaaaaaa                         3160
```

```
<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
aatggctaag tgaagatgac aatcat                                          26

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
tgcacatatc attacaccag ttcgt                                           25

<210> SEQ ID NO 4
<211> LENGTH: 30
<212> TYPE: DNA
<213> ORGANISM: Artificial Sequence
<220> FEATURE:
<223> OTHER INFORMATION: Probe

<400> SEQUENCE: 4
ttgcagcaat tcactgtaaa gctggaaagg                                      30

<210> SEQ ID NO 5
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 5
uugucucugg uccuuacuua a                                               21

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)...(21)
<223> OTHER INFORMATION: bases at these positions are RNA

<400> SEQUENCE: 6
tugucucugg uccuuacuua a                                               21

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
ctgctagcct ctggatttga                                                 20

<210> SEQ ID NO 8
<211> LENGTH: 14
```

```
<212> TYPE: DNA
<213> ORGANISM: Artificial Sequence
<220> FEATURE:
<223> OTHER INFORMATION: Synthetic oligonucleotide

<400> SEQUENCE: 8
cttagcactg gcct                                                         14

<210> SEQ ID NO 9
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 9
uugucucugg uccuuacuu                                                    19

<210> SEQ ID NO 10
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 10
cgagaggcgg acgggaccg                                                    19

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)...(19)
<223> OTHER INFORMATION: Bases at these positions are RNA

<400> SEQUENCE: 11
cgagaggcgg acgggaccgt t                                                 21

<210> SEQ ID NO 12
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 3, 4, 6, 8, 9, 10, 11, 12, 14, 15, 16, 17, 19, 20, 21
<223> OTHER INFORMATION: Bases at these positions are RNA

<400> SEQUENCE: 12
ttgctctccg cctgccctgg c                                                 21

<210> SEQ ID NO 13
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 13
gctctccgcc tgccctggc                                                    19

<210> SEQ ID NO 14
```

```
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 14
aaguaaggac cagagacaa                                              19
```